US008273549B2

(12) United States Patent
Gladyshev et al.

(10) Patent No.: US 8,273,549 B2
(45) Date of Patent: Sep. 25, 2012

(54) COMPOSITIONS AND METHODS FOR THE EXPRESSION OF SELENOPROTEINS IN EUKARYOTIC CELLS

(75) Inventors: Vadim Gladyshev, Lincoln, NE (US); Sergey Novoselov, Puschino (RU)

(73) Assignee: Board of Regents of the University of Nebraska, Lincoln, NE (US)

( * ) Notice: Subject to any disclaimer, the term of this patent is extended or adjusted under 35 U.S.C. 154(b) by 583 days.

(21) Appl. No.: 12/428,007

(22) Filed: Apr. 22, 2009

(65) Prior Publication Data

US 2009/0269807 A1    Oct. 29, 2009

Related U.S. Application Data

(60) Provisional application No. 61/125,822, filed on Apr. 29, 2008.

(51) Int. Cl.
  C12P 21/00    (2006.01)
  C07H 21/00    (2006.01)
  C12N 5/00     (2006.01)
(52) U.S. Cl. .................. 435/69.1; 435/325; 536/23.1
(58) Field of Classification Search ................... None
  See application file for complete search history.

(56) References Cited

U.S. PATENT DOCUMENTS 5,843,723 A    12/1998  Dubensky, Jr. et al.
  6,893,866 B1   5/2005   Westaway et al.
  7,109,178 B2   9/2006   Ji et al.

OTHER PUBLICATIONS

Novoselov et al A highly efficient form of the selenocysteine insertion sequence element in protozoan parasites and its use in mammalian cells. PNAS vol. 104 No. 19, p. 7857-7862.*
Grunder-Culemann et al. Two distinct SECIS structures capable of directing selenocysteine incorporation in eukaryotes. RNA (1999), 5:625-635.*
Korokov et al. Mammalian selenoprotein in which selenocysteine (Sec) incorporation is supported by a new form of Sec insertion sequence element. Molecular and Cellular Biology, Mar. 2002, p. 1402-1411.*
Gladyshev et al Selenocysteine, identifies as the penultimate C-terminal residue in human T-cell thioredoxin reductase, corresponds to TGA in the human placental gene PNAS vol. 93, pp. 6146-6151.*
High-level Expression in *Escherichia coli* of Selenoproteine-containing rat Thioredoxine reductase Utilizing gene Fusions with Engineered Bacterial type SECIS Elements and Co-expression with the selA, selB and selC Genes Journal of Molecular biology (1999), 292, 1003-1016.*
Arner et al., "High-Level Expression in *Escherichia coli* of Selenocysteine-Containing Rat Thioredoxin Reductase Utilizing Gene Fusions with Engineered Bacterial-Type SECIS Elements and Co-Expression with the selA, selB and selC Genes", J. Mol. Biol., 1999, pp. 1003-1016, vol. 292.

Atkins et al., "The Twenty-First Amino Acid", Nature, 2000, pp. 463 & 465, vol. 407.
Berry et al., "Recognition of UGA as a Selenocysteine Codon in Type I Deiodinase Requires Sequences in the 3' Untranslated Region", Nature, 1991, pp. 273-276, vol. 353.
Berry et al., "RNA and Protein Requirements for Eukaryotic Selenoprotein Synthesis", Biomed. Environ. Sci., 1997, pp. 182-189, vol. 10.
Bock et al., "Selenium: Its Molecular Biology and Role in Human Health", 2006, pp. 9-29.
Castellano et al., "Silica Identification of Novel Selenoproteins in the *Drosophila melanogaster* Genome", EMBO Rep., 2001, pp. 697-702, vol. 2.
Copeland et al., "A Novel RNA Binding Protein, SBP2, is Required for the Translation of Mammalian Selenoprotein mRNAs" EMBO Journal, 2000, pp. 306-314, vol. 19.
Eckenroth et al., "Semisynthesis and Characterization of Mammalian Thioredoxin Reductase", Biochemistry, 2006, pp. 5158-5170, vol. 45.
Fagegaltier et al., "Characterization of mSelB, a Novel Mammalian Elongation Factor for Selenoprotein Translation", EMBO Journal, 2000, pp. 4796-4805, vol. 19.
Website, "ftp//ftp.ncbi.nih.gov/genbank", Feb. 12, 2010, pp. 1-34.
Grundner-Culemann et al., "Two Distinct SECIS Structures Capable of Directing Selenocysteine Incorporation in Eukaryotes", RNA, 1999, pp. 625-635, vol. 5.
Hatfield et al., "Minireview: How Selenium Has Altered Our Understanding of the Genetic Code", Mol. Cell Biol., 2002, pp. 3565-3576, vol. 22.
Johansson et al., "Selenocysteine in Proteins-Properties and Biotechnological Use", Biochem Biophys Acta, 2005, pp. 1-13, vol. 1726.
Korotkov et al., "Mammalian Selenoprotein in Which Selenocysteine (Sec) Incorporation is Supported by a New Form of Sec Insertion Sequence Element", Molecular and Cellular Biology, Mar. 2002, pp. 1402-1411, vol. 22, No. 5.
Kryukov et al., "Characterization of Mammalian Selenoproteins", Science, 2003, pp. 1439-1443, vol. 300.
Lescure et al., "Novel Selenoproteins Identified in Silico and in Vivo by Using a Conserved RNA Structural Motif", J. Biol Chem., Dec. 31, 1999, pp. 38147-38154, vol. 274, No. 53.
Low et al., "Knowing When Not to Stop: Selenocysteine Incorporation in Eukaryotes", Trends Bichem Sci., 1996, pp. 203-208, vol. 21.
Low et al., "SECIS-SBP2 Interactions Dictate Selenocysteine Incorporation Efficiency and Selenoprotein Hierarchy", EMBO J. , 2000, pp. 6882-6890, vol. 19.
Martin et al., "Functionality of Mutations at Conserved Nucleotides in Eukaryotic SECIS Elements is Determined by the Identity of a Single Nonconserved Nucleotide" , RNA Journal, 1998, pp. 65-73, vol. 4.

(Continued)

*Primary Examiner* — Kagnew H Gebreyesus
(74) *Attorney, Agent, or Firm* — Thompson Coburn LLP

(57) ABSTRACT

Recombinant nucleic acid constructs for the efficient expression of eukaryotic selenoproteins and related methods for production of recombinant selenoproteins are provided. The nucleic acid constructs comprise novel selenocysteine insertion sequence (SECIS) elements. Certain novel SECIS elements of the invention contain non-canonical quartet sequences. Other novel SECIS elements provided by the invention are chimeric SECIS elements comprising a canonical SECIS element that contains a non-canonical quartet sequence and chimeric SECIS elements comprising a non-canonical SECIS element that contains a canonical quartet sequence. The novel SECIS elements of the invention facilitate the insertion of selenocysteine residues into recombinant polypeptides.

20 Claims, 23 Drawing Sheets

OTHER PUBLICATIONS

Martin et al., "Selenocysteine Incorporation in Eukaryotes: Insights Into Mechanism and Efficiency From Sequence, Structure, and Spacing Proximity Studies of the Type I Deiodinase SECIS Element", RNA Journal, 1996, pp. 171-182, vol. 2.

Rengby et al., "Titration and Conditional Knockdown of the prfB Gene in *Escherichia coli:* Effects on Growth and Overproduction of the Recombinant Mammalian Selenoprotein Thioredoxin Reductase", Appl. Environ. Microbiol., 2007, pp. 432-441, vol. 73.

Rother et al., "Minireview: Selenoprotein Synthesis in Archaea", Biofactors, 2001, pp. 75-83, vol. 14.

Stadtman. "Discoveries of Vitamin B12 and Selenium Enzymes", Annual Review of Biochemistry, Jul. 2002, pp. 1-16, vol. 71.

Su et al., "Selenocysteine Insertion Directed by the 3'-UTR SECIS Element in *Escherichia coli*", Nucleic Acids Res., 2005, pp. 2486-2492, vol. 33.

Tujebajeva et al., "Decoding Apparatus for Eukaryotic Selenocysteine Insertion", EMBO Rep., 2000, pp. 158-163, vol. 1.

Walczak et al., "A Novel RNA Structural Motif in the Selenocysteine Insertion Element of Eukaryotic Selenoprotein mRNAs", RNA, Apr. 1996, pp. 367-379, vol. 2.

Walczak et al., "An Essential Non-Watson-Crick Base Pair Motif in 3'UTR to Mediate Selenoprotein Translation", RNA, 1998, pp. 74-84, vol. 4.

Kryukov et al, New Mammalian Selenocysteine-Containing Proteins Identified with an Algorithm That Searches for Selenocysteine Insertion Sequence Elements, Journal of Biological Chemistry, Nov. 26, 1999 pp. 33888-33897, vol. 274, No. 48.

Novoselov et al., "Selenoproteins and Selenocysteine Insertion System in the Model Plant Cell System, Chlamydomonas Reinhardtii", The EMBO Journal, 2002, pp. 3681-3693, vol. 21.

Zhang et al., "The Microbial Selenoproteome of the Sargasso Sea", Genome Biology, 2005 p. R37, vol. 6.

Chavatte et al., "Ribosomal Protein L30 is a Component of the UGA-Selenocysteine Recoding Machinery in Eukaryotes", Nature Structural & Molecular Biology, May 2005, pp. 408-416, vol. 12.

Xu et al., "Evidence for Direct Roles of Two Additional Factors, SECp43 and Soluble Liver Antigen, in the Selenoprotein Synthesis Machinery", The Journal of Biological Chemistry, Dec. 16, 2005, pp. 41568-41575, vol. 280, No. 50.

Small-Howard et al., "Supramolecular Complexes Mediate Selenocysteine Incorporation in Vivo", Molecular and Cellular Biology, Mar. 2006., pp. 2337-2346. vol. 26, No. 6.

Allmang et al., "Chapter 5. SECIS RNAs and K-turn Binding Proteins. A Survey of Evolutionary Conserved RNA and Protein Motifs", eds, 2006, pp. 51-61, Pringer, New York.

Vidovic I et al., "Crystal Structure of the Spliceosomal 15.5kD Protein Bound to a U4 snRNA Fragment", Molecular Cell, Dec. 2000, pp. 1331-1342, vol. 6.

Chao et al., "Joint X-Ray and NMR Refinement of the Yeast L30e-mRNA Complex", Structure, Jul. 2004, pp. 1165-1176, vol. 12.

Moore et al., "Molecular Basis of Box C/D RNA-Protein Interactions: Cocrystal Structure of Archaeal L7A3 and a Box C.D RNA", Structure, May 2004, pp. 807-818, vol. 12.

* cited by examiner

FIGURE 1A

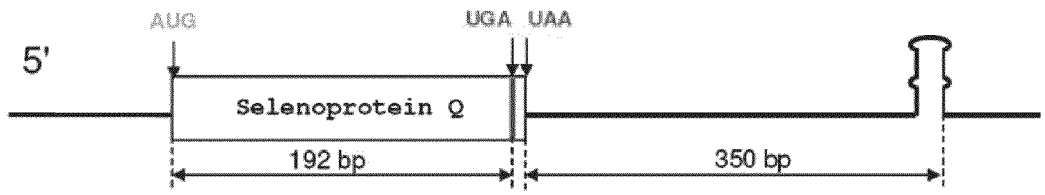

```
GAAGACCAGCGGAGATGCCAGTCAGCGAGGATGCGTTATGTGGAGAAGCTGGAAGGCGAA
ATGGAGGATTTCAAGAAAACAGAGGAGTTCAAAGAGCTAGAGAAGGAAGCTGCAGATCGA
 M   E   D   F   K   K   T   E   E   F   K   E   L   E   K   E   A   A   D   R      20

GAAAGAGGCATCCAACCAGAACATAGGCGAACCTGGCAGTTCAGGGGAACCATCCCGCAG
 E   R   G   I   Q   P   E   H   R   R   T   W   Q   F   R   G   T   I   P   Q      40

AATCCGCATTTGGCACCTAGATTCCGGCCCAACGTAAATGATCGCTATCAAATCCGGCGA
 N   P   H   L   A   P   R   F   R   P   N   V   N   D   R   Y   Q   I   R   R      60

GGCAGAGGGGGCTGATGCTAAAAGAAGAACATGTGCAAACGGTTGCACATGTTTTGACGA
 G   R   G   G   U   C   #                                                          66

GTGGCAACACTCTGCGAAGCACCATAACTTTTCGACCCTTGTTCATAAATACCGTCGGTGT
GCCAACGACGCTGCCCTACCCCAATTCTGGCTCACCTTTTGGAGTGTGGGAAGCGGCGACA
ATGACCGTTCTCGACAGCGAAGTATTTCAAGTAAACAACGATGAGTTGGGAAGAATTAGTT
CCCTCCACGTCTGACGGTGTTGTCAATGAGAGCGCAGGAAACGTGGTCATGAATGACGAGG
CACAGAAAACCGTTTTCGGATCGGTGCCTCTGAAAGGTGGTCGACCCCTGCCTCTTACAC
CTCAGTTTTTACGCTGCTGACAGGAGGTCAATTCCGTTTTAGCTTCGTGCTCGAACGTGAA
```

Figure 1B

```
C.reinhardtii     1  ------------------------------------LFYISRTGTVQ-ERRSPWRLSIVVFF
D.melanogaster    1  ------------------------------------MVYIDHNGRVW-EKRGPWDWRFIVLFF
D.discoideum      1  ---------------------------MPPKPIYVSGSVTQ-TGRSKWRLSYIPFFI
H.sapiens         1  ------------------------------------MVYISNGVVDSRSQSPWRLSLITFF
M.musculus        1  ------------------------------------MVYISNGVVDSRNQSPWRVSFITFF
G.gallus          1  ------------------------------------MVYISNGVVDNRSRAPTSLSAITFF
T.gondii          1  MENEPSAAAPNPWASPGPVNSSSRGRARVINGQIVYGDEVGRPGSQSDARSSRQAVRPGL C.reinhardtii    27  MCWGAISTFFMTMVSPQAVEAYL--KQQVKIVDPPFITGCPRIACVDNIGGGGCSH----
D.melanogaster   26  VGIWFAIKQLFLTFLAPFTGNN----NQANPFRGNGVGGCGWGGGGGGGGGGCGRPGS
D.discoideum     31  WGILNQITFFFSTLIGGTVEPRFRPNNQGGGRRLACFDGIGNVTGCSGVGGSCPSKGPDN
H.sapiens        28  WGIAEFVVLFFKTLLQQDVLRRESYGNSSDSRYDDGRGPDGNPPRFMGRINHLRC-P---
M.musculus       28  WGIAEFVVFFFKTLLQQDVLRREGYGSSSDSRYDDGRGPDGNPPRFMGRISHLRC-P---
G.gallus         28  WSIADFVVMFFQSIIQPDLL-RRGYTSSSYLGQSDGRGPFGNPRRFMGRINHWVGCGP---
T.gondii         61  GVRLCAFIFALVDFVRLFFQTIFSPNYPNQGRGNRQMGGVLSLTPGGGRPDGGGGSG---

C.reinhardtii    82  -----LTEG-----------C----AGGGVG---
D.melanogaster   82  GSGGLRENRRIGRIQPTMSCNMPAGGGVG---
D.discoideum     91  GSNNRRGD-----MKNILACNS-ASGSIGPK
H.sapiens        84  -----SFFP-----------MA-GGVGR-
M.musculus       84  -----SFFP-----------MA-GGVGR-
G.gallus         84  -----SFFP-----------MAGGGVGR-
T.gondii        118  -----SFFRYQQX--------FVCGGGVG---
```

FIGURE 6

```
                                        *
H.sapiens       1  MA---LAVRVVYCGA GYKSKYLQLKKK EDEFP----GR DI CGEGTPQATG FEVM A
M.musculus      1  MA---LAVRVVYCGA GYKPKYLQLKEK EHEFP----GC DI CGEGTPQVTG FEVT A
D.rerio         1  MT---VKV VVYCGG GYRPKF IKLKTL EDEFP----NE EI TGEGTPS TGW EVEVN
C.reinhardtii W1 1 MAP--VQV V YCGG GYGSRYRSLENA RMKFPN---AD KFSFEATPQATG FEVEVN
C.reinhardtii W2 1 MAKTS AAQVVM CGG GYRGRYRSLVEAYRRRFP----LW PTSPTTQRC LEAF SVN
T.gondii        1  MEQT-VE T QF CGG GYRPY DRAEAL RSWLSDAELRR S EGHEDEG TGNFE R N
N.caninum       1  MART-VE T QF CGG GYRPY DRAEAL RSW TDVYFRH S EGHEDEG TGNFE R D H.sapiens       54 GKL I   -KGDGY   TESKFLKLV-AA KAALA G-
M.musculus      54 GKLVHSKK-RGDG VDTESKFRK V-TA K AALA C Q
D.rerio         54 GKLVHSKK-NGDC VDSDSKMQK V-TA EQAMCK--
C.reinhardtii W1 56 GELVHSKK-NGGG VDNQF VER    GEALAK--
C.reinhardtii W2 57 GGLVHSK E-KGMQF PYAPESWSGCT------------
T.gondii        60 GKLVHSKKT KQGF HANKEQQE V RQKL EALGN--
N.caninum       60 GVLVHSKKT RQGF HANKEQQE V RQK REAL DN-
```

FIGURE 7

```
T.gondii    1   MEEALREM HSRLPKADQIQALNLLIKIVNNV    GSANPEELERFRCINSGSTALQQR
N.caninum   1   MEEALQEV QSRLPKADQIQALNLLIKIVTNI    PAATPEEVERFRCINSGSTALQQR T.gondii    61  LLRHGPVYENLLLALGFYRTT PPVSRPLPQENQEYFFLPEHADRACLLADLELLRATVA
N.caninum   61  LLRHGPVYENLLLALGFYRTADPPLSGPLTQANQEYFFLPDHADGCRLLADLELLRATVA T.gondii    121 SLETEGD---DRMPAAERLTSG TGAPRKVTTTSRAIRDSS AAHARNQEELRQLREEQ
N.caninum   121 SLEAEGGNAIESSPTAERLNSA QGAQRKVTTTSRAIRDSS SMHARNQEELRRLREEQ T.gondii    178 RARFEQRSE QATGGITGWLSASLAPSAS SAAQPAQPRHPEPADVPTPGGSRREGSGGN
N.caninum   181 RLRFEQRSE EPAGGIAGWFSSSLAP    PSAQPAG---P------------------

T.gondii    238 AASRFFKSLFGGRSGSRSEEGH GAANRRDRDSRGPRMKTIKDLPPAPQRRG G
N.caninum   219 --S-----LFGSRSGSRSEEGR DGTSQRGGDSRGPRMKTIKDLPPAPRRRG G
```

FIGURE 8

```
H.sapiens     1 --------------------------------------------------MRLL
G.gallus      1 ------------------------------------------------------
C.elegans     1 ---------------------------------MRIHDELQKQDSEFGFLG
O.sativa      1 ----------------------------------------------DRVQLVLLGL
A.thaliana    1 ----------------------------------------------DRTQ
T.gondii      1 MVPSEGAAPSGGG--GAS----------TVSPGTSSPLPSS-----SSTWVAAVSL
N.caninum     1 MAVPQGVVPPGGGDSGGSRGHSVTADATTPPATQTSSPAAPPTSLSSTWVALVSL
C.reinhardtii 1 -----------------------------------------------MQGLKGA H.sapiens      6 LELAASAVRSESANLGGVPSKRLKMQATG----------------------
G.gallus       1 -------------------------MAATG----------------------
C.elegans     23 LFFSVCDLRTEEHSHDENHVHEKDDFEAEFGDETDSQSFSQGTEEDHIEVREQSSFVK
O.sativa      12 PLFCSDLVTLFPEQLPPQPDLPPHPSPDASDAVQP------DDIAADAAASAQIA
A.thaliana    12 FLCSDLFNLFTP---PPPK---SQHQSPPSISETL---------DFPAQKST-----
T.gondii      45 GTLDGLELSGNHAPMQAPSTLVDRFTPHN--------------------
N.caninum        PGTIDGLFSPSENRGSSSASPVLFEQLTPHN--------------------
C.reinhardtii 14 VALFGADEGVMGSKAPQARVQSAMDPDGGLS-----------------------
                                    *

H.sapiens     39 ----------PLKFCICSG---YRRVPEYTEVISQYPDIREGENLEQPIYRH
G.gallus       7 ----------PLFQICSG---YRRVPEYTEVISQYPDIREGENLEQPIYRH
C.elegans     83 PTAHHAKDLPTRFYCSCG---MQAEDQFTTFAKEYPN-PLEGANHAPVLRAY
O.sativa      66 EPQDGPASGTTELKFCASCS---YRGNAVTVKLETSPGHVVLENYPEPFPKRAL
A.thaliana    52 -----GVGYGNTEINFCSCS---YGTAVSMKKMLESVEPGIDVWLANYPAPAPKRIL
T.gondii      79 --PPTGISPHQTQLCTSSSAGALRQLAEFSFQLSELPGFRFVAVEYKESLHQAL
N.caninum     95 --PLPADVGPHQVTQLCTSLSTAGALRQLALESFQLNELPGFRLVADYRESLHQAL
C.reinhardtii 49 --------LGGKHSFQNSGMRGA---EVQVMELARRYPGTEVGTPYPLPAKVPY H.sapiens     86 ASFLSVFKIVLIGLLVGADPFAFE-----------GLQAPSIWQWSQ-ENKVYACMMY
G.gallus      54 ASFLSVFKIVLIGLLVGADPFAFE-----------GLQAPSIWQWSQ-ENKVYACMMY
C.elegans    140 AQALSFVKMALVLVLGGINPEERF-----------GLGYPQILQHSH-GNKMSSCMLV
O.sativa     123 SSAAPFLQVCAYATLMAGDQIEPRS-----------GVVPEPIWYYSLRANRFTRAIT
A.thaliana   104 RVVIPYAQLIGLIMCGEQLFPMI-----------GLAQPPAWYHSLRANRFMSMAST
T.gondii     137 GELIDALISWALLLFVRPICSTLGLTQQRGEERGAQTEQLEPWAEELENNRVAAVWA
N.caninum    153 GELIDVLISWALLLFVRPICEALGLTQ-RGGEGSAQAEQLEPWAEELENNRVTALGSA
C.reinhardtii 98 VAALQVFQFELLGCLAGDKEAAL-----------SAPVEAWYTQNTASNRFEAAMGV H.sapiens    133 FELSNMLENQCMSTGAFEITNDVPVWSKLESGHLPSMQQLVQILNEMKLN----VHMG
G.gallus     101 FELSNMLENQCMSTGAFEITNDVPVWSKLESGHLPSMQQLVQILNEMKLN----VHMG
C.elegans    187 FMLGNLVEQSLMSTGAFELGNEQIWSKLLSGRLPSPQEELVQLLQLAVLGKAPVNTG
O.sativa     170 SLFGNFAQSFLQSEGAFELVCNGQLVFSKLISEQRFPSEFELRELIGNRLPDS----QFGK
A.thaliana   152 GLGNFIQSFLQSFGAFELSCNGELVSKLKEGRFIGEIELRDISSETLTKP----FVTG
T.gondii     197 EEGVLVRSVLIPNNAFEEGENLLWSTLLSGRMPNGRLMQRLETIGVSVR------E
N.caninum    212 FEGFLVRSVLIPSFSFEETFGPNLLWSTIHNGRLPNGRLIRELGLGVRVR------E
C.reinhardtii 146 EGNLVVINQNTGAFELFNGDLIFSKLAEGRVESVPELISPLQLFFEGPAGLHVGGA H.sapiens    189 STPFHRS----------------------
G.gallus     157 SMPFHRS----------------------
C.elegans    247 SFGEFQQTV---------------------
O.sativa     226 NLEFVWS---------------------
A.thaliana   208 SY---------------------
T.gondii     251 PM---------------------
N.caninum    266 PM---------------------
C.reinhardtii 206 GASFPGLTGAGMGHGPELSGVGAAAVGLTG
```

FIGURE 9

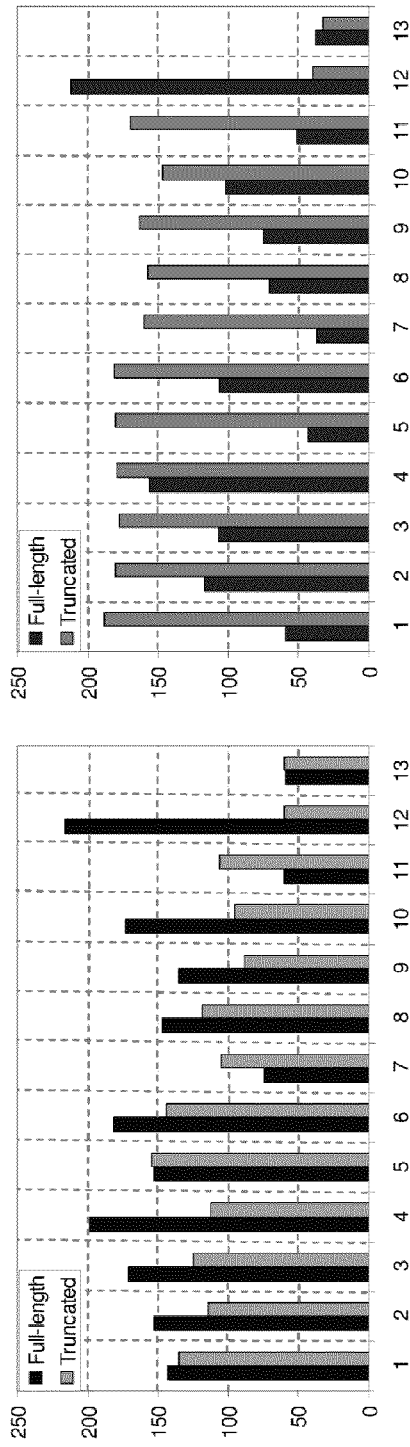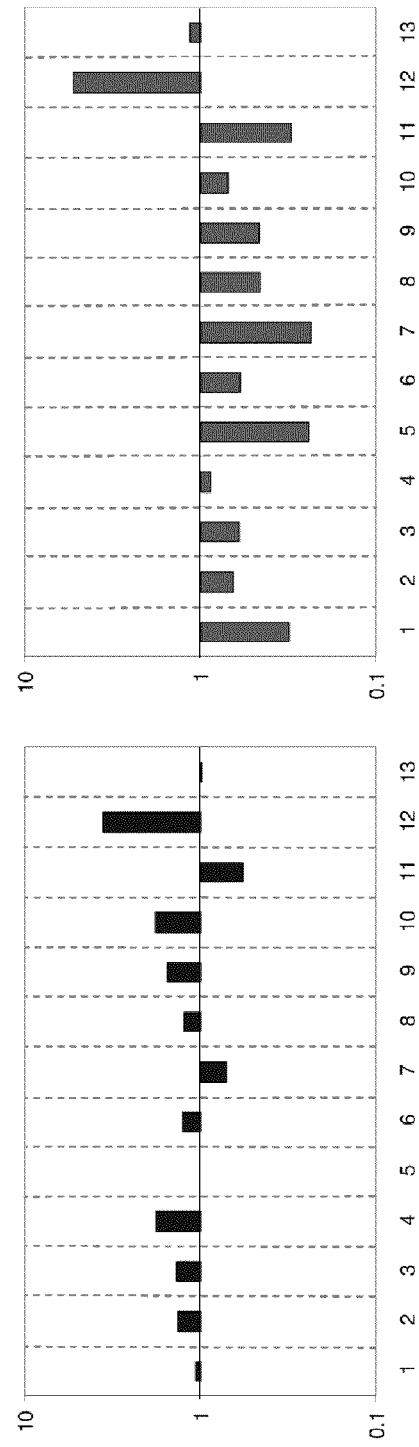
FIGURE 10

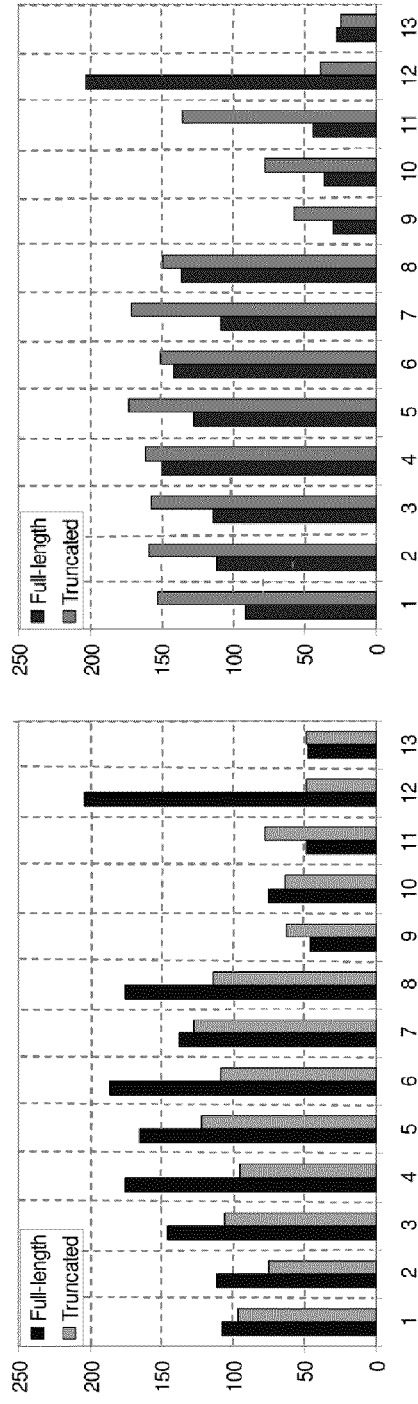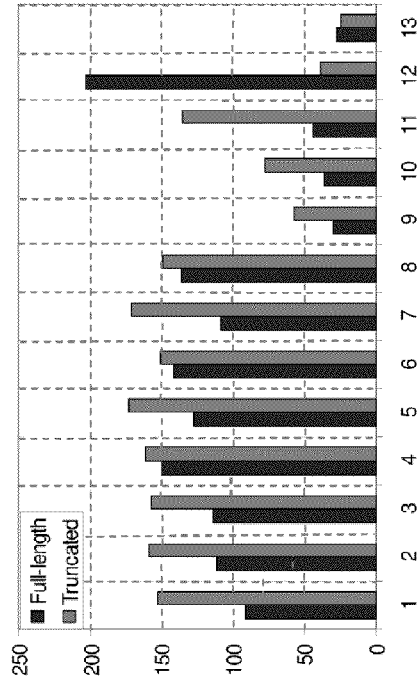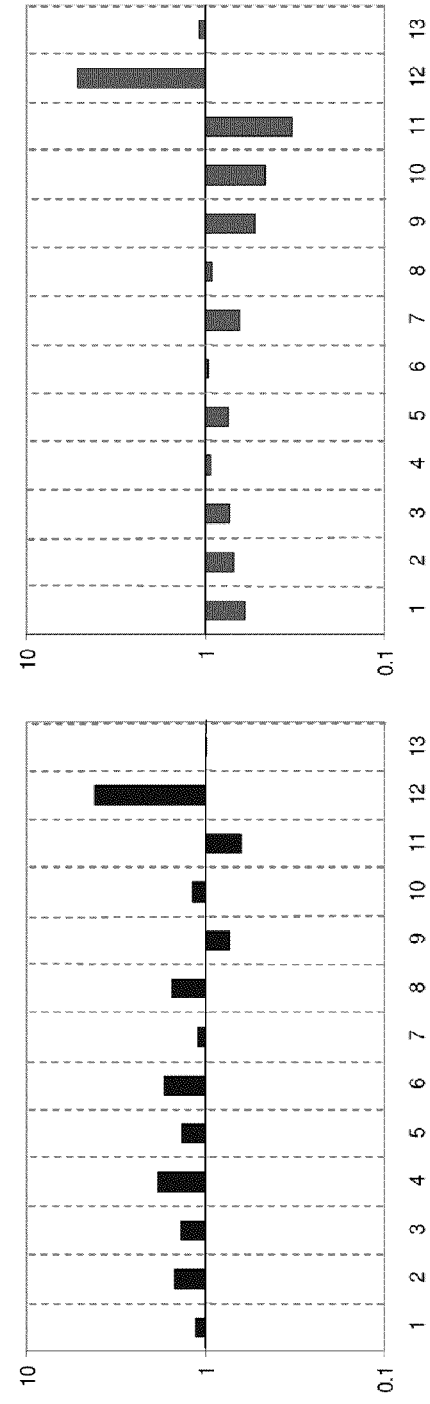
FIGURE 11

|  | Helix I | | Quartet | Helix II | Apical loop | Helix II | Quartet | | Helix I |
|---|---|---|---|---|---|---|---|---|---|
| Human | GGAGAC AGA | A | TGAA | GCGCTCAGCAT | CCCGGGAATACTTCTC | TTGCTGAGAGC | CGAT | GCCC | GTCCCC |
| Mouse | GGAGAC AGA | A | TGAA | GCGCTCAGTAT | CCCGGGAGCATCTCCC | TTGCTGAGGGC | CGAC | GCCA | GTCTCC |
| Rat | GGAGAC AGA | A | TGAA | GCGCTCAGCAT | CCCGGGAGCATAAACTCTC | TTGCTGAGGGC | CGAC | GCCG | GTCTCC |
| Zebrafish | GCGGGACG TTA | A | TGAT | GTCCACAGCTGT | AAAAGCCTGAGA | GCGGCTGCGGAC | TGAT | GATCCGC | GTCCTCGC |

FIGURE 12B

COMPOSITIONS AND METHODS FOR THE EXPRESSION OF SELENOPROTEINS IN EUKARYOTIC CELLS

CROSS REFERENCE TO RELATED APPLICATIONS

This application claims priority to U.S. Provisional Patent Application No. 61/125,822, filed Apr. 29, 2008, and incorporated herein by reference in its entirety.

STATEMENT REGARDING FEDERALLY SPONSORED RESEARCH OR DEVELOPMENT

This invention was made with government support under GM061603 awarded by the National Institutes of Health and with government support under DE-FG07-02ID14380 awarded by the Department of Energy. The government has certain rights in this invention.

INCORPORATION OF SEQUENCE LISTING

A computer readable form of the Sequence Listing is provided herein, contained in the file named "82346_ST25.txt," which is 137826 bytes (as measured in MS-DOS), and is herein incorporated by reference. This Sequence Listing consists of SEQ ID NOs: 1-67.

BACKGROUND

Selenocysteine (Sec)-containing proteins (selenoproteins) are rare but widely distributed in all domains of life (Hatfield and Gladyshev, 2002), including bacteria (Bock et al., 2006; Stadtman, 2002), archaea (Rother et al., 2001) and eukaryotes (Lescure et al., 1999; Castellano et al., 2001; Kryukov et al., 2003). The human genome possesses 25 genes encoding such proteins (Kryukov et al., 2003). Table 1 lists the known human selenoproteins along with disclosed functions and/or non-limiting uses for certain members.

TABLE 1

| Human selenoproteins | Functions |
|---|---|
| Glutathione peroxidase 1 | In blood cells, marker of Se nutrition |
| Glutathione peroxidase 2 | |
| Glutathione peroxidase 3 | Plasma protein, marker of Se status/nutrition |
| Glutathione peroxidase 4 | Essential for male reproduction (sperm maturation) |
| Glutathione peroxidase 6 | |
| Thioredoxin reductase 1 | Target for cancer therapy. Several known classes of anti-cancer drugs target this protein |
| Thioredoxin reductase 2 | |
| Thioredoxin reductase 3 | |
| Deiodinase 1 | Thyroid hormone metabolism |
| Deiodinase 2 | Thyroid hormone metabolism |
| Deiodinase 3 | Thyroid hormone metabolism |
| Methionine-R-sulfoxide reductase | |
| Selenophosphate synthetase 2 | |
| 15-Sep | Has a role in cancer prevention |
| Selenoprotein H | |
| Selenoprotein I | |
| Selenoprotein K | |
| Selenoprotein M | |
| Selenoprotein N | Mutations lead to muscle disorders |
| Selenoprotein O | |
| Selenoprotein P | Major plasma selenoprotein, marker of Se status |
| Selenoprotein S | Role in inflammation |
| Selenoprotein T | |
| Selenoprotein V | |
| Selenoprotein W | |

The class of selenoproteins is defined by the occurrence of Sec, the 21st amino acid encoded by the UGA codon. Selenoproteins utilize the high reactivity of Sec which is located in catalytic centers and serves redox function analogous to the functions of redox-active Cys residues (Johansson et al., 2005). In addition to the UGA codon, a cis-acting element is present within selenoprotein genes, which is also essential for recognition of UGA as the Sec codon. This element is a stem-loop structure known as the selenocysteine insertion sequence (SECIS) and is located in coding regions of bacterial genes and in the 3'-UTRs of archaeal and eukaryotic selenoprotein genes (Berry et al., 1991; Low and Berry, 1996).

One principal feature of previously disclosed eukaryotic SECIS elements is a segment comprising four non-Watson-Crick base pairs 5'-UGAN . . . NGAN-3' referred to as a quartet sequence (Berry et al., 1997; Walczak et al., 1996; Korotkov et al., 2002; Walczak et al., 1998). In previously disclosed eukaryotic SECIS elements, the U residue of the quartet sequence is invariant. Nucleotides comprising the 5'-UGAN . . . NGAN-3' quartet sequence interact with SECIS-binding protein 2 (SBP2) (Copeland et al., 2000; Low et al., 2000) which can form a complex with the Sec-specific elongation factor, known as EFsec, and tRNA$^{[Ser]Sec}$ (Fagegaltier et al., 2000; Tujebajeva et al., 2000). This protein-RNA complex functions by inserting Sec in response to UGA codons in mRNAs containing SECIS elements in the 3'UTR region (Atkins and Gesteland, 2000). Previously disclosed features of SECIS elements include an unpaired residue, usually an A, immediately preceding the 5'-terminus of the aforementioned 5'-UGAN-3' quartet sequence (5'-AUGAN-3') and an unpaired AA or CC motif in a region known as the apical loop. While having low sequence conservation, the secondary structure of eukaryotic SECIS elements is conserved and thermodynamically stable (Martin et al., 1996; Martin et al., 1998). Several algorithms have been developed and successfully applied in genomic searches to identify SECIS stem-loop structures and the associated selenoprotein genes in nucleotide sequence databases (Lescure et al., 1999).

Selenoproteins are notoriously difficult targets for recombinant expression. The bacterial Sec insertion system is different from that in eukaryotes in that the bacterial SECIS is present in the coding region downstream of the Sec codon, whereas the eukaryotic SECIS is in the 3'-UTR. Therefore, expression of recombinant proteins in *E. coli* requires modification of the coding regions of selenoproteins in the vicinity of their active sites. Furthermore, some selenoproteins can only be expressed in eukaryotes due to unique posttranslational modification requirements of those proteins. In both bacterial and eukaryotic systems, efficiency of Sec insertion into recombinant proteins is typically low as the major products are often the truncated forms of selenoproteins. To overcome this problem, several methods for production of recombinant selenoproteins have been proposed (Eckenroth et al., 2006; Su et al., 2005; Arner et al., 1999; Rengby and Arner, 2007). However, there is still a need for compositions and methods that provide for cost-effective, high yield production of recombinant selenoproteins.

SUMMARY OF THE INVENTION

The present invention first provides for a recombinant nucleic acid construct comprising a sequence that encodes a eukaryotic selenocysteine insertion sequence (SECIS) element comprising a 5' proximal 5'-GGAN-3' quartet sequence that is operably linked to both a heterologous expression control sequence and a heterologous sequence comprising a site for operable insertion of a sequence that encodes a heterologous polypeptide. In certain embodiments, the 5' proximal 5'-GGAN-3' quartet sequence is preceded at its immediate 5'-terminus by a G residue. Eukaryotic SECIS elements comprising a native 5' proximal 5'-GGAN-3' can be selected from the group consisting of a *Toxoplasma* SelT SECIS element, a *Toxoplasma* SelS-like SECIS element, a *Neospora* SelT SECIS element, and a *Neospora* SelS-like SECIS element. The eukaryotic SECIS element can also be a chimeric SECIS element wherein a native 5' proximal 5'-UGAN-3' quartet sequence in a canonical eukaryotic SECIS element is replaced by a non-native 5' proximal 5'-GGAN-3' quartet sequence to provide the chimeric SECIS element. In certain embodiments, the native 5' proximal 5'-UGAN-3' quartet sequence is preceded at its immediate 5'-terminus by an A residue and the non-native 5' proximal 5'-GGAN-3' quartet sequence is preceded at its immediate 5'-terminus by a G residue. Canonical eukaryotic SECIS elements that can be used to form a chimeric SECIS element with a 5'-GGAN-3' quartet sequence can be selected from the group consisting of a mammalian SelS SECIS element, a mammalian SelM SECIS element, a mammalian SelH SECIS element, a *Toxoplasma* SelQ SECIS element, a *Toxoplasma* SelW SECIS element, a *Toxoplasma* SelK SECIS element, and a *Neospora* SelW SECIS element.

The recombinant nucleic acid construct can be DNA or the recombinant nucleic acid construct can be RNA. In certain embodiments, the heterologous sequence comprising the site for operable insertion of a heterologous sequence that encodes a heterologous polypeptide comprises at least one restriction endonuclease recognition sequence. The recombinant nucleic acid construct can further comprise a sequence encoding a heterologous polypeptide that contains at least one UGA codon, inserted into the site for operable insertion of a sequence, and a polyadenylation sequence. In certain embodiments, the polypeptide encoded by the sequence encoding a heterologous polypeptide is a selenoprotein. In such a recombinant nucleic acid, the expression control sequence, the sequence encoding a heterologous polypeptide, the sequence encoding the eukaryotic SECIS element, and the polyadenylation sequence are all operably linked. A polypeptide encoded by the heterologous coding sequence can be a selenoprotein.

In certain embodiments, the operably linked expression control sequence, the operably linked heterologous coding sequence, the operably linked sequence encoding a eukaryotic SECIS element, and the operably linked polyadenylation sequence comprise a first expression cassette and the recombinant nucleic acid construct further comprises a second expression cassette. The second expression cassette can encode for the expression of a polypeptide. In certain embodiments, the polypeptide encoded by the second expression cassette is an SBP2 protein.

The present invention also provides for transformed cells comprising a recombinant nucleic acid construct comprising a sequence that encodes a eukaryotic SECIS element comprising a 5' proximal 5'-GGAN-3' quartet sequence that is operably linked to both a heterologous expression control sequence and a heterologous sequence comprising a site for operable insertion of a sequence that encodes a heterologous polypeptide, as well as an organism comprising a recombinant nucleic acid construct comprising a sequence that encodes a eukaryotic SECIS element comprising a 5' proximal 5'-GGAN-3' quartet sequence that is operably linked to both a heterologous expression control sequence and a heterologous sequence comprising a site for operable insertion of a sequence that encodes a heterologous polypeptide.

The present invention also provides for a kit for obtaining a recombinant nucleic acid construct that provides for expression of a selenoprotein; the kit comprising a recombinant nucleic acid construct comprising a sequence that encodes a eukaryotic selenocysteine insertion sequence (SECIS) element comprising a 5' proximal 5'-GGAN-3' quartet sequence that is operably linked to both a heterologous expression control sequence and a heterologous sequence comprising a site for operable insertion of a sequence that encodes a heterologous polypeptide, and instructions for use of the recombinant nucleic acid.

The present invention also provides for a method for obtaining a selenoprotein. The method comprises the steps of: (a) culturing a cell comprising a recombinant nucleic acid construct under conditions permitting expression of a selenoprotein encoded by the recombinant nucleic acid construct, the recombinant nucleic acid construct comprising a sequence that encodes a eukaryotic selenocysteine insertion sequence (SECIS) element comprising a 5' proximal 5'-GGAN-3' quartet sequence that is operably linked to both a heterologous expression control sequence and a heterologous sequence that encodes a heterologous polypeptide containing at least one UGA codon; and (b) recovering the selenoprotein from the cell of step (a) or from a cell culture medium of step (a) thereby obtaining a selenoprotein. In certain embodiments, the 5' proximal 5'-GGAN-3' quartet sequence is preceded at its immediate 5'-terminus by a G residue. In other embodiments, the recombinant nucleic acid comprises a first expression cassette comprising the SECIS element, the heterologous expression control sequence, and the heterologous sequence that encodes a heterologous polypeptide; and a second expression cassette that encodes a second polypeptide. In certain embodiments, the second polypeptide is an SBP2 protein.

The present invention further provides for a recombinant nucleic acid construct comprising a sequence that encodes a chimeric eukaryotic selenocysteine insertion sequence (SECIS) element that is operably linked to both a heterologous expression control sequence and a heterologous sequence comprising a site for operable insertion of a heterologous sequence that encodes a heterologous polypeptide, wherein a native 5' proximal 5'-GGAN-3' quartet sequence in a non-canonical SECIS element is replaced by a non-native 5' proximal 5'-UGAN-3' quartet sequence to provide the chimeric SECIS element. In certain embodiments, the native 5' proximal 5'-GGAN-3' quartet sequence is preceded at its immediate 5'-terminus by a G residue and the non-native 5' proximal 5'-UGAN-3' quartet sequence is preceded at its immediate 5'-terminus by an A residue. Non-canonical SECIS elements that can be used to form a chimeric SECIS element with a 5'-UGAN-3' quartet sequence can be selected from the group consisting of a *Toxoplasma* SelT SECIS element, a *Toxoplasma* SelS-like SECIS element, a *Neospora* SelT SECIS element, and a *Neospora* SelS-like SECIS element.

The recombinant nucleic acid construct can be DNA or the recombinant nucleic acid construct can be RNA. In certain embodiments, the site for operable insertion of a heterologous sequence that encodes a heterologous polypeptide comprises at least one restriction endonuclease recognition sequence.

The recombinant nucleic acid construct can further comprise a heterologous coding sequence that contains at least one UGA codon inserted into the site for operable insertion of a heterologous sequence that encodes a heterologous polypeptide, and a polyadenylation sequence, where the expression control sequence, the heterologous coding sequence, the sequence encoding the eukaryotic SECIS element, and the polyadenylation sequence are all operably linked. In certain embodiments, the polypeptide encoded by the heterologous coding sequence can be a selenoprotein.

In certain embodiments, the operably linked expression control sequence, the heterologous sequence that encodes a heterologous polypeptide, the sequence encoding a eukaryotic SECIS element, and the polyadenylation sequence comprise a first expression cassette and the recombinant nucleic acid construct further comprises a second expression cassette. The second expression cassette can encode for the expression of a second polypeptide. In certain embodiments, the second polypeptide is an SBP2 protein.

The present invention also provides for a transformed cell comprising a recombinant nucleic acid construct comprising a sequence that encodes a chimeric eukaryotic SECIS element comprising a 5' proximal 5'-UGAN-3' quartet sequence that is operably linked to both a heterologous expression control sequence and a heterologous sequence comprising a site for operable insertion of a sequence that encodes a heterologous polypeptide, as well as an organism comprising a recombinant nucleic acid construct comprising a sequence that encodes a chimeric SECIS element comprising a 5' proximal 5'-UGAN-3' quartet sequence that is operably linked to both a heterologous expression control sequence and a heterologous sequence comprising a site for operable insertion of a sequence that encodes a heterologous polypeptide.

The present invention also provides for a kit for obtaining a recombinant nucleic acid construct that provides for expression of a selenoprotein; the kit comprising a recombinant nucleic acid construct comprising a sequence that encodes a chimeric eukaryotic SECIS element comprising a 5' proximal 5'-UGAN-3' quartet sequence that is operably linked to both a heterologous expression control sequence and a heterologous sequence comprising a site for operable insertion of a sequence that encodes a heterologous polypeptide, and instructions for the use of said recombinant nucleic acid.

The present invention also provides for a method for obtaining a selenoprotein. The method comprises the steps of: (a) culturing a cell comprising a recombinant nucleic acid construct under conditions permitting expression of a selenoprotein encoded by said recombinant nucleic acid construct, the recombinant nucleic acid construct comprising a sequence that encodes a chimeric selenocysteine insertion sequence (SECIS) element that is operably linked to both a heterologous expression control sequence and a heterologous sequence that encodes a heterologous polypeptide and contains at least one UGA codon, wherein a native 5' proximal 5'-GGAN-3' quartet sequence in a non-canonical SECIS element is replaced by a non-native 5' proximal 5'-UGAN-3' quartet sequence to provide said chimeric SECIS element; and (b) recovering the selenoprotein from said cell of step (a) or from a cell culture medium of step (a) thereby obtaining a selenoprotein. In certain embodiments, the native 5' proximal 5'-GGAN-3' quartet sequence is immediately preceded by an G residue and the non-native 5' proximal 5'-UGAN-3' quartet sequence is immediately preceded by an A residue. In certain embodiments, the recombinant nucleic acid construct comprises a first expression cassette comprising a chimeric SECIS element and a heterologous sequences and a second expression cassette that encodes a second polypeptide. In certain embodiments, the second polypeptide is an SBP2 protein.

The present invention also provides for an isolated nucleic acid comprising a heterologous coding sequence operably linked to a sequence that encodes a eukaryotic selenocysteine insertion sequence (SECIS) element wherein the SECIS element comprises a 5' proximal 5'-GGAN-3' quartet sequence. In certain embodiments the 5' proximal 5'-GGAN-3' quartet sequence is preceded at its immediate 5'-terminus by a G residue. Eukaryotic SECIS elements comprising a native 5' proximal 5'-GGAN-3' quartet sequence can be selected from the group consisting of a *Toxoplasma* SelT SECIS element, a *Toxoplasma* SelS-like SECIS element, a *Neospora* SelT SECIS element, and a *Neospora* SelS-like SECIS element. The SECIS element can also be a chimeric SECIS element wherein a native 5' proximal 5'-UGAN-3' quartet sequence in a canonical eukaryotic SECIS element is replaced by a non-native 5' proximal 5'-GGAN-3' quartet sequence to provide said chimeric SECIS element. In certain embodiments, the native 5' proximal 5'-UGAN-3' quartet sequence is preceded at its immediate 5'-terminus by an A residue and the non-native 5' proximal 5'-GGAN-3' quartet sequence is preceded at its immediate 5'-terminus by a G residue. Canonical eukaryotic SECIS elements that can be used to form a chimeric SECIS element with a 5'-GGAN-3' quartet sequence can be selected from the group consisting of a mammalian SelS SECIS element, a mammalian SelM SECIS element, a mammalian SelH SECIS element, a *Toxoplasma* SelQ SECIS element, a *Toxoplasma* SelW SECIS element, a *Toxoplasma* SelK SECIS element, and a *Neospora* SelW SECIS element.

The present invention also provides for an isolated nucleic acid comprising a heterologous coding sequence operably linked to a sequence that encodes a chimeric eukaryotic selenocysteine insertion sequence (SECIS) element, wherein a native 5' proximal 5'-GGAN-3' quartet sequence in a non-canonical SECIS element is replaced by a non-native 5' proximal 5'-UGAN-3' quartet sequence to provide said chimeric SECIS element. In certain embodiments, the native 5' proximal 5'-GGAN-3' quartet sequence is preceded at its immediate 5'-terminus by a G residue and the non-native 5' proximal 5'-UGAN-3' quartet sequence is preceded at its immediate 5'-terminus by an A residue. Non-canonical SECIS elements can be selected from the group consisting of a *Toxoplasma* SelT SECIS element, a *Toxoplasma* SelS-like SECIS element, a *Neospora* SelT SECIS element, and a *Neospora* SelS-like SECIS element.

BRIEF DESCRIPTION OF THE DRAWINGS

FIG. 1A shows SECIS elements identified in *Toxoplasma* and *Neospora*. Canonical (5' proximal 5'-UGAN-3' quartet region; shown in white background) and non-canonical (5' proximal 5'-GGAN-3' quartet region; shown in grey background) SECIS elements identified in *Toxoplasma* and *Neospora* are shown. (*Toxoplasma* SelQ SECIS element (SEQ ID NO: 1); *Toxoplasma* SelW SECIS element (SEQ ID NO: 2); *Toxoplasma* SelK SECIS element (SEQ ID NO: 3); *Toxoplasma* SelT SECIS element (SEQ ID NO: 4); *Toxo-* plasma SelS-like SECIS element (SEQ ID NO: 5); *Neospora* SelW SECIS element (SEQ ID NO: 6); *Neospora* SelT SECIS element (SEQ ID NO: 7); *Neospora* SelS-like SECIS element (SEQ ID NO: 8). The SECIS quartet region with its immediate 5'-terminus preceding residue and the unpaired AA nucleotides in the apical loop are shown in bold.

FIG. 1B shows *Toxoplasma* Selenoprotein Q (SelQ). The SelQ nucleotide sequence is provided as SEQ ID NO: 53 and the SelQ amino acid sequence is provided as SEQ ID NO: 54. EST sequences (GenBank accession numbers CN615432.1 and CF268978.1) were used for sequence reconstruction. Locations of the initiator AUG codon, Sec-encoding UGA codon, stop signal, and the SECIS element are indicated.

FIG. 2A shows a scheme illustrating GFP-fusion constructs and cloning strategies. Predicted sizes of GFP-mSelH fusion proteins are displayed at the top. Mouse SelH—*Toxoplasma* SECIS chimeras were generated by cloning the corresponding forms of *Toxoplasma* sequences immediately downstream of the mouse SelH stop codon (into construct 2 in the scheme). Distances between stop codons and SECIS elements for native mouse SelH and *Toxoplasma* SelT and SelS-like SECIS elements are shown. Short versions of fusions were designated as "SECIS", and long as "3'UTR".

FIG. 2B shows HEK 293 cells transfected with the constructs shown in panel FIG. 2A or co-transfected with an SBP2 expression construct as indicated:

lanes 1-2 correspond to construct 3 (in the scheme in panel A) (GFP-mSelH-*Toxoplasma* SelT 5' proximal 5'-GGAN-3' quartet sequence preceded immediately at its 5'-terminus by a G residue (5'-GGGAN-3')-type SECIS);

lanes 3-4 correspond to construct 4 (GFP-mSelH-*Toxoplasma* SelT 5' proximal 5'-GGAN-3' quartet sequence preceded immediately at its 5'-terminus by a G residue (5'-GGGAN-3')-type 3'UTR);

lanes 5-6 correspond to construct 5 (GFP-mSelH-*Toxoplasma* SelS-like 5' proximal 5'-GGAN-3' quartet sequence preceded immediately at its 5'-terminus by a G residue (5'-GGGAN-3')-type SECIS);

lanes 7-8 correspond to construct 6 (GFP-mSelH-*Toxoplasma* SelS-like 5' proximal 5'-GGAN-3' quartet sequence preceded immediately at its 5'-terminus by a G residue (5'-GGGAN-3')-type 3'UTR);

lanes 9-10 correspond to construct 1 (GFP-mSelH);
lane 11 corresponds to construct 2 (GFP-mSelHΔSECIS);
lane 12 corresponds to GFP-mSelHSec>Cys; and lane 13 correspond to GFP (control).

Cells were labeled with [75]Se. Upper panels represent selenoprotein patterns on SDS-PAGE gels. Migration of major endogenous selenoproteins, thioredoxin reductase 1 (TR1), and glutathione peroxidase 1 (GPx1) is shown on the right. Lower panels show western blots of the same samples probed with GFP antibodies. The bands corresponding to GFP-SelH fusions are indicated on the left and their sizes on the right.

FIG. 2C shows NIH 3T3 cells transfected with the constructs shown in panel A or co-transfected with an expression SBP2 construct as indicated:

lanes 1-2 correspond to construct 3 (in the scheme in panel A) (GFP-mSelH-*Toxoplasma* SelT 5' proximal 5'-GGAN-3' quartet sequence preceded immediately at its 5'-terminus by a G residue (5'-GGGAN-3')-type SECIS);

lanes 3-4 correspond to construct 4 (GFP-mSelH-*Toxoplasma* SelT 5' proximal 5'-GGAN-3' quartet sequence preceded immediately at its 5'-terminus by a G residue (5'-GGGAN-3')-type 3'UTR);

lanes 5-6 correspond to construct 5 (GFP-mSelH-*Toxoplasma* SelS 5' proximal 5'-GGAN-3' quartet sequence preceded immediately at its 5'-terminus by a G residue (5'-GGGAN-3')-type SECIS);

lanes 7-8 correspond to construct 6 (GFP-mSelH-*Toxoplasma* SelS 5' proximal 5'-GGAN-3' quartet sequence preceded immediately at its 5'-terminus by a G residue (5'-GGGAN-3')-type 3'UTR);

lanes 9-10 correspond to construct 1 (GFP-mSelH);
lane 11 corresponds to construct 2 (GFP-mSelHΔSECIS);
lane 12 corresponds to GFP-mSelHSec>Cys; and lane 13 correspond to GFP (control).

Cells were labeled with [75]Se. Upper panels represent selenoprotein patterns on SDS-PAGE gels. Migration of major endogenous selenoproteins, thioredoxin reductase 1 (TR1), and glutathione peroxidase 1 (GPx1) is shown on the right. Lower panels show western blots of the same samples probed with GFP antibodies. The bands corresponding to GFP-SelH fusions are indicated on the left and their sizes on the right.

FIG. 3A shows mammalian SECIS elements used in the study that represent three known types of eukaryotic SECIS elements. From left to right: Mouse SelH SECIS element (SEQ ID NO:9); mouse SelM SECIS element (SEQ ID NO: 10); and mouse SelS SECIS element (SEQ ID NO: 11). Changes made to generate the chimeric SECIS elements (5'-AUGAN-3' changed to 5'-GGGAN-3') are shown: Chimeric mouse SelH SECIS element (SEQ ID NO: 12); chimeric mouse SelM SECIS element (SEQ ID NO: 13); chimeric mouse SelS SECIS element (SEQ ID NO: 14).

FIG. 3B shows HEK 293 cells transfected with the following constructs:

lane 1, GFP-mSelM (wild type); lane 2, GFP-mSelM (wild type)+SBP2;

lane 3, GFP-mSelM 5' proximal 5'-TGAN-3' quartet sequence preceded immediately at its 5'-terminus by an A residue (5'-ATGAN-3') changed to 5' proximal 5'-GGAN-3' quartet sequence preceded immediately at its 5'-terminus by a G residue (5'-GGGAN-3') chimeric SECIS element;

lane 4, GFP-mSelM 5' proximal 5'-TGAN-3' quartet sequence preceded immediately at its 5'-terminus by an A residue (5'-ATGAN-3') changed to 5' proximal 5'-GGAN-3' quartet sequence preceded immediately at its 5'-terminus by a G residue (5'-GGGAN-3') chimeric SECIS element+SBP2;

lane 5, GFP (control); lane 6, GFP-mSelS (wild type); lane 7, GFP-mSelS (wild type)+SBP2;

lane 8, GFP-mSelS 5' proximal 5'-TGAN-3' quartet sequence preceded immediately at its 5'-terminus by an A residue (5'-ATGAN-3') changed to 5' proximal 5'-GGAN-3' quartet sequence preceded immediately at its 5'-terminus by a G residue (5'-GGGAN-3') chimeric SECIS element;

lane 9, GFP-mSelS 5' proximal 5'-TGAN-3' quartet sequence preceded immediately at its 5'-terminus by an A residue (5'-ATGAN-3') changed to 5' proximal 5'-GGAN-3' quartet sequence preceded immediately at its 5'-terminus by a G residue (5'-GGGAN-3') chimeric SECIS element+SBP2; and lane 10, GFP (control).

Cells were labeled with [75]Se. Migration of proteins expressed from the constructs and major endogenous selenoproteins are indicated.

FIG. 3C shows NIH 3T3 cells transfected with the following constructs:

lane 1, GFP-mSelM (wild type); lane 2, GFP-mSelM (wild type)+SBP2;

lane 3, GFP-mSelM 5' proximal 5'-TGAN-3' quartet sequence preceded immediately at its 5'-terminus by an A residue (5'-ATGAN-3') changed to 5' proximal 5'-GGAN-3' quartet sequence preceded immediately at its 5'-terminus by a G residue (5'-GGGAN-3') chimeric SECIS element;

lane 4, GFP-mSelM 5' proximal 5'-TGAN-3' quartet sequence preceded immediately at its 5'-terminus by an A residue (5'-ATGAN-3') changed to 5' proximal 5'-GGAN-3' quartet sequence preceded immediately at its 5'-terminus by a G residue (5'-GGGAN-3') chimeric SECIS element+SBP2;

lane 5, GFP (control); lane 6, GFP-mSelS (wild type); lane 7, GFP-mSelS (wild type)+SBP2;

lane 8, GFP-mSelS 5' proximal 5'-TGAN-3' quartet sequence preceded immediately at its 5'-terminus by an A residue (5'-ATGAN-3') changed to 5' proximal 5'-GGAN-3' quartet sequence preceded immediately at its 5'-terminus by a G residue (5'-GGGAN-3') chimeric SECIS element;

lane 9, GFP-mSelS 5' proximal 5'-TGAN-3' quartet region preceded immediately at its 5'-terminus by an A residue (5'-ATGAN-3') changed to 5' proximal 5'-GGAN-3'quartet region preceded immediately at its 5'-terminus by a G residue (5'-GGGAN-3') chimeric SECIS element+SBP2; and lane 10, GFP (control).

Cells were labeled with $^{75}$Se. Migration of proteins expressed from the constructs and major endogenous selenoproteins are indicated.

FIG. 4A shows HEK 293 cells transfected with the following constructs:

(Chimeric *Toxoplasma* SelT SECIS element (SEQ ID NO: 15); chimeric *Toxoplasma* SelS-like SECIS element (SEQ ID NO: 16)).

lane 1, GFP-mSelH-*Toxoplasma* SelT 5' proximal 5'-GGAN-3' quartet sequence preceded immediately at its 5'-terminus by an G residue (5'-GGGAN-3') changed to 5∝proximal 5'-TGAN-3' quartet sequence preceded immediately at its 5'-terminus by an A residue (5'-ATGAN-3') chimeric SECIS element;

lane 2, GFP-mSelH-*Toxoplasma* SelT 5' proximal 5'-GGAN-3' quartet sequence preceded immediately at its 5'-terminus by an G residue (5'-GGGAN-3') changed to 5∝proximal 5'-TGAN-3' quartet sequence preceded immediately at its 5'-terminus by an A residue (5'-ATGAN-3') chimeric SECIS element+SBP2;

lane 3, GFP-mSelH-*Toxoplasma* SelT 5' proximal 5'-GGAN-3' quartet sequence preceded immediately at its 5'-terminus by an G residue (5'-GGGAN-3') changed to 5∝proximal 5'-TGAN-3' quartet sequence preceded immediately at its 5'-terminus by an A residue (5'-ATGAN-3') chimeric SECIS element (3' UTR construct);

lane 4, GFP-mSelH-*Toxoplasma* SelT 5' proximal 5'-GGAN-3' quartet sequence preceded immediately at its 5'-terminus by an G residue (5'-GGGAN-3') changed to 5∝proximal 5'-TGAN-3' quartet sequence preceded immediately at its 5'-terminus by an A residue (5'-ATGAN-3') chimeric SECIS element (3' UTR construct)+SBP2;

lane 5, GFP-mSelH-*Toxoplasma* SelS-like 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element;

lane 6, GFP-mSelH-*Toxoplasma* SelS-like 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element+SBP2;

lane 7, GFP-mSelH-*Toxoplasma* SelS-like 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element (3' UTR construct);

lane 8, GFP-mSelH-*Toxoplasma* SelS-like 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element (3' UTR construct)+SBP2;

lane 9, GFP-mSelH (wild type); lane 10, GFP-mSelH (wild type)+SBP2;

lane 11, GFP-mSelHΔSECIS; lane 12, GFP-mSelH Sec>Cys; and lane 13, GFP (control).

Upper panels represent selenoprotein patterns based on metabolic labeling of cells with $^{75}$Se. Lower panels show western blots developed with anti-GFP antibodies.

FIG. 4B shows NIH 3T3 cells transfected with the following constructs:

(Chimeric *Toxoplasma* SelT SECIS element (SEQ ID NO: 15); chimeric *Toxoplasma* SelS-like SECIS element (SEQ ID NO: 16)).

lane 1, GFP-mSelH-*Toxoplasma* SelT 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element;

lane 2, GFP-mSelH-*Toxoplasma* SelT 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element+SBP2;

lane 3, GFP-mSelH-*Toxoplasma* SelT 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element (3' UTR construct);

lane 4, GFP-mSelH-*Toxoplasma* SelT 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element (3' UTR construct)+SBP2;

lane 5, GFP-mSelH-*Toxoplasma* SelS-like 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element;

lane 6, GFP-mSelH-*Toxoplasma* SelS-like 5' proximal 5'-GGAN-3' quartet sequence preceded immediately at its 5'-terminus by an G residue (5'-GGGAN-3') changed to 5∝proximal 5'-TGAN-3' quartet sequence preceded immediately at its 5'-terminus by an A residue (5'-ATGAN-3') chimeric SECIS element+SBP2;

lane 7, GFP-mSelH-*Toxoplasma* SelS-like 5' proximal 5'-GGAN-3' quartet sequence preceded immediately at its 5'-terminus by an G residue (5'-GGGAN-3') changed to 5∝proximal 5'-TGAN-3' quartet sequence preceded immediately at its 5'-terminus by an A residue (5'-ATGAN-3') chimeric SECIS element (3' UTR construct);

lane 8, GFP-mSelH-*Toxoplasma* SelS-like 5' proximal 5'-GGAN-3' quartet sequence preceded immediately at its 5'-terminus by an G residue (5'-GGGAN-3') changed to 5' proximal 5'-TGAN-3' quartet sequence preceded immediately at its 5'-terminus by an A residue (5'-ATGAN-3') chimeric SECIS element (3' UTR construct)+SBP2;

lane 9, GFP-mSelH (wild type); lane 10, GFP-mSelH (wild type)+SBP2;

lane 11, GFP-mSelHΔSECIS; lane 12, GFP-mSelH Sec>Cys; and lane 13, GFP (control).

Upper panels represent selenoprotein patterns based on metabolic labeling of cells with $^{75}$Se. Lower panels show western blots developed with anti-GFP antibodies.

FIG. 5A shows a vector map of the selenoprotein expression vector pSelExpress1 (SEQ ID NO: 18). A chimeric *Toxoplasma* SelT SECIS element is preceded by multiple cloning site (MCS) and by human cytomegalovirus (CMV) immediate-early promoter. The C-terminal portion of rat SBP2 is under human EF-1α promoter. Other major features of the vector backbone are indicated.

FIG. 5B shows expression and enrichment of recombinant His-tagged GPx1 on metal-affinity resin. HEK 293 cells were transfected with GPx1-pBudCE4.1 (lane 1), GPx1-pBudCE4.1 co-transfected with SBP2 (lane 3), GPx1-pSelExpress1 (lane 5) or with pBudCE4.1 as control (lane 7). Cell lysates were prepared as described in Example 13, and GPx1 was enriched from each sample on TALON resin. Proteins bound to the resin were loaded in lanes 2, 4, 6 and 8 as shown in the figure. The upper panel shows metabolic labeling of cells with $^{75}$Se, the middle panel western blot with anti-GPx1 antibodies, and the lower panel protein staining with Amido Black. Since GPx1 is a tetramer, the His-tagged GPx1 expressed from pSelExpress1 binds the endogenous GPx1 (21 kDa band), which is then also enriched on TALON resin (see lower bands in lanes 2, 4 and 6, but not in 8).

FIG. 6 shows multiple sequence alignments of apicomplexan selenoprotein SelK. Sequences with the following accession numbers were used in the alignment: TgEST__95058496 (*T. gondii*) (SEQ ID NO: 29), AAH13162.2 (*H. sapiens*) (SEQ ID NO: 30), Q9JLJ1 (*M. musculus*) (SEQ ID NO: 31), NP__001020612.1 (*G. gallus*) (SEQ ID NO: 32), AAN32902.1 (*C. reinhardtii*) (SEQ ID NO: 33), XP__646897.1 (*D. discoideum*) (SEQ ID NO 34), and NP__572763.3 (*D. melanogaster*) (SEQ ID NO 35). Selenocysteine residues (U) are indicated by asterisk.

FIG. 7 shows multiple sequence alignments of apicomplexan selenoprotein SelW. The alignment is based on the following sequences: NP__003000.1 (*H. sapiens*) (SEQ ID NO: 36), NP__033182.1 (M. musculus) (SEQ ID NO: 37), AAO86696.1 (*D. rerio*) (SEQ ID NO: 38), BU654801.1 and BP092691.1 (*C. reinhardtii*) (SEQ ID NO: 39 and SEQ ID NO: 40 respectively), TgEST__95057361 (*T. gondii*) (SEQ ID NO: 41), and TC2958 (*N. caninum*) (SEQ ID NO: 42). Selenocysteine residues (U) are indicated by asterisk.

FIG. 8 shows multiple sequence alignments of apicomplexan selenoprotein SelS-like. The following sequences were used in the alignment: TgTwinScan__4798 (*T. gondii*) (SEQ ID NO: 43) and TC3699 and TC3703 (*N. caninum*) (SEQ ID NO: 44). Selenocysteine residues (U) are indicated by asterisk.

FIG. 9 shows multiple sequence alignments of apicomplexan selenoprotein SelT. Accession numbers of the sequences are as follows: AAH26350.2 (*H. sapiens*) (SEQ ID NO: 45), NP__001006557.2 (*G. gallus*) (SEQ ID NO: 46), CAB01684.1 (*C. elegans*) (SEQ ID NO: 47), NP__915340.1 (*O. sativa*) (SEQ ID NO: 48), BAD43801.1 (*A. thaliana*) (SEQ ID NO: 49), BQ818029.1 (*C. reinhardtii*) (SEQ ID NO: 50), TgESTzyi41b04.y1 and TgESTzyd07e11.y1 (*T. gondii*) (SEQ ID NO: 51), and TC2223 and TC1872 (*N. caninum*) (SEQ ID NO: 52). Selenocysteine residues (U) are indicated by asterisk.

FIG. 10 shows an evaluation of band intensities in the Western blots in FIG. 2. Quantification of bands for HEK 293 (left column) and NIH 3T3 (right column) cells is shown in absolute values for each lane, Logarithmic scale is used for representation of intensity ratio of full-length and truncated forms of proteins (Lower). Numbering is the same as in FIG. 2. Scion Image 4.0 software (Scion Corporation) was used for image processing and analysis.

FIG. 11 shows an evaluation of band intensities in the Western blots in FIG. 4. Quantification of bands for HEK 293 (left column) and NIH 3T3 (right column) cells is shown in absolute values for each lane. Logarithmic scale is used for representation of intensity ratio of full-length and truncated forms of proteins (Lower). Numbering is the same as in FIG. 4. Scion Image 4.0 software (Scion Corporation) was used for image processing and analysis.

FIG. 12A shows a eukaryotic SECIS element consensus structure. The locations of structural features in the stem-loop (Helix I, internal loop, quartet sequence, Helix II, and apical loop) are indicated. N indicates any base.

FIG. 12B shows an alignment of the SECIS elements of the human (SEQ ID NO: 55), mouse (SEQ ID NO: 56), rat (SEQ ID NO: 57), and zebra fish (SEQ ID NO: 58), SelM-encoding genes. Locations of structural features in SECIS elements are indicated. The 5' proximal quartet sequence (left side) and the 3' proximal quartet sequence (right side) are boxed.

Figure 15:
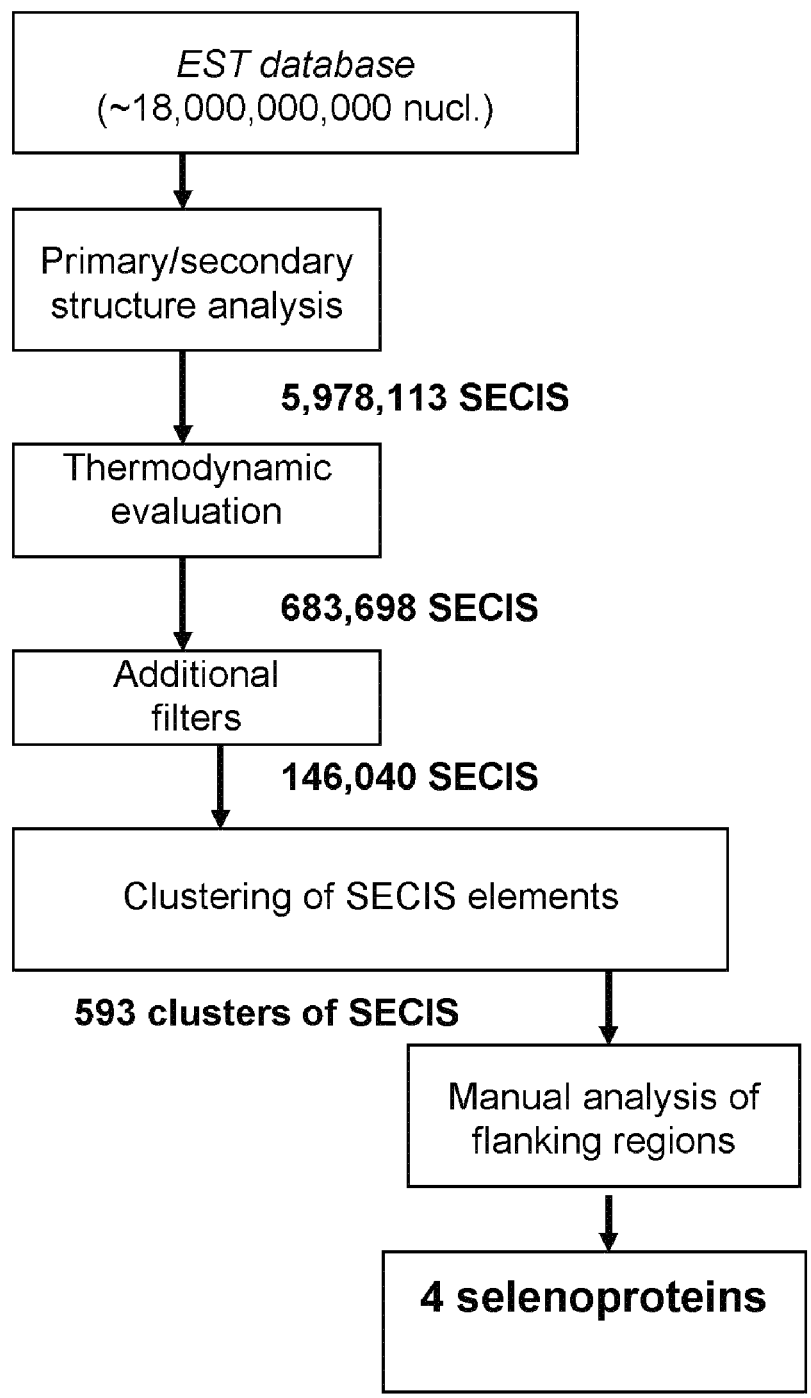

FIG. 15 shows an analysis of NCBI EST database. SECIS candidates identified in each step are indicated. Only SelT and SelS from *T. gondii* and *N. caninum* were identified in this search.

DETAILED DESCRIPTION

Novel SECIS elements, recombinant nucleic acids comprising the novel SECIS elements, and their use in methods for production of recombinant selenoproteins are provided herein.

I. Definitions

Unless otherwise defined, all technical and scientific terms used herein have the same meaning as commonly understood by one of ordinary skill in the art to which this invention pertains.

The phrase "canonical SECIS element" as used herein refers to a eukaryotic SECIS element comprising a 5' proximal 5'-UGAN-3' quartet sequence. Reference to a "canonical 5' proximal quartet sequence" refers to a 5' proximal quartet sequence comprising the nucleotide sequence 5'-UGAN-3' when referring to the sequence of canonical SECIS element ribonucleic acid (RNA), and to the nucleotide sequence 5'-TGAN-3' when referring to a DNA molecule that encodes a canonical SECIS element.

The phrase "non-canonical SECIS element" as used herein refers to a eukaryotic SECIS element comprising a 5' proximal 5'-GGAN-3' quartet sequence.

The phrase "chimeric SECIS element" as used herein refers to a eukaryotic SECIS element wherein the native sequence of the 5' proximal quartet sequence of the SECIS element has been substituted with a non-native 5' proximal quartet sequence. A chimeric SECIS element can comprise either the substitution of a canonical quartet sequence with a non-canonical quartet sequence or alternatively, the substitution of a non-canonical quartet sequence with a canonical sequence.

The term "coding sequence" as used herein refers to a nucleic acid sequence that is transcribed and translated into a polypeptide when placed under the control of appropriate regulatory or expression control sequences.

The term "encode" as used herein refers to the capacity of a nucleic acid to provide another nucleic acid or a polypeptide. A nucleic acid sequence or construct is said to "encode" a polypeptide if it can be transcribed and/or translated to produce the polypeptide. A nucleic acid sequence or construct is said to "encode" a eukaryotic SECIS element if it can be transcribed to produce an RNA that comprises the SECIS element.

The phrase "expression control sequence" as used herein refers to nucleic acid sequences that control transcription, post-transcriptional events, and translation of operably linked nucleic acid sequences.

The phrase "expression cassette" as used herein refers to a defined segment of a nucleic acid molecule that comprises the minimum elements needed for production of another nucleic acid or protein encoded by that nucleic acid molecule.

The phrase "expression vector" refers to a nucleic acid construct, generated recombinantly or synthetically, that provides for production of a nucleic acid sequence either in vitro or in vivo.

The phrase "5' proximal quartet sequence" as used herein refers to the four nucleotide sequence of the strand of the quartet element that is located closest to the 5' terminus of the SECIS element as read from its 5' terminus to its 3' terminus.

The term "heterologous" as used herein in reference to operably linked portions of a recombinant nucleic acid indicates that the indicated portions are not operably linked in nature.

The term "native" as used herein refers to the naturally occurring form of a composition. In regards to the present invention, a native SECIS element can thus comprise a canonical or non-canonical sequence depending on its origin.

The organism "*Neospora*" as referred to herein refers to any specie of the genus of the apicomplexan organism *Neospora*.

The term "nucleic acid" as used herein refers to deoxyribonucleotides or ribonucleotides and polymers thereof such as, for example but not limited to, DNA molecules and RNA molecules.

The phrase "operable insertion" as used herein refers to the insertion of one or more additional nucleic acid sequences into a nucleic acid construct so that the additional sequence(s) are operably linked to at least one other sequence in the construct.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter is linked such that the resulting translation product is in frame with the translational open reading frame that encodes the protein desired. Nucleic acid sequences that can be operably linked include, but are not limited to, sequences that provide gene expression functions (i.e., gene expression elements such as promoters, 5' untranslated regions, introns, protein coding regions, 3' untranslated regions, SECIS elements, polyadenylation sites, and/or transcriptional terminators), sequences that provide DNA transfer and/or integration functions (i.e., site specific recombinase recognition sites, integrase recognition sites), sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences, homologous recombination sequences), and sequences that provide replication functions (i.e., bacterial origins of replication, autonomous replication sequences, centromeric sequences).

The terms "polypeptide," "peptide," and "protein" are used interchangeably herein to refer to a polymer comprising at least two amino acids.

The term "promoter" as used herein refers to a nucleic acid sequence or an array of nucleic acid sequences that directs transcription of a nucleic acid.

The term "recombinant" as used herein refers to a nucleic acid synthesized or otherwise manipulated in vitro (for example, recombinant nucleic acid), to methods of using recombinant nucleic acids to produce gene products either in vivo or in vitro, and/or to a polypeptide produced by a recombinant nucleic acid.

The phrase "recombinant nucleic acid" or "recombinant nucleic acid construct" (and by analogy, a "recombinant polypeptide" produced by the expression of a recombinant nucleic acid) as used herein refers to a nucleic acid molecule wherein such nucleic acid is not naturally occurring, or is made by the artificial combination of two otherwise separated segments of sequence by chemical synthesis, or the artificial manipulation of isolated segments of nucleic acids.

The term "SBP2 protein" as used herein refers to SECIS binding protein 2.

The term "selenocysteine insertion sequence (SECIS) element" as used herein refers to a cis-acting element that provides for insertion of a Sec residues into a protein encoded by an operably linked nucleic acid.

The term "selenoprotein" as used herein refers to selenocysteine (Sec)-containing polypeptides. Selenocysteine residues are encoded by the UGA codon. The present invention contemplates both naturally occurring selenoproteins comprising selenocysteine residues in their native form and artificial selenoproteins wherein a UGA codon is provided for in i) naturally occurring polypeptides that do not natively comprise selenocysteine residues or ii) synthetic peptides comprising selenocysteine residues.

The organism "*Toxoplasma*" as referred to herein refers to any specie of the genus of the apicomplexan organism *Toxoplasma*.

The term "transformation" as used herein refers to the introduction of a recombinant nucleic acid into a cell. Recombinant nucleic acid constructs can be introduced into a cell through a variety of standard methods such as, for example, but not limited to, chemical transfection, liposome-mediated transfections, microprojectile-mediated delivery, and electroporation.

The phrase "transformed cell" as used herein refers to a cell into which a recombinant nucleic acid construct has been introduced. It should be understood that a transformed cell as used herein refers not only to the particular cell to which a recombinant nucleic acid is introduced, but also to the progeny of such cell comprising a recombinant nucleic acid construct. Because certain modifications can occur in succeeding generations due to either mutation or environmental influences, such progeny may not, in fact, be identical to the parent cell, but are still included within the scope of the term "transformed cell" as used herein.

The term "vector" as used herein refers to any nucleic acid that can be used for the purpose of transformation, i.e., the introduction of heterologous DNA into a host cell.

II. Recombinant Nucleic Acid Constructs Comprising a Eukaryotic SECIS Element

A. Eukaryotic Selenocysteine Insertion Sequence (SECIS) Elements

Figure 12A:
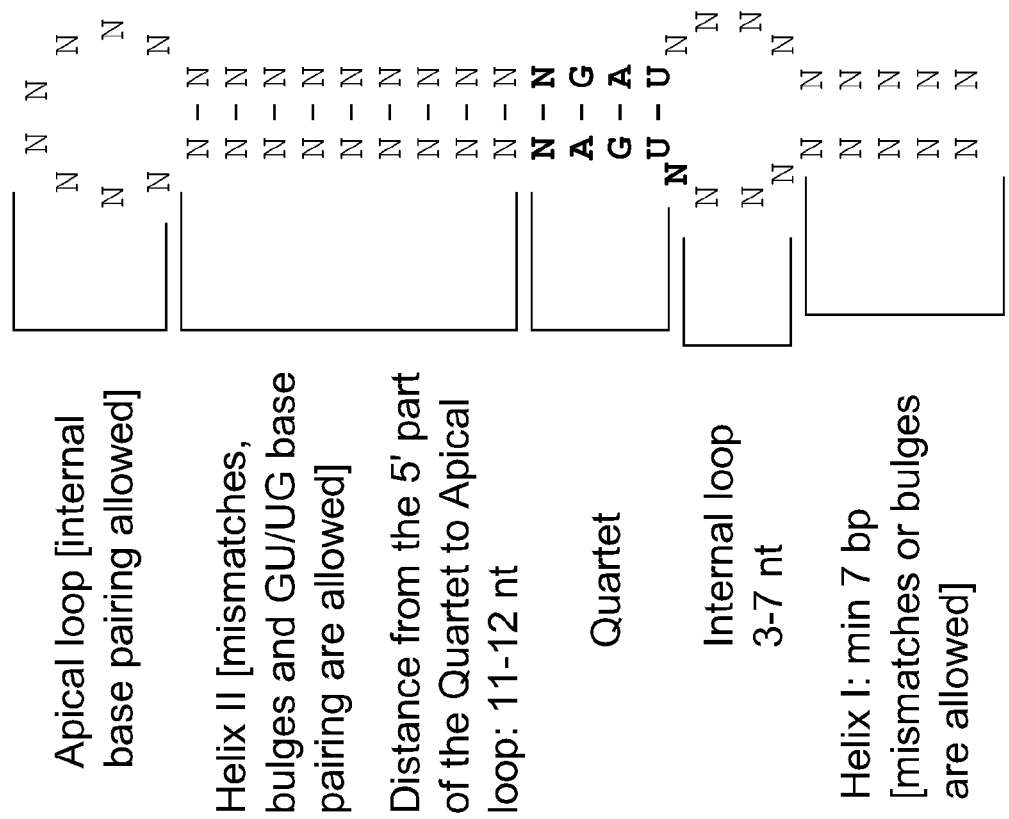
Figure 13:
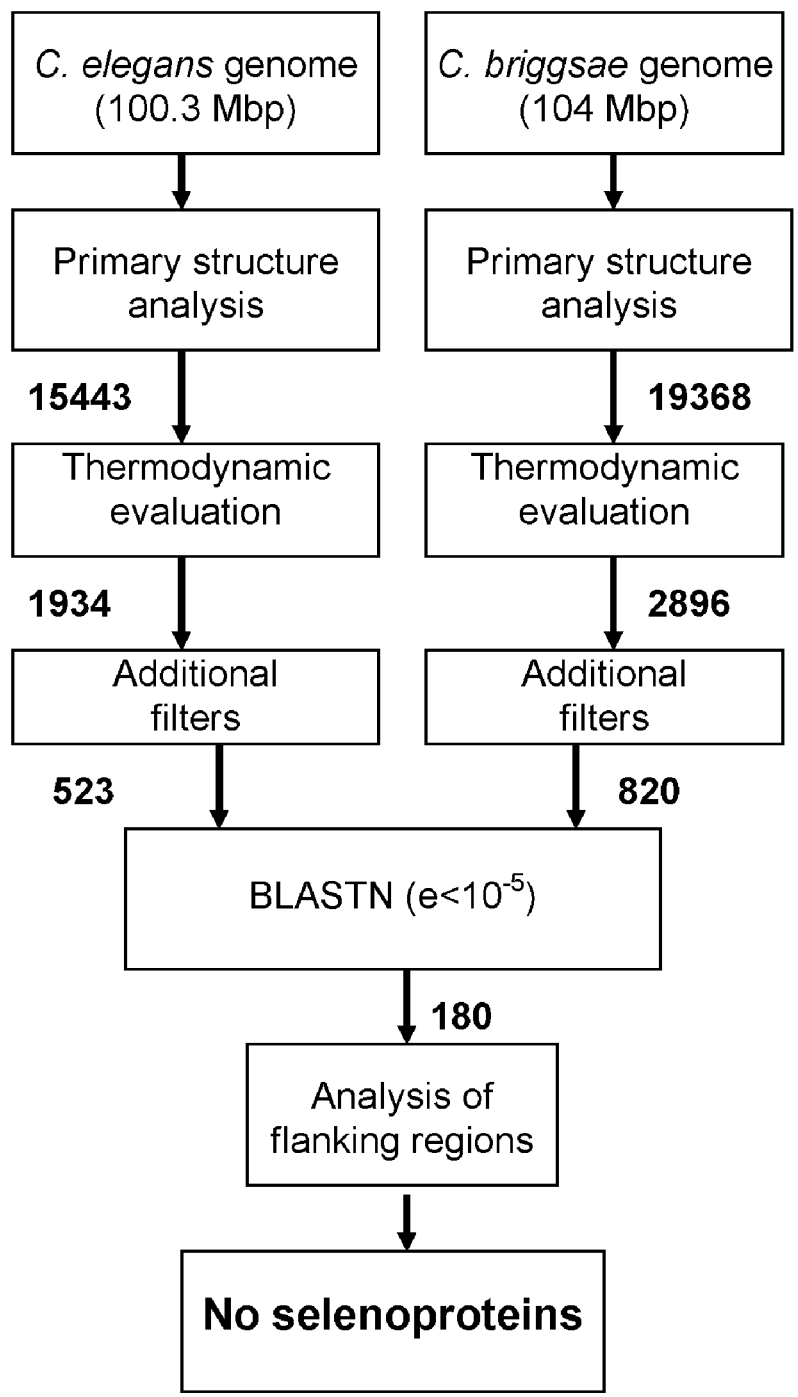
FIG. 13 shows an analysis of nematode genomes with a modified version of SECISearch. Each step in the search procedure is shown as a separate box with the numbers of SECIS candidates indicated on the left for *C. elegans*, and on the right for *C. briggsae*.

The general structure of a eukaryotic SECIS element is a stem-loop structure that comprises, in the 5' to 3' direction: a 5' proximal first helix (Helix I) sequence, a 5' proximal internal loop sequence, a 5' proximal quartet sequence, a 5' proximal second helix (Helix II) sequence, an apical loop sequence that connects the 5' proximal and 3' proximal sequences, a 3' proximal second helix (Helix II) sequence, a 3' proximal quartet sequence, a 3' proximal internal loop sequence, and a 3' proximal first helix (Helix I) sequence (FIGS. 12A and 12B), wherein Watson-Crick and non-Watson-Crick base pairing between numerous residues of the 5' proximal and 3' proximal sequences and, in some instances, between residues within the apical loop sequence, define a conserved secondary nucleic acid structure (FIGS. 12A and 12B). Although eukaryotic SECIS elements have low sequence conservation, their secondary structure is conserved, thermodynamically stable, and well established. Numerous eukaryotic selenoprotein genes containing SECIS elements that comprise a canonical quartet sequence (5'-UGAN-3') include, but are not limited to: *H. sapiens* SelK (SEQ ID NO: 30), *M. musculus* SelK (SEQ ID NO: 31), *G. gallus* SelK (SEQ ID NO: 32), *C. reinhardtii* SelK (SEQ ID NO: 33), *D. discoideum* SelK (SEQ ID NO: 34), *D. melanogaster* SelK (SEQ ID NO: 35), *H. sapiens* SelW (SEQ ID NO: 36), *M. musculus* SelW (SEQ ID NO: 37), *D. rerio* SelW (SEQ ID NO: 38), *C. reinhardtii* SelW1 (SEQ ID NO: 39), *C. reinhardtii* SelW2 (SEQ ID NO: 40), *H. sapiens* SelT (SEQ ID NO: 45), *G. gallus* SelT (SEQ ID NO: 46), and *C. reinhardtii* SelT (SEQ ID NO: 50).

i. SECIS Element Comprising a 5' Proximal 5'-GGAN-3' Quartet Sequence

One embodiment of the present invention is directed to a recombinant nucleic acid construct comprising a sequence that encodes a eukaryotic selenocysteine insertion sequence (SECIS) element comprising a non-canonical 5' proximal 5'-GGAN-3' quartet sequence.

One feature of the eukaryotic SECIS element is a segment containing four non-Watson-Crick base pairs, designated herein as the quartet sequence or quartet region (FIGS. 12A and 12B). The quartet sequence comprises a 5' proximal sequence of four nucleotides and a 3' proximal sequence of four nucleotides that form the non-Watson-Crick base pairs. The 5' proximal and 3' proximal quartet sequences are separated by other sequences, including the apical-loop structure. The prior art teaches that the 5' proximal quartet sequence is invariantly 5'-UGAN-3'. Thus, such 5'-UGAN-3' sequence is herein designated as the canonical 5' proximal quartet sequence. The present invention identifies a novel 5' proximal quartet sequence comprising the sequence 5'-GGAN-3' herein designated as the non-canonical 5' proximal quartet sequence. Although certain other references in the art may refer to other variations of the eukaryotic SECIS element as canonical or non-canonical, it is understood that as those terms are used herein, they are used consistent with the aforementioned descriptions.

Figure 1A:
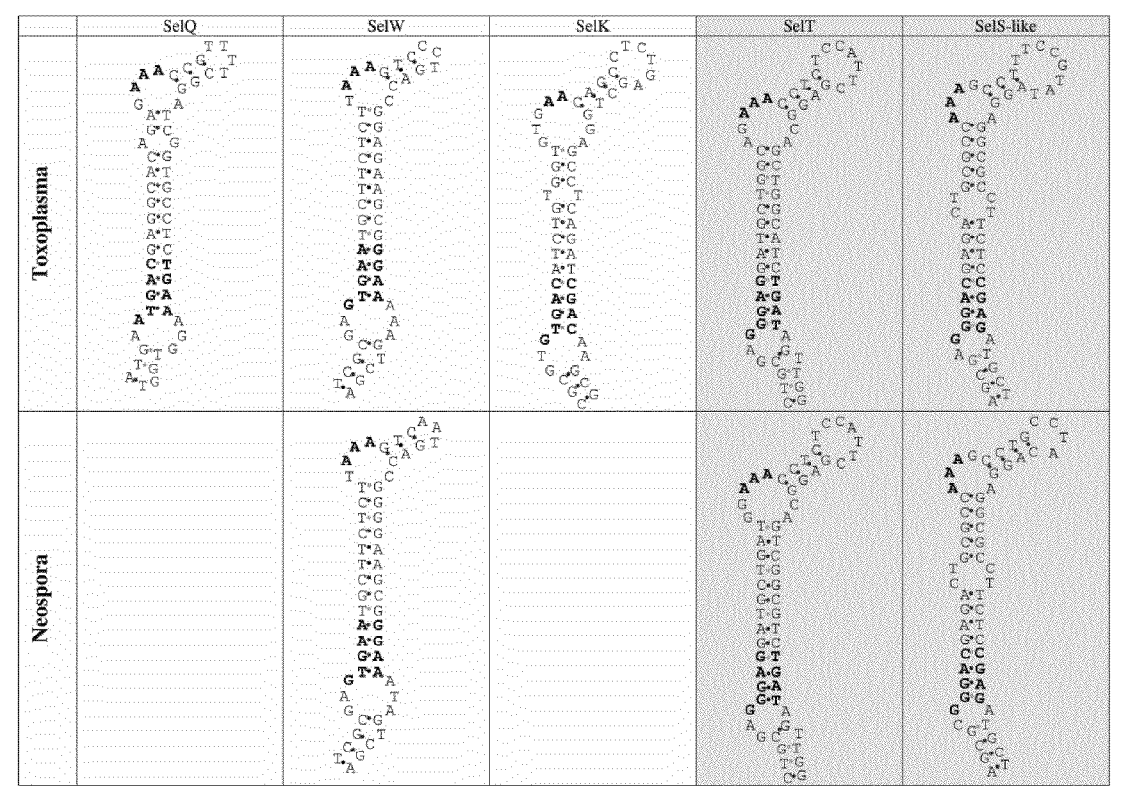

In one embodiment, the non-canonical 5' proximal 5'-GGAN-3' quartet sequence of the eukaryotic SECIS element of the invention is the native quartet sequence of the SECIS element of the selenoprotein gene from which it is obtained. Non-limiting examples of eukaryotic SECIS elements that have been identified that have a native 5' proximal quartet 5'-GGAN-3' quartet sequence include the *Toxoplasma* SelT SECIS element, the *Toxoplasma* SelS-like SECIS element, the *Neospora* SelT SECIS element, and the *Neospora* SelS-like SECIS element (FIG. 1A). FIGS. 2A, 2B, 2C and 10 demonstrate that SECIS elements comprising a native 5' proximal 5'-GGAN-3' quartet sequence can support insertion of Sec into selenoproteins in mammalian cell expression systems when such SECIS elements are operably linked to a nucleic acid encoding a selenoprotein.

Other eukaryotic SECIS elements comprising non-canonical quartet sequences or associated selenoprotein genes not explicitly disclosed herein can also be used in the practice of this invention. In particular, it is contemplated that the disclosure of the non-canonical '5-GGAN-3' quartet sequence provided herein will facilitate the identification of additional selenoprotein genes and associated SECIS elements comprising non-canonical quartet elements in the genomes of other organisms that have not been characterized or entered into databases. Exemplary database search techniques for identifying native eukaryotic SECIS elements comprising non-canonical quartet sequences include, but are not limited to, those described in FIG. 15 and the associated figure legend, as well as in Examples 1, 6, and 7.

Figure 3A:
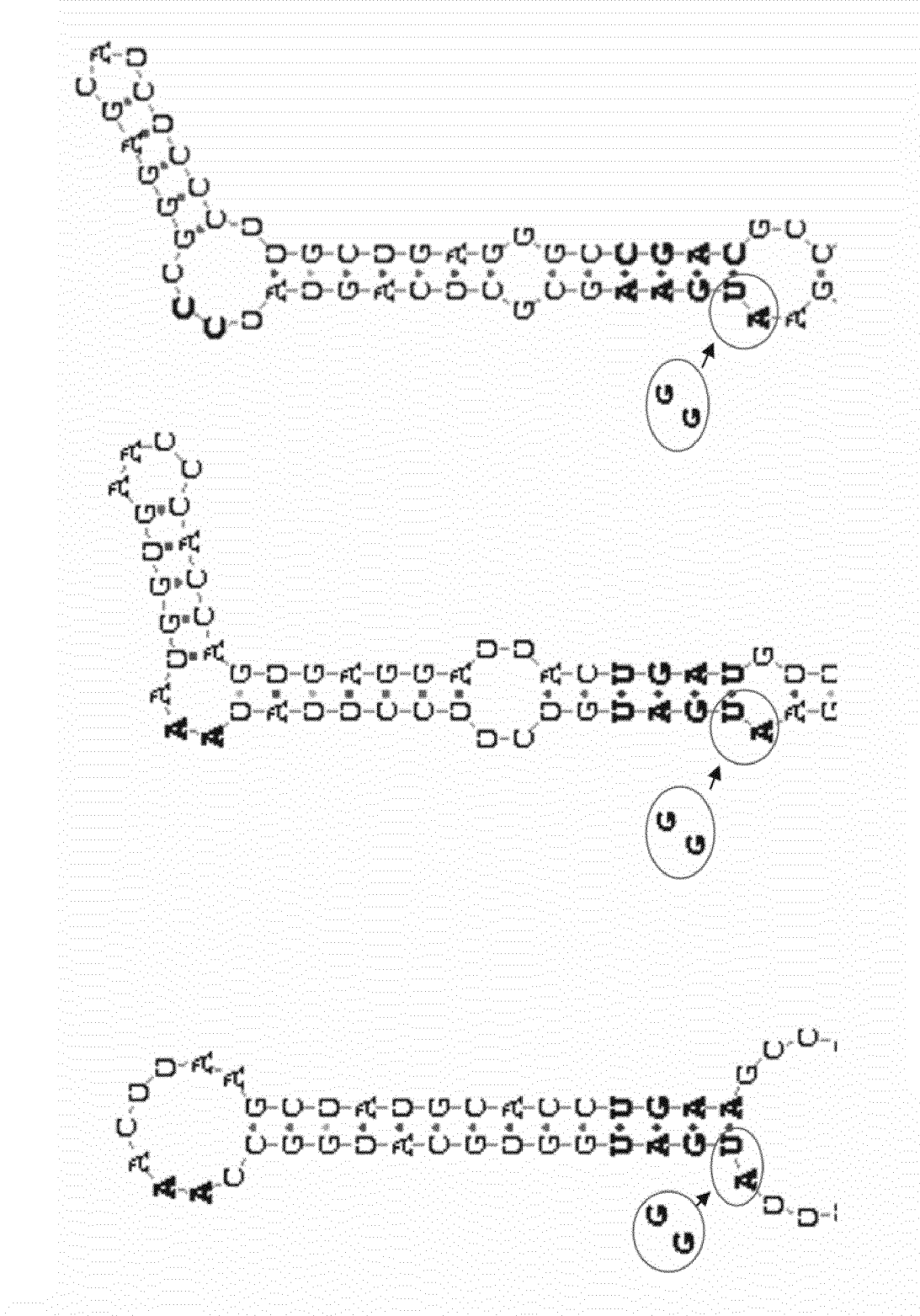
Figure 3B:
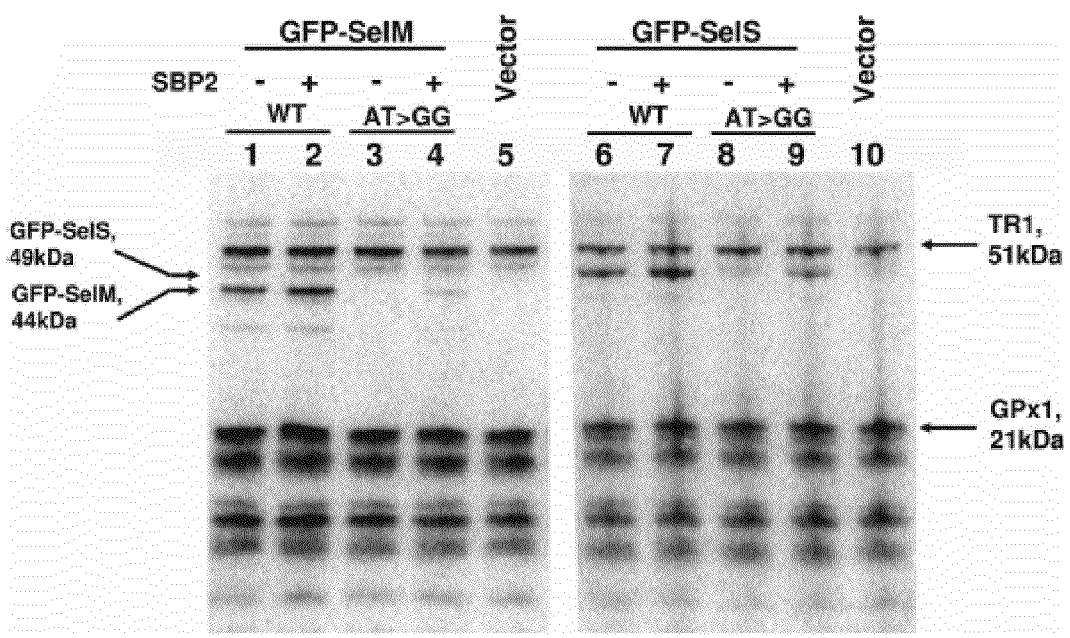
Figure 3C:
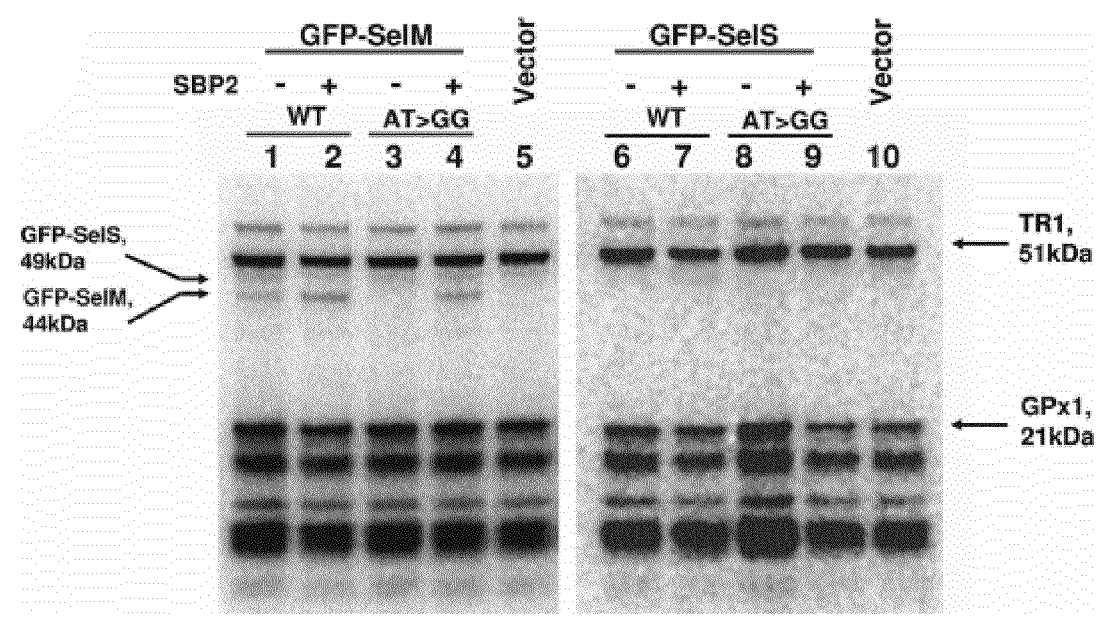

In another embodiment, the non-canonical 5' proximal 5'-GGAN-3' quartet sequence of the eukaryotic SECIS element of the invention is a chimeric SECIS element wherein the 5'-GGAN-3' non-native quartet sequence is not found in the native SECIS element of the selenoprotein gene from which the chimeric SECIS element of the invention was derived. Thus, the native selenoprotein gene contains a native SECIS element sequence comprising the canonical 5' proximal 5'-UGAN-3' quartet sequence. To form a non-canonical chimeric SECIS element, a canonical eukaryotic SECIS element comprising a native 5' proximal 5'-UGAN-3' quartet sequence can be changed to comprise the non-native/non-canonical 5' proximal 5'-GGAN-3' quartet sequence. For example, if the naturally occurring (i.e., native) 5' proximal quartet sequence of a eukaryotic SECIS element is 5'-UGAN-3', a "chimeric SECIS element" would substitute said 5'-UGAN-3' quartet sequence with, for example, the non-native sequence 5'-GGAN-3'. By way of another example, if the native 5' proximal quartet sequence of a eukaryotic SECIS element is 5'-GGAN-3', a "chimeric SECIS element" would substitute said 5'-GGAN-3' quartet sequence with, for example, the non-native sequence 5'-UGAN-3'. FIGS. 3A, 3B, and 3C demonstrate that chimeric SECIS elements comprising a non-canonical quartet sequence in place of a canonical quartet sequence are functional in supporting the insertion of Sec into selenoproteins.

Examples of eukaryotic SECIS elements comprising a canonical 5' proximal 5'-UGAN-3' quartet sequence that can be changed to form a chimeric SECIS element comprising a non-canonical sequence include, but are not limited to, the mammalian SelS SECIS element, the mammalian SelM SECIS element, the mammalian SelH SECIS element, the *Toxoplasma* SelQ SECIS element, the *Toxoplasma* SelW SECIS element, the *Toxoplasma* SelK SECIS element, and the *Neospora* SelW SECIS element. It is understood that both the non-canonical and canonical SECIS elements listed herein are non-limiting and that one of skill in the art could employ other non-canonical eukaryotic SECIS elements comprising a 5' proximal 5'-GGAN-3' quartet sequence whether such sequence is the native sequence or is part of a chimeric SECIS element.

In one embodiment, the non-canonical 5' proximal 5'-GGAN-3' quartet sequence is preceded at its immediate 5' terminus by a G residue. In certain embodiments, the residue immediately preceding the 5' terminus of a canonical quartet sequence is preferably an A residue or is an A residue. A native SECIS element can thus comprise an A residue that immediately precedes the canonical quartet sequence element to provide a native 5'-AUGAN-3' sequence. In other embodiments where the SECIS element comprises a non-canonical 5' proximal 5'-GGAN-3' quartet sequence, the residue immediately preceding the 5' terminus of the quartet sequence is preferably a G residue or is a G residue. Such G residues that precede the non-canonical quartet sequence can be part of a native SECIS element sequence. For example, in certain native SECIS elements, the native quartet sequence and the immediately preceding 5' terminal residue comprise the native sequence 5'-GGGAN-3'. The G residue preceding the non-canonical quartet sequence can also be a non-native residue. For example, as part of a chimeric SECIS element wherein the native 5' proximal 5'-UGAN-3' quartet sequence is preceded at its immediate 5' terminus by a native A residue, the quartet sequence can be changed to a non-native 5' proximal 5'-GGAN-3' quartet sequence preceded at its immediate 5' terminus by a non-native G residue. Thus, the chimeric SECIS element including the non-native quartet sequence and the non-native immediate 5' terminus residue would substitute the sequence 5'-GGGAN-3' for the native 5'-AUGAN-3' sequence of the native SECIS element.

ii. Chimeric SECIS Element Comprising a 5' Proximal 5'-UGAN-3' Quartet Sequence

One embodiment of the present invention is directed to a recombinant nucleic acid construct comprising a sequence that encodes a chimeric eukaryotic selenocysteine insertion sequence (SECIS) element comprising a canonical 5' proximal 5'-UGAN-3' quartet sequence. It is contemplated that any eukaryotic SECIS element comprising a non-canonical 5' proximal 5'-GGAN-3' quartet sequence can be used to obtain the chimeric SECIS element of this embodiment. Non-canonical eukaryotic SECIS elements identified herein as well as other non-canonical eukaryotic sequence elements identifiable through database search methods disclosed herein can identify the non-canonical eukaryotic SECIS element. Exemplary database search techniques for identifying native eukaryotic SECIS elements comprising non-canonical quartet sequences include, but are not limited to, those described in FIG. 15 and the associated figure legend, as well as in Examples 1, 6, and 7.

One principal feature of the eukaryotic SECIS element known in the art is a segment containing four non-Watson-Crick base pairs designated herein as the quartet sequence or quartet region. In certain eukaryotic SECIS elements, a non-canonical 5' proximal 5'-GGAN-3' quartet sequence is the native sequence of the selenoprotein gene. Non-limiting examples of eukaryotic SECIS elements that have been identified that comprise such native 5'-GGAN-3' quartet sequences include the *Toxoplasma* SelT SECIS element, the *Toxoplasma* SelS-like SECIS element, the *Neospora* SelT SECIS element, and the *Neospora* SelS-like SECIS element.

Figure 4A:
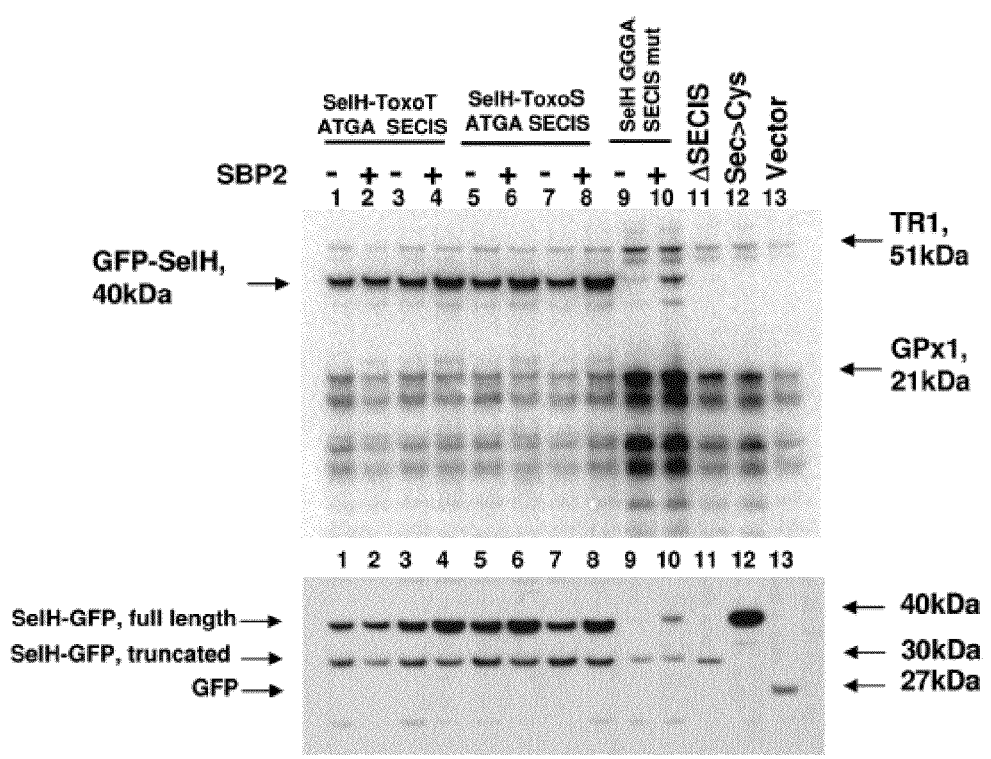
Figure 4B:
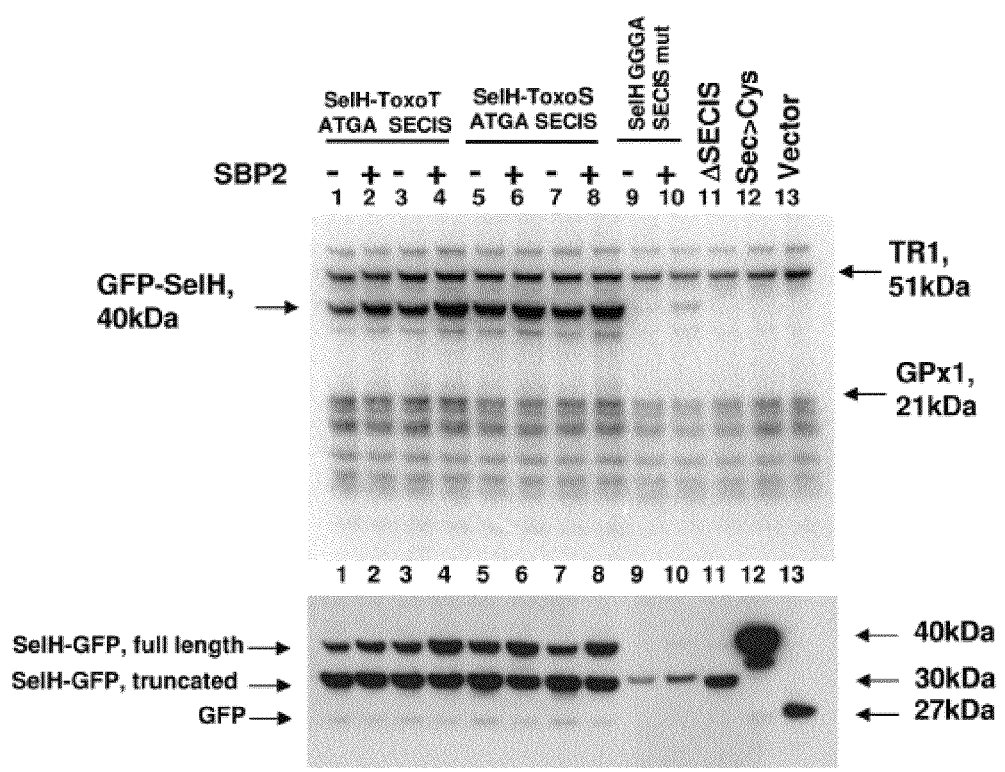

In certain embodiments, a chimeric SECIS element is formed when a non-canonical 5'-proximal 5'-GGAN-3' quartet sequence is changed to comprise a canonical 5' proximal 5'-UGAN-3' quartet sequence. Such a substitution of a canonical quartet sequence for a non-canonical quartet sequence in a non-canonical SECIS element has been shown to be both active and efficient when such SECIS elements are operably linked to a nucleic acid encoding a selenoprotein. (FIGS. 4A, 4B, and 11).

Further, it has been observed that when the SECIS element comprises a non-canonical 5' proximal 5'-GGAN-3' quartet sequence, such sequence is generally preceded immediately at its 5' terminus by a G residue. In certain embodiments of the chimeric SECIS element, the canonical 5' proximal 5'-UGAN-3' quartet sequence is preceded at its immediate 5' terminus by an A residue. Thus, the chimeric SECIS element including the quartet sequence and the immediate 5' terminus residue comprises the sequence 5'-AUGAN-3' as compared to the native 5'-GGGAN-3' sequence of the original non-canonical SECIS element.

B. Operably Linked to Heterologous Expression Control Sequences

In a preferred embodiment of the present invention, the sequence that encodes a eukaryotic SECIS element is "operably linked" (see Definition Section) to a heterologous expression control sequence. The phrase "expression control sequence" includes, but is not limited to, appropriate SECIS elements transcription initiation elements, transcription termination elements, promoters for DNA-dependent RNA polymerases, promoters or initiation sites for RNA-dependent RNA polymerases, enhancer sequences, efficient RNA processing signals such as splicing and polyadenylation signals, sequences that stabilize cytoplasmic mRNA, sequences that enhance translation efficiency (e.g., ribosome binding sites), internal ribosome entry sites (IRES), sequences that enhance protein stability, and when desired, sequences that enhance protein secretion.

A heterologous coding sequence can include, but is not limited to, prokaryotic coding sequences, cDNA from eukaryotic mRNA, genomic DNA sequences from eukaryotic DNA, and synthetic DNA sequences. If the DNA coding sequence is intended for expression in a eukaryotic cell, a polyadenylation signal and transcription termination sequence can be located 3' to the coding sequence.

In certain embodiments, the expression control sequence comprises a promoter sequence. Such promoter sequence can be operably linked to a sequence encoding heterologous polypeptides, a SECIS element of the invention and a polyadenylation sequence. The promoter includes necessary nucleic acid sequences near the start site of transcription, such as, in the case of a RNA polymerase II type promoter, a TATA element. A promoter also optionally includes distal enhancer or repressor elements which can be located as much as several thousand base pairs from the start site of transcription. Those skilled in the art recognize that a variety of promoters are well characterized and can be used in the practice of this invention. The promoters can be either constitutive, inducible or tissue-specific in their activity. A "constitutive" promoter is a promoter that is active under most environmental and developmental conditions. An "inducible" promoter is a promoter that is active under environmental or developmental regulation. Constitutive promoters useful for expression in eukaryotic cells include, but are not limited to, viral promoters or promoters for endogenous genes. Viral promoters useful for expression in mammalian cells include, but are not limited to, CMV, SV40, and RSV promoters.

In another preferred embodiment, an expression control sequence can comprise a polyadenylation sequence. Polyadenylation sequences (also know in the art as polyadenylation signals; polyadenylation regions) provide for the addition of polyadenylate sequence to the 3' end of mRNA.

Such a polyadenylation sequence is operably linked to other sequences such that it can perform its intended function. Those skilled in the art will recognize that a variety of polyadenylation sequences are well characterized and can be used in the practice of this invention.

The use of a wide variety of expression vectors are contemplated in the practice of this invention.

In certain embodiments, the vectors can be either episomal or can be integrated into the host cell genome.

In other embodiments, the vectors can replicate within host cell(s) or, alternatively, can be transient expression vectors that are not maintained indefinitely in the host cell(s). Examples of recombinant nucleic acid constructs are well known to those skilled in the art and include, but are not limited to, plasmids, cosmids, viruses, bacterial artificial chromosomes (BACs), yeast artificial chromosomes (YACs), plant minichromosomes, autonomously replicating sequences, phage, or linear or circular single-stranded or double-stranded nucleic acid sequences, derived from any source, that are capable of genomic integration or autonomous replication. Recombinant nucleic acid constructs can be assembled by a variety of methods including but not limited to recombinant DNA techniques, DNA synthesis techniques, polymerase chain reaction (PCR) techniques, or any combination of such techniques.

C. Operably Linked to a Heterologous Coding Sequence

In a preferred embodiment of the present invention, the sequence that encodes a eukaryotic SECIS element is "operably linked" (see Definition Section) to a heterologous coding sequence. In certain embodiments, the operably linked SECIS element is located 3' to the translation termination codon in the 3' untranslated region (3'UTR) that is operably linked to the heterologous sequence.

Therefore, the eukaryotic SECIS element is inserted into the 3' untranslated region (3' UTR) such that both the SECIS element and the 3'UTR are operably linked to the heterologous coding sequence. The location of the operably linked SECIS element in the 3'UTR may range from about 1 to about 5000 nucleotides 3' of the translation termination codon.

In one embodiment, the SECIS element comprises a non-canonical 5' proximal 5'-GGAN-3' quartet sequence. Such 5' proximal 5'-GGAN-3' quartet sequence can be the native sequence of the SECIS element such as, for example, but not limited to, when the SECIS element is from a *Toxoplasma* SelT gene, *Toxoplasma* SelS-like gene, *Neospora* SelT gene, or a *Neospora* SelS-like gene. The 5' proximal 5'-GGAN-3' quartet sequence can alternatively be a non-native sequence that replaces the native 5' proximal quartet sequence such as, for example, from a canonical SECIS element, to form a chimeric SECIS element. Non-limiting examples of canonical eukaryotic SECIS elements from which such 5' proximal 5'-UGAN-3' quartet sequence to 5' proximal 5'-GGAN-3' quartet sequence chimeric SECIS elements can be formed are the mammalian SelS SECIS element, the mammalian SelT SECIS element, the mammalian SelH SECIS element, the *Toxoplasma* SelQ SECIS element, the *Toxoplasma* SelW SECIS element, the *Toxoplasma* SelK SECIS element, and the *Neospora* SelW SECIS element. It has been found that when the 5' proximal quartet sequences comprises the non-canonical 5'-GGAN-3' sequence, whether it is the native sequence or a chimeric sequence of the SECIS element, the 5' proximal quartet sequence is preferably preceded immediately at its 5'-terminus by a G residue therefore comprising the sequence 5'-GGGAN-3'.

In another embodiment, the SECIS element is a chimeric SECIS element wherein a native non-canonical 5' proximal 5'-GGAN-3' quartet sequence is replaced with a canonical 5' proximal 5'-UGAN-3' quartet sequence. Non-limiting examples of non-canonical eukaryotic SECIS elements from which such 5' proximal 5'-GGAN-3' quartet sequence to 5'-UGAN-3' quartet sequence chimeric SECIS elements can for formed are the *Toxoplasma* SelT SECIS element, the *Toxoplasma* SelS-like SECIS element, the *Neospora* SelT SECIS element, and the *Neospora* SelS-like SECIS element. It has been found that when the chimeric SECIS element comprises a 5' proximal 5'-UGAN-3' quartet sequence, the 5' proximal quartet sequence is preferably preceded immediately at its 5' terminus by an A residue therefore comprising the sequence 5'-AUGAN-3'.

D. Heterologous Sequence Comprising a Site for Operable Insertion of a Sequence that Encodes a Heterologous Polypeptide In certain embodiments of the present invention, the sequence that encodes a eukaryotic SECIS element is operably linked to heterologous sequence comprising a site for operable insertion of a sequence that encodes a heterologous polypeptide. Thus, a sequence encoding a heterologous polypeptide can be inserted into the site for operable insertion of a recombinant nucleic acid construct of the invention such that the sequence encoding a heterologous polypeptide and the sequence that encodes a eukaryotic SECIS element are operably linked. The operably linked SECIS element will thus provide for incorporation of a selenocysteine residue into the heterologous polypeptide encoded by the sequence that was inserted into the site for operable insertion. In certain embodiments, the site for operable insertion of a heterologous sequence would be located 3' to an expression control element and 5' to a 3' untranslated region (3'UTR) comprising a SECIS element of the invention. In certain embodiments, the site for operable insertion of a heterologous sequence would be located 3' to a promoter and the site of transcriptional initiation and 5' to a 3' untranslated element comprising a SECIS element of the invention.

The site for operable insertion can comprise any sequence that provides for operable insertion of the heterologous sequence in the recombinant nucleic acid. In certain embodiments, the heterologous sequence comprising a site for operable insertion of a sequence that encodes a heterologous polypeptide comprises at least one restriction endonuclease recognition sequence. Restriction endonucleases and their recognition sequences are routinely used in the art to combine nucleic acid sequences to form recombinant nucleic acid constructs wherein joined sequences are operably linked. Further, it is understood that the restriction endonucleases and their recognition sequences disclosed herein are non-limiting examples and that other such restriction endonucleases and their recognition sequences not explicitly cited herein may be employed in the practice of the current invention. In still other embodiments, the site for operable insertion of the heterologous sequence can comprise a site for integration by homologous recombination. In still other embodiments, the site for operable insertion of the heterologous sequence can comprise a site-specific recombination recognition sequence. Examples of site-specific recombination recognition sequences include, but are not limited to, lox sites recognized by a bacteriophage P1 Cre recombinase, or FRT sites recognized by a yeast FLP recombinase. In still other embodiments, the site for operable insertion can comprise a Ligation Independent Cloning site that provides for DNA topoisomerase I mediated integration of the heterologous coding sequence. Various methods for operable insertion of heterologous sequences into specified sites in U.S. Pat. No. 7,109,178, which is incorporated herein by reference with respect to its disclosure of Ligation Independent Cloning and directional cloning.

E. Production of Heterologous Polypeptide Containing Selenocysteine Residues

Selenocysteine (Sec), the 21st amino acid, is encoded by the UGA codon in mRNAs that comprise operably linked SECIS elements. In certain embodiments, a sequence encoding a heterologous polypeptide that comprises at least one UGA codon is inserted into a recombinant nucleic acid construct comprising a eukaryotic SECIS element of the invention. In still other embodiments, a sequence encoding a heterologous polypeptide that comprises at least one UGA codon is operably linked to a eukaryotic SECIS element of the invention. The UGA codon or codons may be native to the heterologous coding sequence. For example, native sequences encoding natural selenoproteins contain UGA codons. Alternatively, UGA codons can be artificial such as when introduced by substitution or addition into a coding sequence. It is contemplated within the scope of this invention that polypeptides may be engineered to contain new or additional UGA codons encoding Sec in order to change the functional properties of such engineered polypeptides in comparison to their existing properties. For example, Sec residues can be introduced into the catalytic sites of enzymes wherein they may serve a redox function analogous to the functions of redox-active Cys residues.

Selenoproteins produced with the compositions or methods of the invention can be linear or branched, can comprise modified amino acids in addition to selenocysteine, and can be interrupted by non-amino acids. Selenoproteins produced by the methods and compositions disclosed herein can also be modified naturally or by intervention. Contemplated modifications of selenoproteins produced by the compositions or methods of the invention include but are not limited to, disulfide bond formation or disruption, glycosylation, lipidation, acetylation, carboxylation, phosphorylation, ubiquitination, or pegylation. Conjugation of the selenoproteins with a detectable label is also contemplated. Selenoproteins produced by the methods and compositions of the invention can also contain one or more analogs of an amino acid (including, for example, unnatural amino acids, etc.), as well as other modifications. Such modifications are well known; see, e.g., Molecular Cloning: A Laboratory Manual, 2nd ed., Vol. 1-3, ed. Sambrook, et al., Cold Spring Harbor Laboratory Press (1989); or Current Protocols in Molecular Biology, ed. F. Ausubel et al., Greene Publishing and Wiley-Interscience: New York (1987 and periodic updates).

F. Co-Expression of SBP2 Protein from a Second Expression Cassette

In certain embodiments, recombinant nucleic acid constructs can comprise one or more expression cassettes. One embodiment of the present invention comprises a first expression cassette comprising an operably linked expression control sequence, an operably linked heterologous coding sequence, an operably linked sequence encoding a eukaryotic SECIS element of the invention, and an operably linked polyadenylation sequence. Thus the first expression cassette is capable of expressing the heterologous coding sequence wherein the eukaryotic SECIS element acts upon the transcribed coding sequence and the polyadenylation sequence polyadenylates the mRNA.

In certain embodiments, a recombinant nucleic acid construct comprises a second expression cassette that is capable of expressing a polypeptide distinct from the polypeptide of the first expression cassette. The second expression cassette can, in certain embodiments, provide for the expression of an SBP2 protein. Co-expression of the SBP2 protein with the product of the first expression cassette (i.e. a heterologous coding sequence that is operably linked to a SECIS element) can increase the efficiency of selenocysteine incorporation into the heterologous protein encoded by the first expression cassette. SBP2 proteins that can be used include, but are not limited to: *Rattus norvegicus* (rat) SBP2 (SEQ ID NO: 19 nucleotide sequence and SEQ ID NO: 20 amino acid sequence ); *Mus musculus* (mouse) SBP2 (SEQ ID NO: 21 nucleotide sequence and SEQ ID NO: 22 amino acid sequence), *Homo sapiens* (human) SBP2 (SEQ ID NO: 23 nucleotide sequence and SEQ ID NO: 24 amino acid sequence), *Monodelphis domestica* (gray short-tailed opossum) (SEQ ID NO: 25 nucleotide sequence and SEQ ID NO: 26 amino acid sequence), and *Canis lupus familiaris* (dog) SBP2 (SEQ ID NO: 27 nucleotide sequence and SEQ ID NO: 28 amino acid sequence).

Inclusion of additional expression cassettes that provide for either selectable or scorable marker genes that provide for selection or identification of host cells that have been transformed by the vector are also contemplated herein.

G. DNA and RNA Recombinant Nucleic Acid Constructs

Alternative embodiments of the recombinant nucleic acid construct of the current invention may be a DNA construct or an RNA-based vector. RNA-based vectors include, but are not limited to, viral vectors derived from alphaviruses or flaviviruses. In such RNA-based viral vectors, the heterologous sequence would be operably linked to both the SECIS element as well as cis acting heterologous expression control sequences of the viral vector that provide for expression of the operably linked heterologous coding region and SECIS element. Flavivirus based vectors are described in U.S. Pat. No. 6,893,866, which is incorporated herein by reference in its entirety with respect to its disclosure of RNA-based vectors. Alphavirus based vectors are disclosed in U.S. Pat. No. 5,843,723, which is incorporated herein by reference in its entirety with respect to its disclosure of RNA-based vectors. Alphavirus vectors useful in the practice of this invention can be derived from a Aura, Fort Morgan, Venezuelan Equine Encephalitis, Ross River, Semliki Forest, Sindbis, and/or Mayaro virus.

H. Transformed Cell Comprising a Recombinant Nucleic Acid Construct

In certain embodiments, it is contemplated that a transformed cell comprises a recombinant nucleic acid construct of the invention. A transformed cell can be transiently transformed wherein the transformation is not permanent in nature. Alternatively, a transformed cell can be stably transformed. Stable transformation includes, but is not limited to, instances where the recombinant nucleic acid is incorporated into a chromosome or is capable of autonomous replication.

If the recombinant nucleic acid is one that provides for expression of a selenoprotein, the transformed cell is preferably a cell type that allows for expression of the selenoprotein. For example, the pSelExpress1 expression vector (see Example 5) may be used to express a selenoprotein in mammalian cells. Examples of mammalian cells that can be used to express selenoproteins include, but are not limited to, Hela, CHO, Jurkat, HepG2, H1299, HEK293 cells and NIH 3T3 cells. Cells can be transformed by any method that permits introduction of exogenous DNA into the host cell. Examples of suitable transformation methods include, but are not limited to, transfection, lipofection, electroporation, particle-mediated delivery, viral vector delivery, and the like.

I. Organism Comprising a Recombinant Nucleic Acid Construct

In certain embodiments, it is contemplated that an organism can comprise a recombinant nucleic acid construct of the invention. An organism comprising a recombinant nucleic acid of the invention is an organism, or a progeny thereof, that is derived from a transformed cell comprising a recombinant nucleic acid construct of the invention, Organisms that comprise a recombinant nucleic acid of the invention include, but are not limited to, a transgenic organism, an organism wherein an exogenous transformed cell comprising a recombinant nucleic acid construct of the invention has been introduced, and/or an organism wherein a recombinant nucleic acid construct has been introduced into the organism.

J. Kit for Obtaining a Recombinant Nucleic Acid Construct

In certain embodiments, a kit is provided for obtaining a recombinant nucleic acid construct that provides for expression of a selenoprotein. The kit may comprise one or more recombinant nucleic acid constructs according to the embodiments described herein. The kit may also comprise a control recombinant nucleic acid construct or a recombinant nucleic acid construct for the co-expression of a polypeptide other than a selenoprotein, such as, for example, but not limited to, an SBP2 protein. Recombinant nucleic acid constructs can be provided in a kit in a variety of ways, such as, for example, but not limited to, as an isolated nucleic acid wherein the nucleic acid is not contained within a cell, or provided within a transformed cell or a population of transformed cells. An isolated nucleic acid may be provided in a liquid solution or it may be provided dried. In embodiments wherein the nucleic acid is provided in a liquid solution, such solution can be an aqueous solution. The aqueous solution can be a buffered solution that stabilizes nucleic acids.

The kit also comprises instructions for use of the recombinant nucleic acid construct. Such instructions can included instructions as to the amount or concentration of the nucleic acid construct provided. Instructions may be included in the kit in either printed or electronic form. Alternatively, the instructions can be provided by way of a link or internet address that provides access to instructions located on either an internet or extranet site. The internet site can be either publicly available or secure. If the construct is provided dried, the instructions may teach how to reconstitute the nucleic acid construct into solution. The instructions may further teach how to introduce an isolated nucleic acid construct into a cell. When the recombinant nucleic acid construct is a selenoprotein expression vector, the instructions can indicate various cell types that can be transformed with the construct and how to culture the transformed cells so that they will express a selenoprotein. When the intended use of the recombinant nucleic acid construct is to provide for a selenoprotein, the instructions can also teach how to recover a selenoprotein from a transformed cell or from a conditioned cell culture medium produced by a transformed cell.

K. Methods of Obtaining a Selenoprotein

The present invention provides for methods of obtaining a selenoprotein. Such methods comprise culturing a cell comprising a recombinant nucleic acid construct of the invention under conditions permitting expression of a selenoprotein encoded by the recombinant nucleic acid construct. It will be recognized by one skilled in the art that such conditions will depend upon the type of cell being cultured and the properties of the recombinant nucleic acid construct that control expression of the selenoprotein. Following expression of a selenoprotein, the selenoprotein can be recovered, isolated, purified, enriched, or the like, from a cultured cell comprising a recombinant nucleic acid construct of the invention or from a cell culture medium in which cell has been cultured. It is contemplated that a selenoprotein can be recovered by various methods well known in the art, including but not limited to, precipitation, centrifugation, size exclusion chromatography, ion exchange chromatography, affinity chromatography, or other known recovery techniques. It is also contemplated that a selenoprotein may be recovered by utilizing any of numerous "tags" known in the art that may be added to a polypeptide in order to aid in its recovery, isolation, purification, enrichment, or the like. Useful tags include, but are not limited to, histidine tags that comprise poly(His) residues, and GST tags. In certain embodiments, the tag is operably linked to the sequence targeted for purification by a protease recognition site that provides for removal of the tag.

The expression of a selenoprotein by a recombinant nucleic acid construct of the invention may be enhanced by the co-expression of another polypeptide. Such polypeptide can be an SBP2 protein. SBP2 proteins that can be used include, but are not limited to: *Rattus norvegicus* (rat) SBP2 (SEQ ID NO: 19 nucleotide sequence and SEQ ID NO: 20 amino acid sequence); *Mus musculus* (mouse) SBP2 (SEQ ID NO: 21 nucleotide sequence and SEQ ID NO: 22 amino acid sequence), *Homo sapiens* (human) SBP2 (SEQ ID NO: 23 nucleotide sequence and SEQ ID NO: 24 amino acid sequence), *Monodelphis domestica* (gray short-tailed opossum) (SEQ ID NO: 25 nucleotide sequence and SEQ ID NO: 26 amino acid sequence), and *Canis lupus familiaris* (dog) SBP2 (SEQ ID NO: 27 nucleotide sequence and SEQ ID NO: 28 amino acid sequence). In certain embodiments, a recombinant nucleic acid construct comprising a selenoprotein expression cassette comprising a sequence that encodes a eukaryotic (SECIS) element of the invention that is operably linked to both a heterologous expression control sequence and a heterologous sequence that encodes a heterologous polypeptide containing at least one UGA codon is co-transformed into a cell with a second recombinant nucleic acid construct comprising a second expression cassette for the expression of a second polypeptide. In other embodiments, a recombinant nucleic acid construct comprises a first expression cassette that is a selenoprotein expression cassette, and the same recombinant nucleic acid construct can further comprise a second expression cassette that encodes a second polypeptide.

EXAMPLES

The following disclosed embodiments are merely representative of the invention which may be embodied in various forms. Thus, specific structural and functional details disclosed in the following examples are not to be interpreted as limiting.

For the following Examples, chemicals used were purchased from Sigma (St. Louis, Mo., USA), restriction enzymes from Amersham Pharmacia (Piscataway, N.J., USA), DNA purification kits from Qiagen (Valencia, Calif., USA), mammalian cell culture reagents and the HEK 293 cell line from Invitrogen (Carlsbad, Calif., USA), and NIH 3T3 cells from American Type Culture Collection (ATCC) (Manassa, Va., USA).

*Toxoplasma gondii, C. elegans*, human and mouse genome sequences and nonredundant protein sequences were obtained through the National Center of Biotechnology Information on either the world wide web at ncbi.nlm.nih.gov or via the internet at ftp://ftp.ncbi.nih.gov/genbank. SECISearch was used for identification of candidate SECIS elements (Hatfield and Gladyshev, 2002). BLAST and FASTA programs were used for similarity searches (Bock et al., 2006).

Example 1

Identification of a Noncanonical Form of Eukaryotic SECIS Element

A search for *Toxoplasma* selenoprotein genes was carried out by homology analyses involving all known selenoproteins as queries. This procedure identified homologs of four mammalian selenoproteins: *Toxoplasma* SelK (SEQ ID NO: 29), *Toxoplasma* SelW (SEQ ID NO: 41), *Toxoplasma* SelS-like (SEQ ID NO: 43), and *Toxoplasma* SelT (SEQ ID NO: 51) (FIGS. 6-9). Their genes had predicted Sec residues encoded by UGA codons. Analysis of the 3'-UTRs in these selenoprotein genes revealed the presence of canonical SECIS elements in *Toxoplasma* SelK and *Toxoplasma* SelW genes (FIG. 1A). However, no suitable structure was found in the SelT 3'-UTR. The use of relaxed settings and the loose pattern of SECISearch did not yield candidate SECIS structures in the *Toxoplasma* SelT gene.

The lack of a standard SECIS element in the *Toxoplasma* SelT gene suggested the presence of a non-canonical structure. Manual analysis of the *Toxoplasma* SelT 3'-UTR using MFOLD revealed a SECIS-like structure that satisfied all SECIS element requirements with one notable exception: the 5' proximal quartet sequence had a 5'-GGAN-3' sequence instead of 5'-UGAN-3' and was preceded at its immediate 5'-terminus by a G residue (FIG. 1A). The U in the 5'-UGAN-3' sequence was previously considered invariant as it was present in all known eukaryotic SECIS elements. To examine if the 5'-GGAN-3' sequence in the SECIS 5' proximal quartet sequence and the G immediately preceding the quartet represented a sequencing error, additional protozoan sequences were analyzed. EST sequences of *Neospora* caninum, another apicomplexan parasite, revealed a SelW homolog (*Neospora* SelW (SEQ ID NO: 42)) containing a canonical SECIS element and a SelT homolog (*Neospora* SelT (SEQ ID NO: 52)) containing a 5'-GGAN-3'-type SECIS element preceded at its immediate 5'-terminus by a G residue (FIG. 1A). The occurrence of the same non-canonical SECIS-like structure in two different organisms was a strong indication that this structure is the true SECIS element.

Example 2

The New 5'-GGAN-3'-Type of SECIS Element is Functional

Figure 2A:
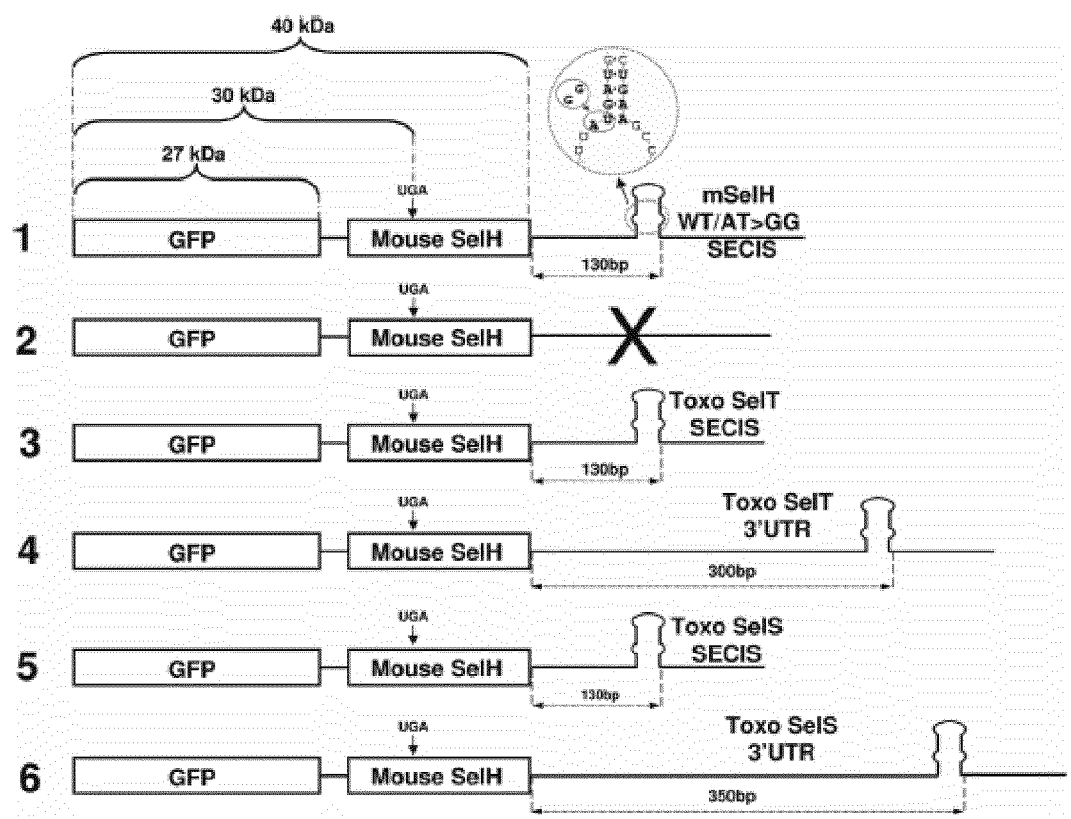

Green fluorescent protein (GFP)-mouse SelH fusion proteins (SEQ ID NO: 62 nucleotide sequence and SEQ ID NO: 63 amino acid sequence) constructs were prepared in which the natural mouse SelH SECIS element (SEQ ID NO: 9) was replaced with a *Toxoplasma* SelT SECIS element (SEQ ID NO: 4) or SelS-like SECIS element (SEQ ID NO: 5) (FIG. 2A). Said constructs were used to express these proteins in mammalian HEK 293 (FIG. 2B) and NIH 3T3 (FIG. 2C) cells. Expression of the fusion protein was predicted to result in an 40 kDa product (FIG. 2A). Indeed, metabolic labeling of the transfected cells with $^{75}$Se revealed a 40 kDa band (lanes 1-8, upper panels in FIGS. 2B and 2C). This band was not present in cells transfected with the corresponding constructs lacking 3'UTRs (lanes 11, FIGS. 2B and 2C) or the constructs in which the Sec-encoding codons were mutated to cysteine codons (lanes 12, FIGS. 2B and 2C). It was also examined whether mammalian SBP2 could influence expression levels of the expressed selenoprotein by co-transfection with a rat SBP2 construct. In each case, SBP2 increased efficiency of Sec insertion (i.e., the 40 kDa selenoprotein band appeared to be more enriched). Thus, the 5'-GGAN-3'-type of SECIS element is not only functional, but its function could be stimulated by mammalian SBP2. Moreover, when certain constructs were used, the 5'-GGAN-3' form of SECIS element appeared to be more efficient than the native mouse SelH element (e.g., compare lanes 1-4 and 9-10, FIGS. 2B and 2C).

Figure 2B:
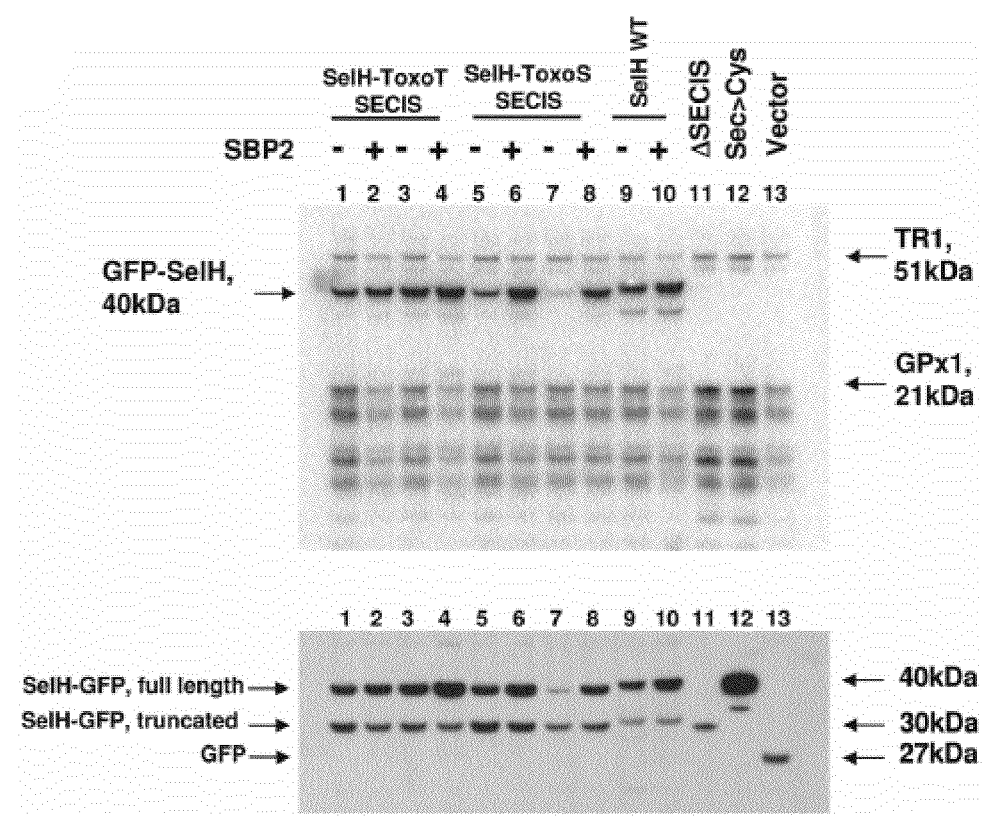
Figure 2C:
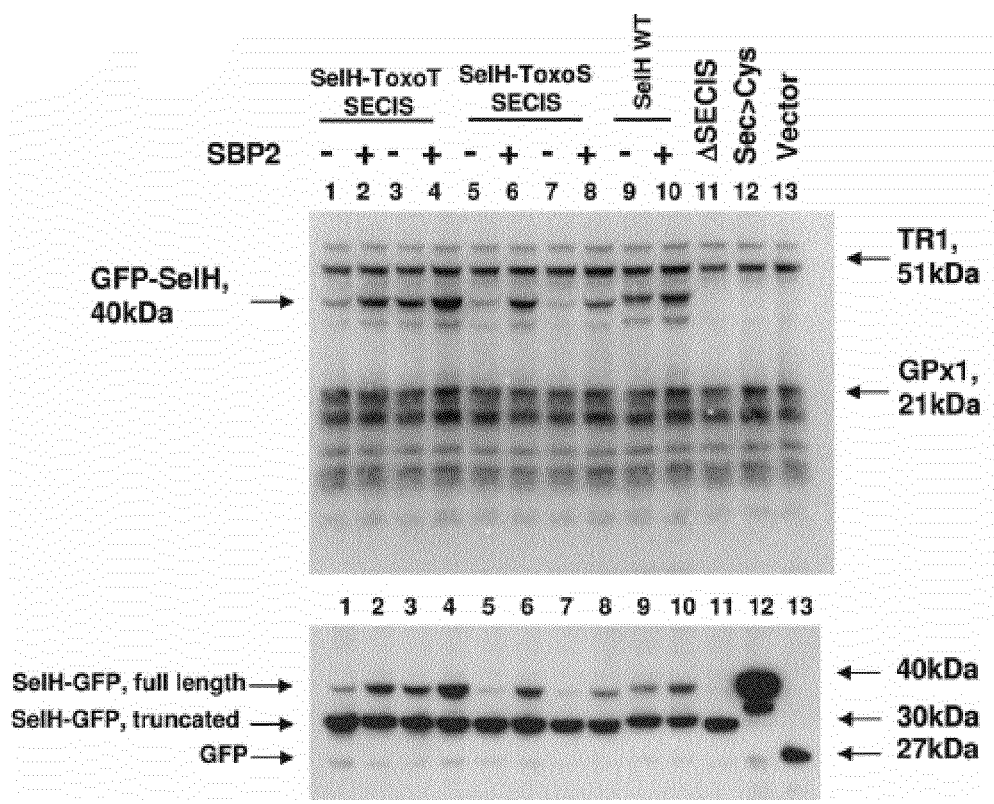

The efficiency of Sec insertion can also be monitored by probing lysates of transfected cells in western blot assays with anti-GFP antibodies to determine the ratio between full-length and truncated forms of the fusion protein (FIGS. 2B and 2C, lower panels). The truncated form is generated by termination of protein synthesis at the UGA codon due to competition of Sec insertion and translation termination, whereas the full-length protein is made when the UGA is read as the Sec codon and translation continues until the true stop signal. The ratio of full-length and truncated forms of fusion proteins that resulted from transfections with various GFP-SelH fusion proteins differed in cell lines used in the study. In HEK 293 cells, the full-length form was predominant, whereas in NIH 3T3 the truncated form was generally more abundant, suggesting lower efficiency of Sec incorporation in NIH 3T3 cells under conditions used in the study. Quantification of the ratio of full-length and truncated forms (FIG. 10) revealed that the abundance of the full-length protein expressed from the constructs carrying *Toxoplasma* SECIS elements was comparable to that containing a canonical SelH SECIS element. In some cases (e.g., *Toxoplasma* SelT 3'UTR construct, see lane 4, FIG. 10), the full-length protein was both the major selenoprotein in HEK 293 cells and significantly exceeded the corresponding truncated form of protein. Thus, the 5'-GGAN-3'-type of SECIS element is not only functional, but is also extremely efficient in Sec insertion in mammalian cells.

Example 3

5'-AGAN-3' to 5'-GGAN-3' Xhimerics of Mammalian SECIS Elements are Functional

To further characterize the 5'-GGAN-3' (preceded immediately at its 5'-terminus by a G residue) form of SECIS element, chimeric mammalian SECIS elements were tested to see if they were functional if they contain the novel, non-canonical quartet sequence. In this experiment, GFP-mouse SelS (SEQ ID NO: 64 nucleotide sequence and SEQ ID NO: 65 amino acid sequence) (Kryukov et al., 2003) and GFP-mouse SelM (SEQ ID NO: 66 nucleotide sequence and SEQ ID NO: 67 amino acid sequence) (Korotkov et al., 2002) constructs were used, in which the native 5'-UGAN-3' (preceded immediately at the 5'-terminus by an A residue) 5' proximal quartet sequences of the SECIS elements were changed to 5'-GGAN-3' (preceded immediately at its 5'-terminus by a G residue) sequences (FIG. 3A) (chimeric mouse SelM SECIS element SEQ ID NO: 13 and chimeric mouse SelS SECIS element SEQ ID NO: 14 respectively). These constructs were transfected into HEK 293 (FIG. 3B) and NIH 3T3 (FIG. 3C) cells. Chimeric forms were characterized by significantly decreased Sec insertion (compare lanes 1-2 to 3-4 for SelM and lanes 6-7 to 8-9 for SelS, FIGS. 3B and 3C). A chimeric mouse SelH SECIS element with the non-native 5'-GGAN-3' (preceded immediately at its 5'-terminus by a G residue) 5' proximal quartet sequence (chimeric mouse SelH SECIS element SEQ ID NO: 12) was also constructed and cells were transfected with this construct (compare lanes 9 and 10 in FIGS. 3B and 3 C to lanes 9 and 10 in FIGS. 4A and 4B). Again, the chimeric SECIS forms were less efficient in supporting Sec incorporation. Nevertheless, these structures were functional and dependent on SBP2. In FIG. 3A, SelH on one side and SelS and SelM on the other represent type I and type II SECIS elements, respectively, which differ by the presence of an additional mini helix (Grundner-Culemann et al., 1999). It is clear that both of these SECIS types can utilize the 5'-GGAN-3' form of SECIS element. FIGS. 3A, 3B, and 3C thus demonstrate that chimeric SECIS elements comprising a non-canonical quartet sequence in place of a canonical quartet sequence are functional in supporting the insertion of Sec into selenoproteins.

Example 4

The 5'-UGAN-3' *Toxoplasma* Chimeric SECIS Element is Highly Efficient

Figure 14:
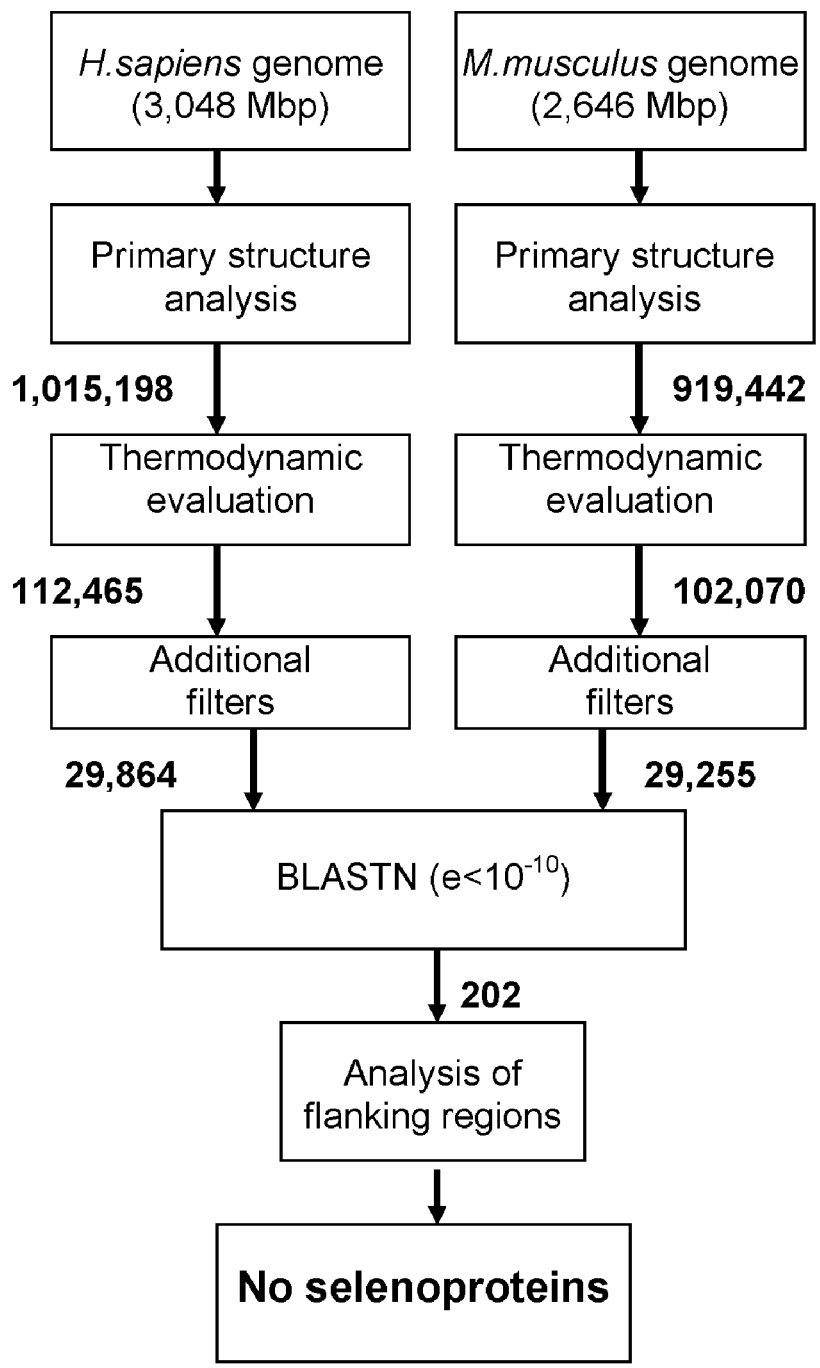
FIG. 14 shows an analysis of human and mouse genomes with a modified version of SECISearch. Each step in the procedure is shown as a separate box with the numbers shown on the left corresponding to SECIS candidates in *H. sapiens*, and those shown on the right to SECIS candidates in *M. musculus*.

The *Toxoplasma* SelT and SelS-like SECIS elements were characterized as highly efficient in Sec insertion in mammalian cells. In addition, comparison of 5' proximal 5'-UGAN-3' and 5-GGAN-3' quartet sequence forms of mammalian SECIS elements revealed that the 5'-UGAN-3' forms were more efficient. To functionally characterize 5' proximal 5'-UGAN-3' quartet sequence, *Toxoplasma* chimeric SelT and SelS-like SECIS elements (*Toxoplasma* SelT chimeric SECIS element (SEQ ID NO: 15) and *Toxoplasma* SelS-like chimeric SECIS element (SEQ ID NO: 16)), HEK 293 (FIG. 4A) and NIH 3T3 (FIG. 4B) cells were transfected with various GFP-mouse SelH (SEQ ID NO: 62 nucleotide sequence and SEQ ID NO: 63 amino acid sequence) constructs and metabolically labeled these cells with $^{75}$Se. The expected 40 kDa selenoprotein band was detected (lanes 1-10, upper panel, FIGS. 4A and 4B). For all constructs co-transfection with SBP2 increased Sec insertion (analyzed by abundance of the $^{75}$Se-labeled form and the ratio of full-length and truncated forms; FIGS. 4A and 4B, lower panel). Quantification of the bands (FIG. 14) revealed that the most efficient Sec insertion occurred in the case of the construct containing the chimeric 5' proximal 5' -TGAN-3' quartet sequence of the *Toxoplasma* SelT SECIS element (lanes 1-4, FIGS. 4A and 4B).

Example 5

Vector for Overexpression of Selenoproteins in Mammalian Cells

Figure 5A:
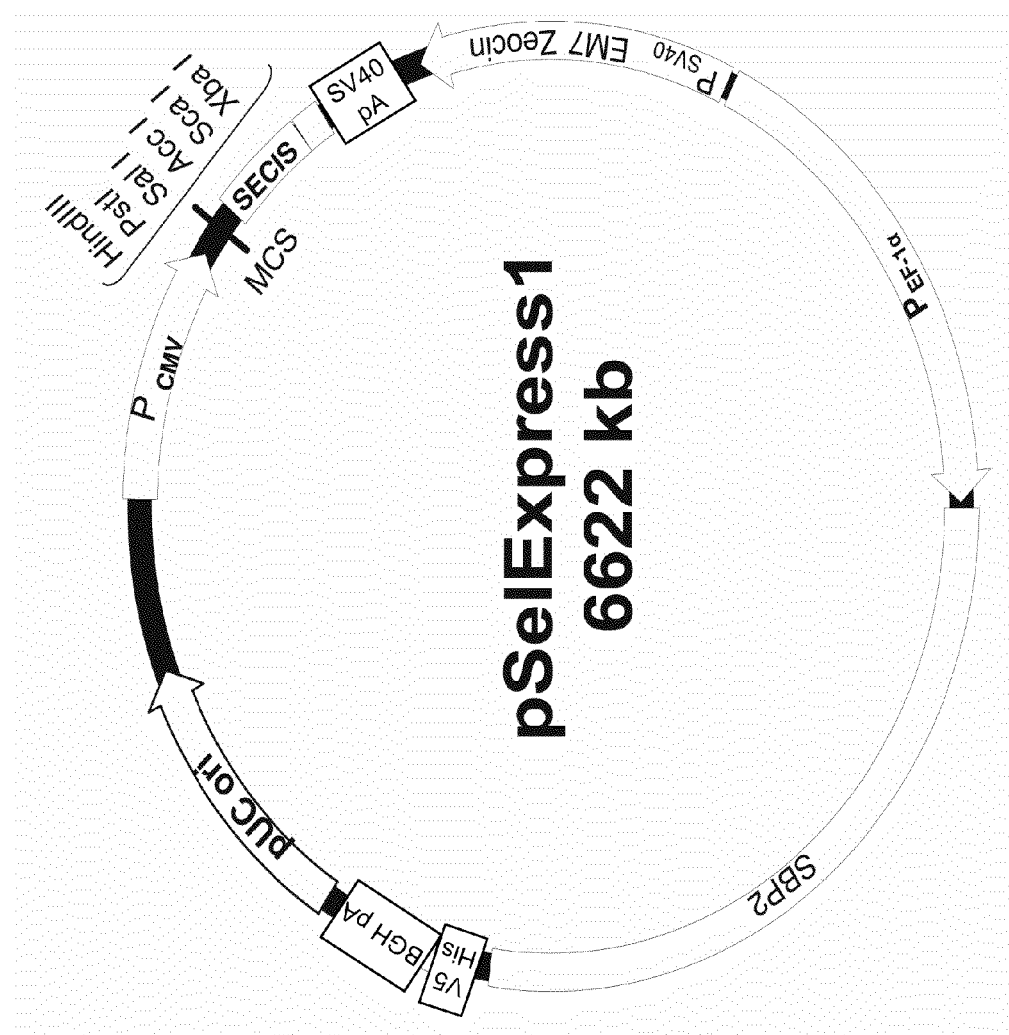
Figure 5B:
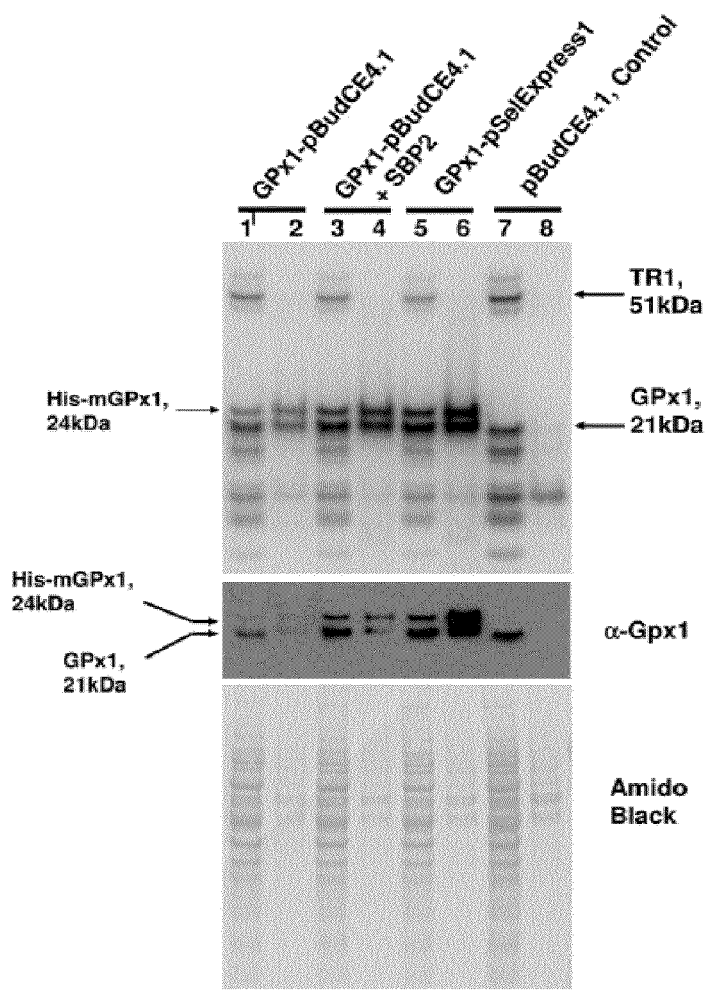

A pBudCE4.1 (Invitrogen, Carlsbad, Calif., USA) (SEQ ID NO: 17) vector designed for simultaneous expression of two genes was obtained from Invitrogen. This vector contains the human cytomegalovirus (CMV) immediate-early promoter and the human elongation factor 1α-subunit (EF-1α) promoter for high level, constitutive expression of recombinant proteins. A C-terminal functional domain of rat SBP2 was operably inserted into the vector for expression under the (EF-1α) promoter. A chimeric *Toxoplasma* SelT SECIS element comprising a 5' proximal 5'-UGAN-3' quartet sequence, immediately preceded by an A residue was operably inserted into the second cloning site for expression of a selenoprotein under the CMV promoter (FIG. 5A). The resulting expression vector was designated as pSelExpress1 (SEQ ID NO: 18). To test this vector for selenoprotein expression, a mouse glutathione peroxidase1 (GPx1) open reading frame (ORF) (SEQ ID NO: 59 nucleotide sequence and SEQ ID NO: 60 Gpx1 protein amino acid sequence) containing an N-terminal His-tag was operably inserted into pSelExpress1 and separately into a corresponding vector lacking the rat SBP2 gene. HEK 293 cells were transfected with these constructs and the cells labeled with $^{75}$Se. Recombinant GPx1 was further enriched from the transfected cells on an affinity column. The abundance of the 24 kDa GPx1 band increased in the order GPx1-pBud-*Toxoplasma* SECIS>GPx1-pBud-*Toxoplasma* SECIS+SBP2>GPx1-pSelExpress1. Samples were also probed with anti-GPx1 antibodies (FIG. 5B middle), which showed a similar pattern.

Example 6

Search for Canonical *Toxoplasma* SECIS Elements

A stand-alone version of SECISearch with the default pattern was used (Kryukov et al., 2003). The search procedure included the following steps:

A. Analysis of primary nucleotide sequence and secondary structures. PatScan (Source ?) was used to search the target database for the candidates satisfying the NUGA_AA_GA pattern. This pattern represents almost all eukaryotic SECIS elements (Johansson et al., 2005). The additional requirements were as follows: (i) distance between the quartet (NUGA) and the unpaired AA in the apical loop 10-13 nucleotides, (ii) length of the apical loop without the unpaired AA sequence 6-23 nucleotides, (iii) no more than one insertion, one deletion, and two mismatches in the stem preceding the unpaired AA, and (iv) presence of an additional stem upstream of the quartet. For each SECIS candidate found in the previous step, secondary structure was predicted and examined for consistency with the eukaryotic SECIS consensus model. Additional filters then excluded SECIS elements with more than two consecutive unpaired nucleotides and Y-shaped SECIS elements.

B. Estimation of the free energy. RNAfold from Vienna RNA package (rna.tbi.univie.ac.at) was used to calculate the free energies for whole structures and separately for their upper stem-loops. The threshold value was −12.6 kcal/mol for the whole structure and −3.7 kcal/mol for the upper stem-loop.

C. Protein identification. Analysis of location of SECIS elements and identification of ORFs were carried out. Candidate structures located on the complementary strand were filtered out.

D. ORF analysis. This final step consisted of sequence analyses of predicted open reading frames (ORFs) and identification of candidate Sec-encoding UGA codons.

Example 7

Search for Non-Canonical *Toxoplasma* SECIS Elements

A search for noncanonical SECIS elements was carried out as described in Example 6 for canonical SECIS elements, except that NUGA was replaced by NGGA in the primary sequence.

Although no non-canonical SECIS elements other than the 5'-GGGA-3'-type structures were discovered by homology searches involving known selenoproteins, the search settings were relaxed to allow any nucleotide preceding GGA (or UGA) for better sensitivity.

Example 8

Cloning Strategies

GFP-fusion constructs developed are shown in the scheme in FIG. 3A. Mouse selenoprotein H (SelH) cDNA containing the in-frame TGA codon but lacking the entire 3'UTR was amplified and cloned into pEFGP-C3 (BD Biosciences Clontech, San Jose, Calif., USA), and all subsequent constructs containing *Toxoplasma* SECIS elements were developed using this GFP-SelHΔ3'UTR fusion construct (construct 2 in FIG. 2A). *Toxoplasma* SelT and SelS-like SECIS elements (130 bp region, constructs 3 and 5, respectively, FIG. 2A) or the sequences beginning with the corresponding stop codons and containing SECIS elements (~300 bp region, constructs 4 and 6, FIG. 2A) were amplified and cloned immediately downstream of the SelH stop codon. The rationale was as follows: the SelH SECIS is located very close to the stop codon (construct 1, FIG. 2A). Therefore, the constructs having the 130 bp sequences of *Toxoplasma* SECIS elements were regarded as corresponding to substitution of the mammalian SECIS element with the *Toxoplasma* structures, whereas the constructs containing the 300 bp sequences of *Toxoplasma* SelT 3'UTR or 350 bp sequence of *Toxoplasma* SelS 3'UTRs were substitutions that introduced the corresponding 3'UTRs. The G residues in the 5' proximal quartet sequence in both *Toxoplasma* SelT and SelS-like were changed to T and the G residue immediately preceding the 5' terminus of the quartet sequence was changed to A (i.e., *Toxoplasma* 5'-GGGAN-3' to 5'-ATGAN-3' chimerics). Likewise, the corresponding AT bases in GFP-mSelHwt, GFP-mSelSwt and GFP-mSelMwt (FIG. 4A) fusion proteins were mutated to the GG (i.e., mouse 5'-ATGAN-3' to 5'-GGGAN-3' chimerics) using QuickChange mutagenesis kit (Stratagene, La Jolla, Calif., USA).

The vector for expression of selenoproteins in mammalian cells was developed on the basis of pBudCE4.1 (SEQ ID NO: 17) (Invitrogen, Carlsbad, Calif., USA). First, the C-terminal domain of rat SBP2 was cloned into the first cloning site for expression under the EF1α promoter. Subsequently, the chimeric *Toxoplasma* SelT 5'-GGGAN-3' to 5'-ATGAN-3' SECIS was cloned into the second multiple cloning site. Finally, mouse GPx1 sequence containing an in-frame TGA codon, but lacking a 3'UTR, was amplified and cloned into the vector. As a control, the construct mGPx1 -chimeric *Toxoplasma* SelT 5'-GGGAN-3' to 5'-ATGAN-3' SECIS *Toxoplasma* SelT SECIS was cloned into pBudCE4.1 that did not have the rat SBP2 sequence. To quantify the ratio of full-length and truncated forms, Scion Image 4.0 (Scion Corporation) was utilized for image processing and analysis.

Example 9

Cell Culture, Transfection and Metabolic Labeling

Mouse NIH 3T3 and human HEK 293 cells were cultured in Dulbecco's modified Eagle Medium supplemented with 10% fetal bovine serum, 100 IU/ml penicillin and 100 IU/ml streptomycin. Cells were seeded in 6-well plates and transfected as follows: NIH 3T3 cells using Lipofectamin and Plus reagent (Invitrogen, Carlsbad, Calif., USA) according to the manufacturer's protocol, and HEK 293 using the calcium-phosphate method in OPTI-MEM (Invitrogen, Carlsbad, Calif., USA), or co-transfected in a ratio of 2:1 with the rat SBP2 expression construct that was the generous gift of Drs. Paul Copeland and Donna Driscoll (Cleveland Clinic Foundation). In 12 to 24 h after transfection, the medium was replaced with DMEM supplemented with $^{75}$Se (specific activity 1,000 Ci/mmol) and the cells were incubated for an additional 12 to 24 h.

Example 10

Identification of Homologs of Known Selenoprotein Genes

A full set of known eukaryotic selenoproteins was used as query sequences and included all human selenoproteins (Hatfield and Gladyshev, 2002), all Plasmodium falciparum selenoproteins (Stadtman, 2002), *Chlamydomonas* MsrA (Rother et al., 2001), *Gallus gallus* SelU (Lescure et al., 1999), protein disulfide isomerase from *Emiliania huxleyi* (Castellano et al., 2001), and *Danio rerio* Fep15 (Kryukov et al., 2003). A stand-alone version of TBLASTN and FASTA package were used for detection of nucleotide sequences corresponding to known selenoprotein families.

Example 11

Analysis of Mammalian and Nematode Genomes, and EST Sequences

Analysis of human and mouse genomes was carried out with search patterns modified to meet the modified SECIS consensus model (e.g., GGGA-and AUGA-type SECIS elements). Likewise, similar modifications were made in the nematode search procedure (Low and Berry, 1996). In addition to completely sequenced genomes, the NCBI EST database was searched for the presence of NGGA-type SECIS elements.

Example 12

SDS/PAGE and Western Blot Analysis

After transfection, cells were washed with PBS, harvested, lysed in 200 ml of lysis buffer, electrophoresed using NuPAGE system (Invitrogen, Carlsbad, Calif., USA), and transferred onto PVDF membranes. The membranes were exposed to a PhosphorImager screen and metabolically labeled proteins were visualized using a PhosphorImager system (GE Healthcare, Piscataway, N.J., USA). The membranes were then probed with anti-GFP rabbit antiserum (Invitrogen, Carlsbad, Calif., USA) as primary and anti-rabbit HRP-conjugated antibodies as secondary antibodies. The Western blot signals were then detected with an ECL system.

Example 13

Enrichment of Recombinant His-Tagged GPx1 Protein on Metal-Affinity Resin

Forty-eight hours after transfection of mammalian cells with various His tag-GPx1 expression constructs, the cells were harvested, lysed in PBS containing protease inhibitors (complete protease mixture, Roche, Nutley, N.J., USA) by brief sonication and centrifuged for 5 min. Supernatants were collected, normalized with respect to protein concentration using Bradford method (Bio-Rad, Hercules, Calif., USA), and mixed with TALON affinity resin (Clontech, San Jose, Calif., USA). Total protein (0.75 mg; 1 mg/ml, 750 ml) per 40-50 ml of the resin was used. The samples were incubated under delicate rotation for I h at 4° C. After incubation, the resins were washed extensively, and the bound proteins were eluted by heating in an SDS/PAGE loading buffer and analyzed by gel electrophoresis and immunoblotting. After analysis of Se-labeled proteins as described above, the membranes were probed in Western blots with anti-GPx1 antibodies (GeneTex, San Antonio, Tex., USA) according to the manufacturer's protocol.

Certain biological sequences referenced herein by their "NCBI Accession Number" can be accessed through the National Center of Biotechnology Information on the world wide web at ncbi.nlm.nih.gov.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

References

1. Hatfield D L and Gladyshev V N (2002) Mol Cell Biol 22:3565-3576
2. Bock A, Rother M, Leibundgut, Ban N (2006) in Selenium. Its Molecular Biology and Role in Human Health, eds Hatfield D L, Berry M J, Gladyshev V N (Springer, N.Y.) pp 9-29
3. Stadtman T C (2002) Annu Rev Biochem 71:1-16
4. Rother M, Resch A, Wilting R, Bock A (2001) Biofactors 14:75-83
5. Lescure A, Gautheret D, Carbon P, Krol A (1999) J Biol Chem 274:38147-38154
6. Castellano S, Morozova N, Morey M, Berry M J, Serras F, Corominas M, Guigo R (2001) EMBO Rep 2:697-702
7. Kryukov G V, Castellano S, Novoselov S V, Lobanov A V, Zehtab O, Guigo R, Gladyshev V N (2003) Science 300:1439-1443
8. Johansson L, Gafvelin G, Amer E S (2005) Biochim Biophys Acta 1726:1-13
9. Berry M J, Banu L, C hen Y Y, Mandel S J, Kieffer J D, Hamey J W, Larsen P R (1991) Nature 353:273-276
10. Low S C and Berry M J (1996) Trends Biochem Sci 21:203-208
11. Berry M J, Martin G W 3rd, Low S C (1997) Biomed Environ Sci 10:182-189
12. Walczak R, Westhof E, Carbon P, Krol A (1996) RNA 2:367-379
13. Korotkov K V, Novoselov S V, Hatfield D L, Gladyshev V N (2002) Mol Cell Biol 22:1402-1411
14. Walczak R, Carbon P, Krol A (1998) RNA 4:74-84
15. Martin G W 3rd, Hamey J W, Berry M J (1996) RNA 2:171-182
16. Martin G W 3rd, Hamey J W, Berry M J (1998) RNA 4:65-73
17. Kryukov G V, Kryukov V M, Gladyshev V N (1999) J Biol Chem 274:33888-33897
18. Novoselov S V, Rao M, Onoshko N V, Zhi H, Kryukov G V, Xiang Y, Weeks D P, Hatfield D L, Gladyshev V N (2002) EMBO J 21:3681-3693
19. Zhang Y, Fomenko D E, Gladyshev V N (2005) Genome Biol 6:R37
20. Copeland P R, Fletcher J E, Carlson B A, Hatfield D L, Driscoll D M (2000) EMBO J 19:306-314
21. Low S C, Grundner-Culemann E, Hamey J W, Berry M J (2000) EMBO J 19:6882-6890
22. Fagegaltier D, Hubert N, Yamada K, Mizutani T, Carbon P, Krol A (2000) EMBO J 19:4796-4805
23. Tujebajeva R M, Copeland P R, Xu X M, Carlson B A, Harney J W, Driscoll D M, Hatfield D L, Berry M J (2000) EMBO Rep 1:158-163
24. Atkins J F and Gesteland R F (2000) Nature 407:463, 465
25. Chavatte L, Brown B A, Driscoll D M (2005) Nat Struct Mol Biol 12:408-416
26. Xu X M, Mix H, Carlson B A, Grabowski P J, Gladyshev V N, Berry M J, Hatfield D L (2005) J Biol Chem 280: 41568-41575
27. Small-Howard A, Morozova N, Stoytcheva Z, Forry E P, Mansell J B, Harney J W, Carlson B A, Xu X M, Hatfield D L, Berry M J (2006) Mol Cell Biol 26:2337-2346
28. Allmang C and Krol A (2006) in Selenium. Its Molecular Biology and Role in Human Health, eds Hatfield D L, Berry M J, Gladyshev V N (Springer, N.Y.) pp 51-63
29. Vidovic I, Nottrott S, Hartmuth K, Luhrmann R, Ficner R (2000) Mol Cell 6:1331-1342
30. Chao J A and Williamson J R (2004) Structure 12:1165-1176
31. Moore T, Zhang Y, Fenley M O, Li H (2004) Structure 12:807-818
32. Grundner-Culemann E, Martin G W 3rd, Harney J W, Berry M J (1999) RNA 5:625-635
33. Eckenroth B, Harris K, Turanov A A, Gladyshev V N, Raines R T, Hondal R J (2006) Biochemistry 45:5158-5170
34. Su D, Li Y, Gladyshev V N (2005) Nucleic Acids Res 33:2486-2492
35. Amer E S, Sarioglu H, Lottspeich F, Holmgren A, Bock A. (1999) J Mol Biol 292:1003-1016
36. Rengby O and Amer E (2007) Appl Environ Microbiol 73:432-441

What is claimed:

1. A recombinant nucleic acid construct comprising a sequence that encodes a eukaryotic selenocysteine insertion sequence (SECIS) element that is operably linked to both a heterologous expression control sequence and a heterologous sequence comprising a site for operable insertion of a heterologous nucleic acid sequence that encodes a heterologous polypeptide, said SECIS element comprising a 5' proximal 5'-GGAN-3' quartet sequence.

2. A transformed cell comprising the recombinant nucleic acid construct of claim 1.

3. A method for obtaining a selenoprotein comprising the steps of:
   (a) culturing a cell comprising a recombinant nucleic acid construct under conditions permitting expression of a selenoprotein encoded by said recombinant nucleic acid construct, said recombinant nucleic acid construct comprising a sequence that encodes a eukaryotic selenocysteine insertion sequence (SECIS) element that is operably linked to both a heterologous expression control sequence and a heterologous sequence that encodes a heterologous polypeptide containing at least one UGA codon; said SECIS element comprising a 5' proximal 5'-GGAN-3' quartet sequence; and
   (b) recovering said selenoprotein from said cell of step (a) or from a cell culture medium of step (a), thereby obtaining a selenoprotein.

4. A recombinant nucleic acid construct comprising a sequence that encodes a chimeric eukaryotic selenocysteine insertion sequence (SECIS) element that is operably linked to both a heterologous expression control sequence and a heterologous sequence comprising a site for operable insertion of a heterologous nucleic acid sequence that encodes a heterologous polypeptide, wherein a native 5' proximal 5'-GGAN-3' quartet sequence in a non-canonical SECIS element is replaced by a non-native 5' proximal 5'-UGAN-3' quartet sequence to provide said chimeric SECIS element.

5. The recombinant nucleic acid construct of claim 4, wherein said native 5' proximal 5'-GGAN-3' quartet sequence is preceded at its immediate 5'-terminus by a G residue and wherein said non-native 5' proximal 5'-UGAN-3' quartet sequence is preceded at its immediate 5'-terminus by an A residue.

6. The recombinant nucleic acid construct of claim 4, wherein said recombinant nucleic acid construct further comprises an expression cassette that provides for expression of an SBP2 protein.

7. The recombinant nucleic acid construct of claim 4, wherein said non-canonical SECIS element is selected from the group consisting of a *Toxoplasma* SelT SECIS element, a *Toxoplasma* SelS-like SECIS element, a *Neospora* SelT SECIS element, and a *Neospora* SelS-like SECIS element.

8. The recombinant nucleic acid construct of claim 4, further comprising a nucleic acid sequence that encodes a selenoprotein inserted into said site, and a polyadenylation sequence; wherein said expression control sequence, said sequence encoding a selenoprotein, said sequence encoding said eukaryotic SECIS element, and said polyadenylation sequence are operably linked.

9. The recombinant nucleic acid construct of claim 8, wherein said expression control sequence, said selenoprotein coding sequence, said sequence encoding a eukaryotic SECIS element, and said polyadenylation sequence are operably linked and comprise a first expression cassette; and wherein said recombinant nucleic acid construct further comprises a second expression cassette encoding a second heterologous protein.

10. The recombinant nucleic acid construct of claim 9, wherein said second polypeptide encoded by said second expression cassette is an SBP2 protein.

11. A transformed cell comprising the recombinant nucleic acid construct of claim 4.

12. A method for obtaining a selenoprotein comprising the steps of:
(a) culturing a cell comprising a recombinant nucleic acid construct under conditions permitting expression of a selenoprotein encoded by said recombinant nucleic acid construct, said recombinant nucleic acid construct comprising a sequence that encodes a chimeric selenocysteine insertion sequence (SECIS) element that is operably linked to both a heterologous expression control sequence and a heterologous sequence that encodes a heterologous polypeptide and contains at least one UGA codon, wherein a native 5' proximal 5'-GGAN-3' quartet sequence in a non-canonical SECIS element is replaced by a non-native 5' proximal 5'-UGAN-3' quartet sequence to provide said chimeric SECIS element; and
(b) recovering said selenoprotein from said cell of step (a) or from a cell culture medium of step (a), thereby obtaining a selenoprotein.

13. The method of claim 12, wherein said native 5' proximal 5'-GGAN-3' quartet sequence is immediately preceded by a G residue and wherein said non-native 5' proximal 5'-UGAN-3' quartet sequence is immediately preceded by an A residue.

14. The method of claim 12, wherein said recombinant nucleic acid construct comprises a first expression cassette comprising said SECIS element, said heterologous expression control sequence, and said heterologous sequence that encodes a heterologous polypeptide; and wherein said recombinant nucleic acid construct further comprises a second expression cassette that encodes a second polypeptide.

15. The method of claim 14, wherein said second polypeptide is an SBP2 protein.

16. An isolated nucleic acid comprising a heterologous coding sequence operably linked to a sequence that encodes a eukaryotic selenocysteine insertion sequence (SECIS) element, said SECIS element comprising a 5' proximal 5'-GGAN-3' quartet sequence and wherein said nucleic acid sequence comprises at least one UAG codon.

17. The isolated nucleic acid of claim 16, wherein said SECIS element is a chimeric SECIS element wherein a native 5' proximal 5'-UGAN-3' quartet sequence in a canonical eukaryotic SECIS element is replaced by a non-native 5' proximal 5'-GGAN-3' quartet sequence to provide said chimeric SECIS element.

18. An isolated nucleic acid comprising a heterologous coding sequence operably linked to a sequence that encodes a chimeric eukaryotic selenocysteine insertion sequence (SECIS) element, wherein a native 5' proximal 5'-GGAN-3' quartet sequence in a non-canonical SECIS element is replaced by a non-native 5' proximal 5'-UGAN-3' quartet sequence to provide said chimeric SECIS element wherein said nucleic acid sequence comprises at least one UAG codon.

19. The isolated nucleic acid of claim 18, wherein said native 5' proximal 5'-GGAN-3' quartet sequence is preceded at its immediate 5'-terminus by a G residue and wherein said non-native 5' proximal 5'-UGAN-3' quartet sequence is preceded at its immediate 5'-terminus by an A residue.

20. The isolated nucleic acid construct of claim 18, wherein said non-canonical SECTS element is selected from the group consisting of a *Toxoplasma* SelT SECIS element, a *Toxoplasma* SelS-like SECIS element, a *Neospora* SelT SECIS element, and a *Neospora* SelS-like SECIS element.

* * * * *

SEQUENCE LISTING

```
<160> NUMBER OF SEQ ID NOS: 67

<210> SEQ ID NO 1
<211> LENGTH: 101
<212> TYPE: DNA
<213> ORGANISM: Toxoplasma gondii

<400> SEQUENCE: 1
tcaatgagag cgcaggaaac gtggtcatga atgacgaggc acagagaaac cgttttcgga      60
tcggtgcctc tgaaaggtgg tcgacccctg cctcttacac c                        101
```

```
<210> SEQ ID NO 2
<211> LENGTH: 95
<212> TYPE: DNA
<213> ORGANISM: Toxoplasma gondii

<400> SEQUENCE: 2
ctgtagtcac acggatggct gtcgcgagtg aatgcttctc ttaaagtccc tgaccggaga      60
agcgggaaaa agtcgacagc atcctgtgtt tgcta                                95

<210> SEQ ID NO 3
<211> LENGTH: 100
<212> TYPE: DNA
<213> ORGANISM: Toxoplasma gondii

<400> SEQUENCE: 3
cgacagacga aacgaggatt tgcagcgcgt gtgacatctg tggtgtgaac agcctctgag      60
ctggagcctc agatcgacaa gcgccctggt ggggaggaga                           100

<210> SEQ ID NO 4
<211> LENGTH: 105
<212> TYPE: DNA
<213> ORGANISM: Toxoplasma gondii

<400> SEQUENCE: 4
atggtttatc acctcggata acgctgcgag ggaggatgct ggcagaaacc tctccattcg      60
aggcagctgg catctgatag ttggcttttc tgtgttgaag atcgt                     105

<210> SEQ ID NO 5
<211> LENGTH: 101
<212> TYPE: DNA
<213> ORGANISM: Toxoplasma gondii

<400> SEQUENCE: 5
tttcttaggt ttcgctctgc tgcacagcga gggacgagac tgcgccaaag cctttccgta     60
taggaggcgc cttctccgag atgctgagca gctgagtcgt t                        101

<210> SEQ ID NO 6
<211> LENGTH: 92
<212> TYPE: DNA
<213> ORGANISM: Neospora caninum

<400> SEQUENCE: 6
tgtctgcaga cgcacggaaa tctgccgcga gtgaatgctt ctcttaaagt caatgaccgg      60
ggaagcggga aatagtcgac agcgacgttt gt                                   92

<210> SEQ ID NO 7
<211> LENGTH: 98
<212> TYPE: DNA
<213> ORGANISM: Neospora caninum

<400> SEQUENCE: 7
tacgatttct gatctgggat aatgctgcga ggaggatgc tgatggaaac ctctccattc       60
gaggcagtcg gcgtctgata gttggcttaa gtcagata                             98

<210> SEQ ID NO 8
<211> LENGTH: 99
<212> TYPE: DNA
<213> ORGANISM: Neospora caninum

<400> SEQUENCE: 8
tttcagtttt tttgctctgc tgcacagcgc gggacgagac tgcgccaaag cctgcctaca      60
```

```
ggaggcgcct tctctgatat gctgagcaat tgagtgaga                                   99

<210> SEQ ID NO 9
<211> LENGTH: 91
<212> TYPE: DNA
<213> ORGANISM: Mus musculus

<400> SEQUENCE: 9
ctttcagtcc ctggagatgt tgaagcattt atgatggtgc atggccaaac ttaagctatg           60
cacctgaagc catagtttct tcctcaccag a                                          91

<210> SEQ ID NO 10
<211> LENGTH: 89
<212> TYPE: DNA
<213> ORGANISM: Mus musculus

<400> SEQUENCE: 10
tgccagcgcc ccggagacag aatgaagcgc tcagtatccc gggagcatct cccttgctga           60
gggccgacgc cagtctccaa agcaacgga                                             89

<210> SEQ ID NO 11
<211> LENGTH: 97
<212> TYPE: DNA
<213> ORGANISM: Mus musculus

<400> SEQUENCE: 11
caggatggtc tctgtgacgg gatgcgttga atgatgtctt ccttataaat ggtgaaccca           60
ccagtgagga ttactgatgt tcacagttga cggggtt                                    97

<210> SEQ ID NO 12
<211> LENGTH: 91
<212> TYPE: DNA
<213> ORGANISM: Mus musculus

<400> SEQUENCE: 12
ctttcagtcc ctggagatgt tgaagcattt gggatggtgc atggccaaac ttaagctatg           60
cacctgaagc catagtttct tcctcaccag a                                          91

<210> SEQ ID NO 13
<211> LENGTH: 89
<212> TYPE: DNA
<213> ORGANISM: Mus musculus

<400> SEQUENCE: 13
tgccagcgcc ccggagacag agggaagcgc tcagtatccc gggagcatct cccttgctga           60
gggccgacgc cagtctccaa agcaacgga                                             89

<210> SEQ ID NO 14
<211> LENGTH: 97
<212> TYPE: DNA
<213> ORGANISM: Mus musculus

<400> SEQUENCE: 14
caggatggtc tctgtgacgg gatgcgttga gggatgtctt ccttataaat ggtgaaccca           60
ccagtgagga ttactgatgt tcacagttga cggggtt                                    97

<210> SEQ ID NO 15
<211> LENGTH: 105
<212> TYPE: DNA
<213> ORGANISM: Toxoplasma gondii
```

<400> SEQUENCE: 15

```
atggtttatc acctcggata acgctgcgaa tgaggatgct ggcagaaacc tctccattcg    60
aggcagctgg catctgatag ttggcttttc tgtgttgaag atcgt                   105
```

<210> SEQ ID NO 16
<211> LENGTH: 101
<212> TYPE: DNA
<213> ORGANISM: Toxoplasma gondii

<400> SEQUENCE: 16

```
tttcttaggt ttcgctctgc tgcacagcga atgacgagac tgcgccaaag cctttccgta    60
taggaggcgc cttctccgag atgctgagca gctgagtcgt t                       101
```

<210> SEQ ID NO 17
<211> LENGTH: 4595
<212> TYPE: DNA
<213> ORGANISM: Artificial Sequence
<220> FEATURE:
<223> OTHER INFORMATION: Recombinant Artificial Vector Sequence

<400> SEQUENCE: 17

```
gcgcgcgttg acattgatta ttgactagtt attaatagta atcaattacg gggtcattag    60
ttcatagccc atatatggag ttccgcgtta cataacttac ggtaaatggc ccgcctggct   120
gaccgcccaa cgacccccgc ccattgacgt caataatgac gtatgttccc atagtaacgc   180
caatagggac tttccattga cgtcaatggg tggactattt acgtaaact gcccacttgg    240 cagtacatca agtgtatcat atgccaagta cgccccctat tgacgtcaat gacggtaaat   300
ggcccgcctg gcattatgcc cagtacatga cctatgggac ttcctact tggcagtaca    360 tctacgtatt agtcatcgct attaccatgg tgatgcggtt ttggcagtac atcaatgggc   420
gtggatagcg gtttgactca cggggatttc caagtctcca ccccattgac gtcaatggga   480
gtttgttttg gcaccaaaat caacgggact ttccaaaatg tcgtaacaac tccgccccat   540
tgacgcaaat gggcggtagg cgtgtacggt gggaggtcta taagcaga gctctctggc    600 taactagaga acccactgct tactggctta tcgaaattaa tacgactcac tatagggaga   660
cccaagcttg cattcctgca ggtcgacatc gatcttaagc agtacttcta ggatccga    720 acaaaaactc atctcagaag aggatctgaa tatgcatacc ggtcatcatc accatcacca   780
ttgagtttga tccccgggaa ttcagacatg ataagataca ttgatgagtt tggacaaacc   840
acaactagaa tgcagtgaaa aaaatgcttt atttgtgaaa tttgtgatgc tattgcttta   900
tttgtaacca ttataagctg caataaacaa gttggggtgg cgaagaact ccagcatgag    960 atccccgcgc tggaggatca tccagccggc gtcccggaaa acgattccga agcccaacct  1020
ttcatagaag gcggcggtgg aatcgaaatc tcgtagcacg tgtcagtcct gctcctcggc  1080
cacgaagtgc acgcagttgc cggccgggtc gcgcagggcg aactcccgcc cccacggctg  1140
ctcgccgatc tcggtcatgg ccggcccgga ggcgtcccgg aagttcgtgg acacgacctc  1200
cgaccactcg gcgtacagct cgtccaggcc gcgcacccac acccaggcca ggtgttgtc   1260 cggcaccacc tggtcctgga ccgcgctgat gaacagggtc acgtcgtccc ggaccacacc  1320
ggcgaagtcg tcctccacga agtcccggga gaacccgagc cggtcggtcc agaactcgac  1380
cgctccggcg acgtcgcgcg cggtgagcac cggaacggca ctggtcaact tggccatggt  1440
ttagttcctc accttgtcgt attatactat gccgatatac tatgccgatg attaattgtc  1500
aacacgtgct gatcagatcc gaaaatggat atacaagctc ccgggagctt tttgcaaaag  1560
```

```
cctaggcctc caaaaaagcc tcctcactac ttctggaata gctcagaggc agaggcggcc   1620
tcggcctctg cataaataaa aaaaattagt cagccatggg gcggagaatg ggcggaactg   1680
ggcggagtta ggggcgggat gggcggagtt aggggcggga ctatggttgc tgactaattg   1740
agatgcatgc tttgcatact tctgcctgct ggggagcctg ggactttcc acacctggtt    1800 gctgactaat tgagatgcat gctttgcata cttctgcctg ctggggagcc tggggacttt   1860
ccacaccctc gtcgagctag cttcgtgagg ctccggtgcc cgtcagtggg cagagcgcac   1920
atcgcccaca gtccccgaga agttgggggg aggggtcggc aattgaaccg gtgcctagag   1980
aaggtggcgc ggggtaaact gggaaagtga tgtcgtgtac tggctccgcc ttttccccga   2040
gggtggggga gaaccgtata taagtgcagt agtcgccgtg aacgttcttt ttcgcaacgg   2100
gtttgccgcc agaacacagg taagtgccgt gtgtggttcc cgcgggcctg gcctctttac   2160
gggttatggc ccttgcgtgc cttgaattac ttccacctgg ctccagtacg tgattcttga   2220
tcccgagctg gagccagggg cgggccttgc gctttaggag cccctttcgcc tcgtgcttga   2280 gttgaggcct ggcctgggcg ctggggccgc cgcgtgcgaa tctggtggca ccttcgcgcc   2340
tgtctcgctg ctttcgataa gtctctagcc atttaaaatt tttgatgacc tgctgcgacg   2400
ctttttttct ggcaagatag tcttgtaaat gcgggccagg atctgcacac tggtatttcg   2460
gtttttgggc ccgcggccgg cgacggggcc cgtgcgtccc agcgcacatg ttcggcgagg   2520
cggggcctgc gagcgcggcc accgagaatc ggacgggggt agtctcaagc tggccggcct   2580
gctctggtgc ctgcctcgc gccgccgtgt atcgccccgc cctgggcggc aaggctggcc    2640
cggtcggcac cagttgcgtg agcggaaaga tggccgcttc ccggccctgc tccagggggc   2700
tcaaaatgga ggacgcggcg ctcggagag cgggcgggtg agtcacccac acaaaggaaa    2760
agggcctttc cgtcctcagc cgtcgcttca tgtgactcca cggagtaccg ggcgccgtcc   2820
aggcacctcg attagttctg gagcttttgg agtacgtcgt ctttaggttg ggggagggg    2880 ttttatgcga tggagtttcc ccacactgag tgggtggaga ctgaagttag gccagcttgg   2940
cacttgatgt aattctcgtt ggaatttgcc cttttttgagt ttggatcttg gttcattctc   3000
aagcctcaga cagtggttca agttttttttt cttccatttc aggtgtcgtg aacacgtggt   3060
cgcggccgct tcgaaggtac cagcacagtg gactcgagag atctggccgg ctgggcccgt   3120
ttcgaaggta agcctatccc taaccctctc ctcggtctcg attctacgcg taccggtcat   3180
catcaccatc accattgagt ttaaacccgc tgatcagcct cgactgtgcc ttctagttgc   3240
cagccatctg ttgtttgccc ctccccgtg ccttccttga ccctggaagg tgccactccc    3300
actgtccttt cctaataaaa tgaggaaatt gcatcgcatt gtctgagtag gtgtcattct   3360
attctggggg gtgggtggg gcaggacagc aaggggagg attgggaaga caatagcagg   3420
catgctgggg atgcggtggg ctctatggct tctgaggcgg aaagaaccag tggcggtaat   3480
acggttatcc acagaatcag gggataacgc aggaaagaac atgtgagcaa aaggccagca   3540 aaaggcagg aaccgtaaaa aggccgcgtt gctggcgttt ttccataggc tccgcccccc    3600
tgacgagcat cacaaaaatc gacgctcaag tcagaggtgg cgaaacccga caggactata   3660
aagataccag gcgttttccc ctggaagctc cctcgtgcgc tctcctgttc cgaccctgcc   3720
gcttaccgga tacctgtccg cctttctccc ttcgggaagc gtggcgcttt ctcatagctc   3780
acgctgtagg tatctcagtt cggtgtaggt cgttcgctcc aagctgggct gtgtgcacga   3840 acccccccgtt cagcccgacc gctgcgcctt atccggtaac tatcgtcttg agtccaaccc   3900
ggtaagacac gacttatcgc cactggcagc agccactggt aacaggatta gcagagcgag   3960
```

```
gtatgtaggc ggtgctacag agttcttgaa gtggtggcct aactacggct acactagaag    4020
gacagtattt ggtatctgcg ctctgctgaa gccagttacc ttcggaaaaa gagttggtag    4080
ctcttgatcc ggcaaacaaa ccaccgctgg tagcggtggt ttttttgttt gcaagcagca    4140
gattacgcgc agaaaaaaag gatctcaaga agatcctttg atcttttcta cggggtctga    4200
cgctcagtgg aacgaaaact cacgttaagg gattttggtc atgacattaa cctataaaaa    4260
taggcgtatc acgaggccct ttcgtctcgc gcgtttcggt gatgacggtg aaaacctctg    4320
acacatgcag ctcccggaga cggtcacagc ttgtctgtaa gcggatgccg ggagcagaca    4380
agcccgtcag ggcgcgtcag cgggtgttgg cgggtgtcgg ggctggctta actatgcggc    4440
atcagagcag attgtactga gagtgcacca tatatgcggt gtgaaatacc gcacagatgc    4500
gtaaggagaa aataccgcat caggcgccat tcgccattca ggctgcgcaa ctgttgggaa    4560
gggcgatcgg tgcgggcctc ttcgctatta cgcca                              4595
```

<210> SEQ ID NO 18
<211> LENGTH: 6622
<212> TYPE: DNA
<213> ORGANISM: Artificial Sequence
<220> FEATURE:
<223> OTHER INFORMATION: Recombinant Artificial Vector Sequence

<400> SEQUENCE: 18

```
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgacccccgc ccattgacgt caataatgac gtatgttccc atagtaacgc     180
caatagggac tttccattga cgtcaatggg tggactattt acggtaaact gcccacttgg     240
cagtacatca agtgtatcat atgccaagta cgccccctat tgacgtcaat gacggtaaat     300
ggcccgcctg gcattatgcc cagtacatga cctttatggga cttttcctact tggcagtaca     360 tctacgtatt agtcatcgct attaccatgg tgatgcggtt ttggcagtac atcaatgggc     420
gtggatagcg gtttgactca cggggatttc caagtctcca ccccattgac gtcaatggga     480
gtttgttttg gcaccaaaat caacgggact ttccaaaatg tcgtaacaac tccgccccat     540
tgacgcaaat gggcggtagg cgtgtacggt gggaggtcta tataagcaga gctctctggc     600
taactagaga acccactgct tactggctta tcgaaattaa tacgactcac tatagggaga     660
cccaagcttg cattcctgca ggtcgacatc gatcttaagc agtacttcta gaggatcctt     720
tcatgcgggt cgcgggacga ggtatgtacg aaaaatgtgg aagtggtagt ccggcgattc     780
caatgccagc ggcttgagac tttctgtaga tccaccggaa gacgggtatg gtttatcacc     840
tcagataacg ctgcgaatga ggatgctggc agaaacctct ccattcgagg cagctggcat     900
ctgatagttg gcttttctgt gttgaagatc gtatccgcct cttgtgatct actgacagga     960
tccgaacaaa aactcatctc agaagaggat ctgaatatgc ataccggtca tcatcaccat    1020
caccattgag tttgatcccc gggaattcag acatgataag atacattgat gagtttggac    1080
aaaccacaac tagaatgcag tgaaaaaaat gctttatttg tgaaatttgt gatgctattg    1140
ctttatttgt aaccattata agctgcaata aacaagttgg ggtgggcgaa gaactccagc    1200
atgagatccc cgcgctggag gatcatccag ccggcgtccc ggaaaacgat tccgaagccc    1260
aacctttcat agaaggcggc ggtggaatcg aaatctcgta gcacgtgtca gtcctgctcc    1320
tcggccacga agtgcacgca gttgccggcc ggtcgcgca gggcgaactc ccgcccccac    1380
ggctgctcgc cgatctcggt catggccggc ccggaggcgt cccggaagtt cgtggacacg    1440
```

```
acctccgacc actcggcgta cagctcgtcc aggccgcgca cccacaccca ggccagggtg    1500
ttgtccggca ccacctggtc ctggaccgcg ctgatgaaca gggtcacgtc gtcccggacc    1560
acaccggcga agtcgtcctc cacgaagtcc cgggagaacc cgagccggtc ggtccagaac    1620
tcgaccgctc cggcgacgtc gcgcgcggtg agcaccggaa cggcactggt caacttggcc    1680
atggtttagt tcctcacctt gtcgtattat actatgccga tatactatgc cgatgattaa    1740
ttgtcaacac gtgctgatca gatccgaaaa tggatataca agctcccggg agcttttttgc   1800 aaaagcctag gcctccaaaa aagcctcctc actacttctg gaatagctca gaggcagagg    1860
cggcctcggc ctctgcataa ataaaaaaaa ttagtcagcc atggggcgga gaatgggcgg    1920
aactgggcgg agttaggggc gggatgggcg gagttagggg cgggactatg gttgctgact    1980
aattgagatg catgctttgc atacttctgc ctgctgggga gcctgggac tttccacacc     2040 tggttgctga ctaattgaga tgcatgcttt gcatacttct gcctgctggg gagcctgggg    2100
actttccaca ccctcgtcga gctagcttcg tgaggctccg gtgcccgtca gtgggcagag    2160
cgcacatcgc ccacagtccc cgagaagttg gggggagggg tcggcaattg aaccggtgcc    2220
tagagaaggt ggcgcggggt aaactgggaa agtgatgtcg tgtactggct ccgcctttt    2280 cccgagggtg ggggagaacc gtatataagt gcagtagtcg ccgtgaacgt tcttttttcgc  2340 aacgggtttg ccgccagaac acaggtaagt gccgtgtgtg gttcccgcgg gcctggcctc    2400
tttacgggtt atggcccttg cgtgccttga attacttcca cctggctcca gtacgtgatt    2460
cttgatcccg agctggagcc aggggcgggc cttgcgcttt aggagcccct tcgcctcgtg    2520
cttgagttga ggcctggcct gggcgctggg gccgccgcgt gcgaatctgg tggcaccttc    2580
gcgcctgtct cgctgctttc gataagtctc tagccattta aaattttttga tgacctgctg  2640 cgacgctttt tttctggcaa gatagtcttg taaatgcggg ccaggatctg cacactggta   2700
tttcggtttt tgggcccgcg gccggcgacg gggcccgtgc gtcccagcgc acatgttcgg    2760
cgaggcgggg cctgcgagcg cggccaccga gaatcggacg ggggtagtct caagctggcc    2820
ggcctgctct ggtgcctggc ctcgcgccgc cgtgtatcgc cccgccctgg gcggcaaggc    2880
tggcccggtc ggcaccagtt gcgtgagcgg aaagatggcc gcttccggc cctgctccag     2940 ggggctcaaa atggaggacg cggcgctcgg gagagcgggc gggtgagtca cccacacaaa    3000
ggaaaagggc cttttccgtcc tcagccgtcg cttcatgtga ctccacggag taccgggcgc   3060
cgtccaggca cctcgattag ttctggagct tttggagtac gtcgtcttta ggttgggggg    3120
aggggtttta tgcgatggag tttccccaca ctgagtgggt ggagactgaa gttaggccag    3180
cttggcactt gatgtaattc tcgttggaat ttgcccttttt tgagtttgga tcttggttca   3240
ttctcaagcc tcagacagtg gttcaaagtt ttttcttcc atttcaggtg tcgtgaacac     3300
gtggtcgcgg ccgcatgtct ctcctgggag aagcgggcaa gccagttgca gatatggtag    3360
agggtaaaat ggtgaagacg gatcacactg atggagctgt gactaacaat gccgctacca    3420
gttccccctc gtgtacacga gagttgtctt ggacaccaat gggttatatt gttcggcaga    3480
cagtgtcttc agactcagca gcagcgactg aaactgttaa ttccatcata aacctaaaga    3540
agactacgtc atcagctgat gctaaaaacg ttagcgtgac atctgaggcg ttatcttcag    3600
atccttcctt cagcagggaa aagcgtgttc atcctggtcc aaaggccaaa gcatcacaag    3660
gaagtgaact tgaacaaaac gaaagctcca aaagaataa gaaaaagaaa gaaaagtcta    3720
aatcaagtta tgaagtcctg ccggttcagg agccaccgag gattgaagat gctgaggaat    3780
tccccaacct gtcagttgca tctgaaagaa gacacagagg ggaatcacca aaacttcaga    3840
```

```
gtaaacagca ggcgcagaat gactttaaaa cgggtggaaa gaagagccag gttccggtgc    3900
agctggacct gggggggcatg ttggcagcac tggagaagca gcagcacgcc ccgcacgcca    3960
agccatcctc cagacccgtc gtgttctcag ttggagcagt gccagtcctt tccaaggatg    4020
cctcctcagg tgagaggggt cgccgctcta gtcaggtgaa gaccccacac aaccccctgg    4080
actccagtgc cccctaatg aagaagggga agcagaggga gatacctaag gccaagaagc    4140
ccacctcact gaagaagata attttgaaag aacggcaaga gagaatgcag cagcgactcc    4200
aagaaagtgc tgtgagcccg actgtggcca gtgatgactc acaggatgtg gagagtggtg    4260
ttactaacca aatccccagc ccggacaacc ccacaggtcc agagaagaca gaagaaccca    4320
tgtcttctac acctgtggtt gagggtgagt cagaagagcc agctggcaca gagttccaga    4380
gggacccaga ggcttgccag cctgcccctg acagtgccac cttccccaag atccacagcc    4440
ggaggttccg ggactactgc agccagatgc ttagtaaaga agtcgatgct tgtgtcacgg    4500
gtctcctcaa ggaactggtg cgcttccaag accggatgta ccagaaggat cctgtcaagg    4560
ccaagacaaa acgccggctt gtgctggggc tgagggaggt cctgaaacac ctgaagctca    4620
ggaagctgaa gtgtatcatc atctctccca actgtgagaa gacacagtct aaaggtggac    4680
tggacgacac actgcacacc atcatcgatt gcgcctgtga gcagaacatc ccctttgtgt    4740
ttgcactcaa ccgcaaggca ctggggcgga gtctgaataa agcagttcct gtcagcattg    4800
tagggatctt cagttacgat ggggcccagg accagttcca caagatggtt gagctgacca    4860
tggcagcccg tcaggcatac aagaccatgt tggagacgat gcggcaggag caggcaggag    4920
aacctgggcc tcagaccct cccagcccac ccatgcagga ccccatccag tccaccgacg    4980
aaggcaccct agcttccact ggagaagagc cacactatat tgagatttgg agaaagcatc    5040
tggaagcgta cagtcagcat gccctggagc tggaagactc actggaggca tcaacctctc    5100
agatgatgaa cttgaattc tcagagatc tggccggctg ggcccgtttc gaaggtaagc    5160
ctatccctaa ccctctcctc ggtctcgatt ctacgcgtac cggtcatcat caccatcacc    5220
attgagttta aacccgctga tcagcctcga ctgtgccttc tagttgccag ccatctgttg    5280 tttgccctc ccccgtgcct tccttgaccc tggaaggtgc cactcccact gtccttct    5340 aataaaatga ggaaattgca tcgcattgtc tgagtaggtg tcattctatt ctgggggtg    5400 gggtggggca ggacagcaag ggggaggatt gggaagacaa tagcaggcat gctggggatg    5460
cggtgggctc tatggcttct gaggcggaaa gaaccagtgg cggtaatacg gttatccaca    5520
gaatcagggg ataacgcagg aaagaacatg tgagcaaaag gccagcaaaa ggccaggaac    5580
cgtaaaaagg ccgcgttgct ggcgtttttc cataggctcc gccccctga cgagcatcac    5640 aaaaatcgac gctcaagtca gaggtggcga aacccgacag gactataaag ataccaggcg    5700
tttccccctg gaagctccct cgtgcgctct cctgttccga ccctgccgct taccggatac    5760
ctgtccgcct ttctcccttc gggaagcgtg gcgctttctc atagctcacg ctgtaggtat    5820
ctcagttcgg tgtaggtcgt tcgctccaag ctgggctgtg tgcacgaacc ccccgttcag    5880
cccgaccgct gcgccttatc cggtaactat cgtcttgagt ccaacccggt aagacacgac    5940
ttatcgccac tggcagcagc cactggtaac aggattagca gagcgaggta tgtaggcggt    6000
gctacagagt tcttgaagtg gtggcctaac tacggctaca ctagaaggac agtatttggt    6060
atctgcgctc tgctgaagcc agttaccttc ggaaaaagag ttggtagctc ttgatccggc    6120
aaacaaacca ccgctggtag cggtggtttt tttgtttgca agcagcagat tacgcgcaga    6180
aaaaaaggat ctcaagaaga tcctttgatc ttttctacgg ggtctgacgc tcagtggaac    6240
```

```
gaaaactcac gttaagggat tttggtcatg acattaacct ataaaaatag gcgtatcacg      6300
aggccctttc gtctcgcgcg tttcggtgat gacggtgaaa acctctgaca catgcagctc      6360
ccggagacgg tcacagcttg tctgtaagcg gatgccggga gcagacaagc ccgtcagggc      6420
gcgtcagcgg gtgttggcgg gtgtcggggc tggcttaact atgcggcatc agagcagatt      6480
gtactgagag tgcaccatat atgcggtgtg aaataccgca cagatgcgta aggagaaaat      6540
accgcatcag gcgccattcg ccattcaggc tgcgcaactg ttgggaaggg cgatcggtgc      6600
gggcctcttc gctattacgc ca                                               6622

<210> SEQ ID NO 19
<211> LENGTH: 2541
<212> TYPE: DNA
<213> ORGANISM: Rattus norvegicus

<400> SEQUENCE: 19
atggcgtcgg agcggccgcg ggagcccgaa ggcgaggata gcatcaagtt gtcagctgat        60
gtcaaaccat ttgtccctaa gtttgctggg ctcaatgtgg cgtggtcaga gtcctcagaa       120
gcttgtgtct tcccaggctg tgcagccact tactatccat tcgtacagga gtcaccagcg       180
gctgaacaaa aaatgtatcc tgaagacatg gcttttggag cccctgcctt tccagcacag       240
tacgtgtctt ctgagatagc actgcatcct tttgcctatc ccacttacgc cctcgagtcc       300
acacagagtg tttgctcagt gccaaccctg cagtacgatt acagccaagc acagtgtcac       360
ccaggctttc ggccagcaaa gccccgaaat gagcacgcat gccctcctca ggaagcaaag       420
tgtgtattta agaaaaaatc ctctgatgag agaagagcat gggaagagca aaagtcaagc       480
aacagaaggg ctgatggtgc agtgccctgt gaggcgagac cagccagagg gtcatgccac       540
ctgaaatctg atggttatca caagcggcct gatcggaagt ccaggatcct tacaaaaagt       600
gcatctacct ctaaacccga atttgaattt agcaggttgg actttcctga actgcagagt       660
ccaaagaaca gtaatctgcc agagacacag aagcagccca ggtgggggcc tcttggccct       720
gctgccagta acatgtctct cctgggagaa gcgggcaagc cagttgcaga tatggtagag       780
ggtaaaatgg tgaagacgga tcacactgat ggagctgtga ctaacaatgc cgctaccagt       840
tccccctcgt gtacacgaga gttgtcttgg acaccaatgg gttatattgt tcggcagaca       900
gtgtcttcag actcagcagc agcgactgaa actgttaatt ccatcataaa cctaaagaag       960
actacgtcat cagctgatgc taaaaacgtt agcgtgacat ctgaggcgtt atcttcagat      1020
ccttccttca gcagggaaaa gcgtgttcat cctggtccaa aggccaaagc atcacaagga      1080
agtgaacttg aacaaaacga aagctccaaa agaataaga aaaagaaaga aaagtctaaa       1140
tcaagttatg aagtcctgcc ggttcaggag ccaccgagga ttgaagatgc tgaggaattc      1200
cccaacctgt cagttgcatc tgaaagaaga cacagagggg aatcaccaaa acttcagagt      1260
aaacagcagg cgcagaatga cttaaaacg ggtggaaaga gagccaggt tccggtgcag        1320 ctggacctgg ggggcatgtt ggcagcactg gagaagcagc agcacgcccc gcacgccaag      1380
ccatcctcca gacccgtcgt gttctcagtt ggagcagtgc cagtcctttc caaggatgcc      1440
tcctcaggtg agaggggtcg ccgctctagt caggtgaaga ccccacacaa cccccctggac     1500 tccagtgccc cctaatgaa gaaggggaag cagagggaga tacctaaggc caagaagccc       1560
acctcactga agaagataat tttgaaagaa cggcaagaga gaatgcagca gcgactccaa      1620
gaaagtgctg tgagcccgac tgtggccagt gatgactcac aggatgtgga gagtggtgtt      1680
actaaccaaa tccccagccc ggacaacccc acaggtccag agaagacaga gaacccatg       1740
```

```
tcttctacac ctgtggttga gggtgagtca gaagagccag ctggcacaga gttccagagg    1800
gacccagagg cttgccagcc tgcccctgac agtgccacct tccccaagat ccacagccgg    1860
aggttccggg actactgcag ccagatgctt agtaaagaag tcgatgcttg tgtcacgggt    1920
ctcctcaagg aactggtgcg cttccaagac cggatgtacc agaaggatcc tgtcaaggcc    1980
aagacaaaac gccggcttgt gctggggctg agggaggtcc tgaaacacct gaagctcagg    2040
aagctgaagt gtatcatcat ctctcccaac tgtgagaaga cacagtctaa aggtggactg    2100
gacgacacac tgcacaccat catcgattgc gcctgtgagc agaacatccc ctttgtgttt    2160
gcactcaacc gcaaggcact ggggcggagt ctgaataaag cagttcctgt cagcattgta    2220
gggatcttca gttacgatgg ggcccaggac cagttccaca agatggttga gctgaccatg    2280
gcagcccgtc aggcatacaa gaccatgttg gagacgatgc ggcaggagca ggcaggagaa    2340
cctgggcctc agaccctcc cagcccaccc atgcaggacc ccatccagtc caccgacgaa    2400
ggcaccctag cttccactgg agaagagcca cactatattg agatttggag aaagcatctg    2460
gaagcgtaca gtcagcatgc cctggagctg aagactcac tggaggcatc aacctctcag    2520
atgatgaact tgaatttata a                                              2541

<210> SEQ ID NO 20
<211> LENGTH: 846
<212> TYPE: PRT
<213> ORGANISM: Rattus norvegicus

<400> SEQUENCE: 20

Met Ala Ser Glu Arg Pro Arg Glu Pro Glu Gly Asp Ser Ile Lys
1               5                   10                  15

Leu Ser Ala Asp Val Lys Pro Phe Val Pro Lys Phe Ala Gly Leu Asn
                20                  25                  30

Val Ala Trp Ser Glu Ser Ser Glu Ala Cys Val Phe Pro Gly Cys Ala
            35                  40                  45

Ala Thr Tyr Tyr Pro Phe Val Gln Glu Ser Pro Ala Ala Glu Gln Lys
        50                  55                  60

Met Tyr Pro Glu Asp Met Ala Phe Gly Ala Pro Ala Phe Pro Ala Gln
65                  70                  75                  80

Tyr Val Ser Ser Glu Ile Ala Leu His Pro Phe Ala Tyr Pro Thr Tyr
                85                  90                  95

Ala Leu Glu Ser Thr Gln Ser Val Cys Ser Val Pro Thr Leu Gln Tyr
            100                 105                 110

Asp Tyr Ser Gln Ala Gln Cys His Pro Gly Phe Arg Pro Ala Lys Pro
        115                 120                 125

Arg Asn Glu His Ala Cys Pro Pro Gln Glu Ala Lys Cys Val Phe Lys
    130                 135                 140

Lys Lys Ser Ser Asp Glu Arg Arg Ala Trp Glu Glu Gln Lys Ser Ser
145                 150                 155                 160

Asn Arg Arg Ala Asp Gly Ala Val Pro Cys Glu Ala Arg Pro Ala Arg
                165                 170                 175

Gly Ser Cys His Leu Lys Ser Asp Gly Tyr His Lys Arg Pro Asp Arg
            180                 185                 190

Lys Ser Arg Ile Leu Thr Lys Ser Ala Ser Thr Ser Lys Pro Glu Phe
        195                 200                 205

Glu Phe Ser Arg Leu Asp Phe Pro Glu Leu Gln Ser Pro Lys Asn Ser
    210                 215                 220

Asn Leu Pro Glu Thr Gln Lys Gln Pro Arg Trp Gly Pro Leu Gly Pro
```

```
            225                 230                 235                 240
Ala Ala Ser Asn Met Ser Leu Leu Gly Glu Ala Gly Lys Pro Val Ala
                245                 250                 255
Asp Met Val Glu Gly Lys Met Val Lys Thr Asp His Thr Asp Gly Ala
                260                 265                 270
Val Thr Asn Asn Ala Ala Thr Ser Ser Pro Ser Cys Thr Arg Glu Leu
                275                 280                 285
Ser Trp Thr Pro Met Gly Tyr Ile Val Arg Gln Thr Val Ser Ser Asp
        290                 295                 300
Ser Ala Ala Thr Glu Thr Val Asn Ser Ile Ile Asn Leu Lys Lys
305                 310                 315                 320
Thr Thr Ser Ser Ala Asp Ala Lys Asn Val Ser Val Thr Ser Glu Ala
                325                 330                 335
Leu Ser Ser Asp Pro Ser Phe Ser Arg Glu Lys Arg Val His Pro Gly
                340                 345                 350
Pro Lys Ala Lys Ala Ser Gln Gly Ser Glu Leu Glu Gln Asn Glu Ser
                355                 360                 365
Ser Lys Lys Asn Lys Lys Lys Glu Lys Ser Lys Ser Ser Tyr Glu
        370                 375                 380
Val Leu Pro Val Gln Glu Pro Pro Arg Ile Glu Asp Ala Glu Glu Phe
385                 390                 395                 400
Pro Asn Leu Ser Val Ala Ser Glu Arg Arg His Arg Gly Glu Ser Pro
                405                 410                 415
Lys Leu Gln Ser Lys Gln Gln Ala Gln Asn Asp Phe Lys Thr Gly Gly
                420                 425                 430
Lys Lys Ser Gln Val Pro Val Gln Leu Asp Leu Gly Gly Met Leu Ala
                435                 440                 445
Ala Leu Glu Lys Gln Gln His Ala Pro His Ala Lys Pro Ser Ser Arg
        450                 455                 460
Pro Val Val Phe Ser Val Gly Ala Val Pro Val Leu Ser Lys Asp Ala
465                 470                 475                 480
Ser Ser Gly Glu Arg Gly Arg Arg Ser Ser Gln Val Lys Thr Pro His
                485                 490                 495
Asn Pro Leu Asp Ser Ser Ala Pro Leu Met Lys Lys Gly Lys Gln Arg
                500                 505                 510
Glu Ile Pro Lys Ala Lys Lys Pro Thr Ser Leu Lys Lys Ile Ile Leu
        515                 520                 525
Lys Glu Arg Gln Glu Arg Met Gln Gln Arg Leu Gln Glu Ser Ala Val
        530                 535                 540
Ser Pro Thr Val Ala Ser Asp Ser Gln Asp Val Glu Ser Gly Val
545                 550                 555                 560
Thr Asn Gln Ile Pro Ser Pro Asp Asn Pro Thr Gly Pro Glu Lys Thr
                565                 570                 575
Glu Glu Pro Met Ser Ser Thr Pro Val Val Gly Gly Ser Glu Glu
                580                 585                 590
Pro Ala Gly Thr Glu Phe Gln Arg Asp Pro Glu Ala Cys Gln Pro Ala
                595                 600                 605
Pro Asp Ser Ala Thr Phe Pro Lys Ile His Ser Arg Arg Phe Arg Asp
        610                 615                 620
Tyr Cys Ser Gln Met Leu Ser Lys Glu Val Asp Ala Cys Val Thr Gly
625                 630                 635                 640
Leu Leu Lys Glu Leu Val Arg Phe Gln Asp Arg Met Tyr Gln Lys Asp
                645                 650                 655
```

```
Pro Val Lys Ala Lys Thr Lys Arg Arg Leu Val Leu Gly Leu Arg Glu
            660                 665                 670

Val Leu Lys His Leu Lys Leu Arg Lys Leu Lys Cys Ile Ile Ile Ser
        675                 680                 685

Pro Asn Cys Glu Lys Thr Gln Ser Lys Gly Gly Leu Asp Asp Thr Leu
690                 695                 700

His Thr Ile Ile Asp Cys Ala Cys Glu Gln Asn Ile Pro Phe Val Phe
705                 710                 715                 720

Ala Leu Asn Arg Lys Ala Leu Gly Arg Ser Leu Asn Lys Ala Val Pro
                725                 730                 735

Val Ser Ile Val Gly Ile Phe Ser Tyr Asp Gly Ala Gln Asp Gln Phe
            740                 745                 750

His Lys Met Val Glu Leu Thr Met Ala Ala Arg Gln Ala Tyr Lys Thr
        755                 760                 765

Met Leu Glu Thr Met Arg Gln Glu Gln Ala Gly Glu Pro Gly Pro Gln
770                 775                 780

Thr Pro Pro Ser Pro Pro Met Gln Asp Pro Ile Gln Ser Thr Asp Glu
785                 790                 795                 800

Gly Thr Leu Ala Ser Thr Gly Glu Glu Pro His Tyr Ile Glu Ile Trp
                805                 810                 815

Arg Lys His Leu Glu Ala Tyr Ser Gln His Ala Leu Glu Leu Glu Asp
            820                 825                 830

Ser Leu Glu Ala Ser Thr Ser Gln Met Met Asn Leu Asn Leu
        835                 840                 845

<210> SEQ ID NO 21
<211> LENGTH: 2577
<212> TYPE: DNA
<213> ORGANISM: Mus musculus

<400> SEQUENCE: 21
atggcgtcgg agcggccgcg ggagccggac ggcgaggata gcatcaagtt gtcagctgat     60
gtcaaaccat cgtccctaa gtttgctggg ctcaacgtgg cgtggtcaga gtcctcagag     120
acacgtgtct tcccaggctg tgcggccacc tactatccat tgtacagga accaccagca    180 gctgaacaga aaatgtatcc cgaagacatg gctttcggag cccccacctt tccagcacag    240
tacgtgtctt ctgagatagc gctgcatcct tttgcctatc ccacttacac cctagagtcc    300
gcacagagtg tttgctcagt gccaaccctg cagtacgact acagccaagc acggtgtcac    360
ccaggctttc ggacagcaaa gccccggcat gagcacgtgt gccctccacc tcaggaagca    420
aaaggtgtat ttaagaaaaa accctctgat gagagaagag catgtgaaga gcaaaagtca    480
agcagcagaa gggctgacaa tgcggtgccc tgtgaggcga ccagccag gggtccagt      540 cacctgtcct ctcgaactga gagcagtttg aaatctgatg ttaccacaa gcgacccgac    600 cgcaagtcca gaatccttgc gaagagtgca tctacctcta aacctgaatt tgagtttagt    660
aggttagact ttcctgaact gcagagtcca agaacagta acatgccaga gacacagaag    720
ccgcccaggt gggggcctct tggccctgct gccagtaaca tgcctctcct aggagacgtc    780
ggcaagcccg tcgcagatat ggtagagggc aaaatggtga gagcgatca cactgatgga    840 gctgtgacca gtaatgccac taccagttcc ccttcatgta cccaagagtt gtcttggaca    900
ccaatgggtt atattgttcg gcagacagtg tcttcagatt cagcagcagc cactgaaaat    960
gtgacttcca tgataaacct aaagaagact acttcatcag ctgatgctaa aaatgttagt   1020
gtgacatctg aggctttatc ttcaaatcct tcctacaaca gagaaaagcg tgtttatcct   1080
```

```
gctccaaagg ccaaagcatc acaaggaggt gaacttgaac aaaacgaaag ctccaaaaag    1140
aataagaaaa agaagagaa gtctaaaccg agttatgaag tcctgacggt tcaggagccg    1200
ccaaggattg aagatgcaga ggaattcccc aacctgtcag ttgcgtcgga agaagacac    1260
agagggcaat caccgaagct tcacagtaaa cagcagacgc agaatgaatt taaaacaagt    1320
gggaagaaga gccaggtccc agtgcagctg gacctggggg gcatgctggc cgcgctggag    1380
aagcagcagc agcagcagca cgcctcgcac gccaagccat cctccagacc cgtcgtgttc    1440
tcagttggag cagtgccagt cctgtccaag gatgcctcct ccagtgagag gggacgccgc    1500
tccagtcaga tgaagacccc acacaacccc ctggactcca gtgccccct gatgaagaag    1560
gggaagcaga gggagatacc taaggccaag aagcccacct cactgaagaa gataattttg    1620
aaagaacggc aagagaggat gcagcagcga ctccaagaaa gtgctgtgag cctgacggtg    1680
gccagtgatg actcacagga tgtggagagt ggcgccagta accaaacccc cagtcaggac    1740
aaccccacag gtccagagaa acagaagaa tcagtgtctt ctacacctgt ggttgagggt    1800
gagtcagagg agccagctgg cacagagttc cagagggacc cagaggcttg ccagcctgcc    1860
cctgacagtg ccaccttccc caagatccac agccggaggt tccgggacta ctgcagccag    1920
atgcttagta agaagtaga tgcttgtgtc acgggtctgc tcaaggagct ggtgcgcttc    1980
caagaccgca tgtaccagaa ggatcccgtc aaggccaaga caaaacgcg ctcgtgctg    2040
gggctgaggg aggtcctgaa acacctgaag ctcaggaagc tgaagtgcat catcatctct    2100
cccaactgtg agaagaccca gtctaaaggt gggctggacg acacgctgca caccatcatc    2160
gactgcgcct gcgagcagaa catcccttc gtgtttgcac tcaatcgcaa ggctctgggg    2220
cggagcctga ataagctgt tcctgtcagc attgtaggga tcttcagcta cgatggggcc    2280
caggaccagt tccacaagat ggttgagctg accatggcag cccgtcaggc atacaagacc    2340
atgttggaga caatgcggca ggaacaggca ggagaacctg acctcagtc ccctcccagc    2400
ccacccatgc aagaccccat ccatccacg gaagaaggca ccctcccttc cactggagaa    2460
gagccacact acattgagat ttggaaaaag cacctggaag cgtacagtca gcgtgccctg    2520
gagctggaag actcactgga ggcgtcaacc tctcagatga tgaacttgaa tttataa    2577
```

<210> SEQ ID NO 22
<211> LENGTH: 858
<212> TYPE: PRT
<213> ORGANISM: Mus musculus

<400> SEQUENCE: 22

```
Met Ala Ser Glu Arg Pro Arg Glu Pro Asp Gly Glu Asp Ser Ile Lys
1               5                   10                  15

Leu Ser Ala Asp Val Lys Pro Phe Val Pro Lys Phe Ala Gly Leu Asn
            20                  25                  30

Val Ala Trp Ser Glu Ser Glu Thr Arg Val Phe Pro Gly Cys Ala
        35                  40                  45

Ala Thr Tyr Tyr Pro Phe Val Gln Glu Pro Ala Ala Glu Gln Lys
    50                  55                  60

Met Tyr Pro Glu Asp Met Ala Phe Gly Ala Pro Thr Phe Pro Ala Gln
65              70                  75                  80

Tyr Val Ser Ser Glu Ile Ala Leu His Pro Phe Ala Tyr Pro Thr Tyr
                85                  90                  95

Thr Leu Glu Ser Ala Gln Ser Val Cys Ser Val Pro Thr Leu Gln Tyr
            100                 105                 110

Asp Tyr Ser Gln Ala Arg Cys His Pro Gly Phe Arg Thr Ala Lys Pro
```

```
                  115                 120                 125
Arg His Glu His Val Cys Pro Pro Gln Glu Ala Lys Gly Val Phe
130                 135                 140
Lys Lys Lys Pro Ser Asp Glu Arg Arg Ala Cys Glu Glu Gln Lys Ser
145                 150                 155                 160
Ser Ser Arg Arg Ala Asp Asn Ala Val Pro Cys Glu Ala Arg Pro Ala
                    165                 170                 175
Arg Gly Ser Ser His Leu Ser Ser Arg Thr Glu Ser Ser Leu Lys Ser
                    180                 185                 190
Asp Gly Tyr His Lys Arg Pro Asp Arg Lys Ser Arg Ile Leu Ala Lys
                195                 200                 205
Ser Ala Ser Thr Ser Lys Pro Glu Phe Glu Phe Ser Arg Leu Asp Phe
210                 215                 220
Pro Glu Leu Gln Ser Pro Lys Asn Ser Asn Met Pro Glu Thr Gln Lys
225                 230                 235                 240
Pro Pro Arg Trp Gly Pro Leu Gly Pro Ala Ala Ser Asn Met Pro Leu
                    245                 250                 255
Leu Gly Asp Val Gly Lys Pro Val Ala Asp Met Val Glu Gly Lys Met
                260                 265                 270
Val Lys Ser Asp His Thr Asp Gly Ala Val Thr Ser Asn Ala Thr Thr
                275                 280                 285
Ser Ser Pro Ser Cys Thr Gln Glu Leu Ser Trp Thr Pro Met Gly Tyr
290                 295                 300
Ile Val Arg Gln Thr Val Ser Ser Asp Ser Ala Ala Ala Thr Glu Asn
305                 310                 315                 320
Val Thr Ser Met Ile Asn Leu Lys Lys Thr Thr Ser Ser Ala Asp Ala
                    325                 330                 335
Lys Asn Val Ser Val Thr Ser Glu Ala Leu Ser Ser Asn Pro Ser Tyr
                    340                 345                 350
Asn Arg Glu Lys Arg Val Tyr Pro Ala Pro Lys Ala Lys Ala Ser Gln
                355                 360                 365
Gly Gly Glu Leu Glu Gln Asn Glu Ser Ser Lys Lys Asn Lys Lys Lys
                370                 375                 380
Lys Glu Lys Ser Lys Pro Ser Tyr Glu Val Leu Thr Val Gln Glu Pro
385                 390                 395                 400
Pro Arg Ile Glu Asp Ala Glu Glu Phe Pro Asn Leu Ser Val Ala Ser
                    405                 410                 415
Glu Arg Arg His Arg Gly Gln Ser Pro Lys Leu His Ser Lys Gln Gln
                    420                 425                 430
Thr Gln Asn Glu Phe Lys Thr Ser Gly Lys Lys Ser Gln Val Pro Val
                    435                 440                 445
Gln Leu Asp Leu Gly Gly Met Leu Ala Ala Leu Glu Lys Gln Gln Gln
                450                 455                 460
Gln Gln His Ala Ser His Ala Lys Pro Ser Ser Arg Pro Val Val Phe
465                 470                 475                 480
Ser Val Gly Ala Val Pro Val Leu Ser Lys Asp Ala Ser Ser Ser Glu
                    485                 490                 495
Arg Gly Arg Arg Ser Ser Gln Met Lys Thr Pro His Asn Pro Leu Asp
                    500                 505                 510
Ser Ser Ala Pro Leu Met Lys Lys Gly Lys Gln Arg Glu Ile Pro Lys
                    515                 520                 525
Ala Lys Lys Pro Thr Ser Leu Lys Lys Ile Ile Leu Lys Glu Arg Gln
                530                 535                 540
```

Glu Arg Met Gln Gln Arg Leu Gln Glu Ser Ala Val Ser Leu Thr Val
545                 550                 555                 560

Ala Ser Asp Asp Ser Gln Asp Val Glu Ser Gly Ala Ser Asn Gln Thr
                565                 570                 575

Pro Ser Gln Asp Asn Pro Thr Gly Pro Glu Lys Thr Glu Glu Ser Val
            580                 585                 590

Ser Ser Thr Pro Val Val Glu Gly Ser Glu Glu Pro Ala Gly Thr
        595                 600                 605

Glu Phe Gln Arg Asp Pro Glu Ala Cys Gln Pro Ala Pro Asp Ser Ala
610                 615                 620

Thr Phe Pro Lys Ile His Ser Arg Arg Phe Arg Asp Tyr Cys Ser Gln
625                 630                 635                 640

Met Leu Ser Lys Glu Val Asp Ala Cys Val Thr Gly Leu Leu Lys Glu
                645                 650                 655

Leu Val Arg Phe Gln Asp Arg Met Tyr Gln Lys Asp Pro Val Lys Ala
            660                 665                 670

Lys Thr Lys Arg Arg Leu Val Leu Gly Leu Arg Glu Val Leu Lys His
        675                 680                 685

Leu Lys Leu Arg Lys Leu Lys Cys Ile Ile Ser Pro Asn Cys Glu
690                 695                 700

Lys Thr Gln Ser Lys Gly Gly Leu Asp Asp Thr Leu His Thr Ile Ile
705                 710                 715                 720

Asp Cys Ala Cys Glu Gln Asn Ile Pro Phe Val Phe Ala Leu Asn Arg
                725                 730                 735

Lys Ala Leu Gly Arg Ser Leu Asn Lys Ala Val Pro Val Ser Ile Val
            740                 745                 750

Gly Ile Phe Ser Tyr Asp Gly Ala Gln Asp Gln Phe His Lys Met Val
        755                 760                 765

Glu Leu Thr Met Ala Ala Arg Gln Ala Tyr Lys Thr Met Leu Glu Thr
770                 775                 780

Met Arg Gln Glu Gln Ala Gly Glu Pro Gly Pro Gln Ser Pro Pro Ser
785                 790                 795                 800

Pro Pro Met Gln Asp Pro Ile Pro Ser Thr Glu Glu Gly Thr Leu Pro
                805                 810                 815

Ser Thr Gly Glu Glu Pro His Tyr Ile Glu Ile Trp Lys Lys His Leu
            820                 825                 830

Glu Ala Tyr Ser Gln Arg Ala Leu Glu Leu Glu Asp Ser Leu Glu Ala
        835                 840                 845

Ser Thr Ser Gln Met Met Asn Leu Asn Leu
850                 855

<210> SEQ ID NO 23
<211> LENGTH: 2565
<212> TYPE: DNA
<213> ORGANISM: Homo sapiens

<400> SEQUENCE: 23
atggcgtcgg aggggccgcg ggagcccgaa agcgagggca tcaagttatc agcagatgtc      60
aaaccatttg tccccagatt tgccgggctc aatgtggcat ggttagagtc ctcagaagca     120
tgtgtcttcc ccagctctgc agccacatac tatccgtttg ttcaggaacc accagtgaca     180
gagcagaaaa tatatactga agacatggcc tttggagctt caacttttcc acctcagtat     240
ttatcttctg agataactct tcatccatat gcctattctc cttatacccct tgactccaca     300 cagaatgttt actcagtgcc tggctcccag tatctttata accaacccag ttgttaccga     360

```
ggttttcaaa cagtgaagca tcgaaatgag aacacatgcc ctctcccaca agaaatgaaa        420
gctctgttta agaagaaaac ctatgatgag aaaaaaacgt atgatcagca aaagtttgac        480
agtgaaaggg ctgatggaac tatatcatct gagataaaat cagctagagg ttcacatcat        540
ttgtccattt acgctgagaa tagttttgaaa tcagatggtt accataagcg aacagacagg       600
aaatccagaa tcattgcaaa aaatgtatct acctccaaac ctgagtttga atttaccaca        660
ctggactttc ctgaactgca aggtgcagag aacaatatgt cagagataca gaagcaaccc        720
aagtggggac ctgtccactc tgtctctacc gacatttctc ttctaagaga agtagtaaaa        780
ccagctgcag tgttatcaaa gggtgaaata gtggtgaaaa ataacccaaa tgaatctgta        840
actgctaatg ccgctaccaa ttctccttca tgtacaagag agttatcttg acaccaatg         900 ggttatgttg ttcgacagac attatctaca gaactgtcag cagcccctaa aaatgttact        960
tctatgataa acttaaagac cattgcttca tcagcagatc ctaaaaatgt tagtatacca       1020
tcttctgaag ctttatcttc ggatccttcc tacaacaaag aaaaacacat tattcatcct       1080
acccaaaagt ctaaagcatc acaaggtagt gaccttgaac aaaatgaagc tcaagaaag        1140 aataagaaaa agaagaaaaa atctacatca aaatatgaag tcctgacagt tcaagagcct       1200
ccaaggattg aagatgccga ggaatttccc aacctggcag ttgcatctga aagaagagac       1260
agaatagaga caccgaaatt tcaatctaag cagcagccac aggataattt taaaaataat       1320
gtaaagaaga gccagcttcc agtgcagttg gacttggggg gcatgctgac agccctggag       1380
aagaagcagc actctcagca tgcaaagcag tcctccaaac cagtggtagt ctcagttgga       1440
gcagtgccag tcctttccaa agaatgtgca tcaggggaga gaggccgccg catgagtcaa       1500
atgaagaccc cgcacaatcc cttggactcc agcgccccac tgatgaagaa agggaagcag       1560
agggagatcc ccaaggccaa gaagccaacc tcactgaaga agattatttt gaaagaacgg       1620
caagagagaa agcagcgtct ccaagaaaat gctgtgagtc cagcttttac cagtgatgac       1680
acacaagatg gagagagtgg tggtgatgac cagtttcccg agcaggcaga gctgtcaggg       1740
ccagagggga tggacgaact gatctccact ccttcggttg aggacaagtc tgaagagcca       1800
ccaggcacag agctccagag ggacacagag gcctcccacc ttgctcccaa tcacaccacc       1860
ttccctaaga tccacagccg cagattcagg gattactgca gccagatgct tagtaaagaa       1920
gtggatgctt gtgttaccga cctactcaaa gaactggtcc gtttccaaga ccgtatgtac       1980
cagaaagatc cagtcaaggc caagactaaa cgtcgacttg tgttggggtt gagggaggtt       2040
ctcaaacacc tgaagctcaa aaaactgaaa tgtgtcatta tttctcccaa ctgtgagaag       2100
atacagtcaa aggtgggct ggatgacact ttgcacacaa ttattgatta tgcctgtgag       2160
cagaacattc cctttgtgtt tgctctcaac cgcaaagctc tggggcgcag tttgaataag       2220
gcagttcctg tcagtgtggt ggggatcttc agctatgatg gggcccagga tcagttccac       2280
aagatggttg agctgacagt ggcggcccga caggcgtaca agaccatgct ggagaatgtg       2340
cagcaggagc tggtgggaga gcccaggcct caggcacctc ccagcctacc cacacagggc       2400
cccagctgcc ctgcagaaga tggccccca gccctgaaag aaaaagaaga gccacactac       2460
attgaaatct ggaaaaaaca tctggaagca tacagtggat gtaccctgga gctagaagaa       2520
tccttggagg cttcaacctc tcaaatgatg aatttgaatt tatga                       2565
```

<210> SEQ ID NO 24
<211> LENGTH: 854
<212> TYPE: PRT
<213> ORGANISM: Homo sapiens

<400> SEQUENCE: 24

```
Met Ala Ser Glu Gly Pro Arg Glu Pro Glu Ser Glu Gly Ile Lys Leu
1               5                   10                  15

Ser Ala Asp Val Lys Pro Phe Val Pro Arg Phe Ala Gly Leu Asn Val
                20                  25                  30

Ala Trp Leu Glu Ser Ser Glu Ala Cys Val Phe Pro Ser Ser Ala Ala
            35                  40                  45

Thr Tyr Tyr Pro Phe Val Gln Glu Pro Pro Val Thr Glu Gln Lys Ile
    50                  55                  60

Tyr Thr Glu Asp Met Ala Phe Gly Ala Ser Thr Phe Pro Pro Gln Tyr
65                  70                  75                  80

Leu Ser Ser Glu Ile Thr Leu His Pro Tyr Ala Tyr Ser Pro Tyr Thr
                85                  90                  95

Leu Asp Ser Thr Gln Asn Val Tyr Ser Val Pro Gly Ser Gln Tyr Leu
                100                 105                 110

Tyr Asn Gln Pro Ser Cys Tyr Arg Gly Phe Gln Thr Val Lys His Arg
                115                 120                 125

Asn Glu Asn Thr Cys Pro Leu Pro Gln Glu Met Lys Ala Leu Phe Lys
130                 135                 140

Lys Lys Thr Tyr Asp Glu Lys Lys Thr Tyr Asp Gln Gln Lys Phe Asp
145                 150                 155                 160

Ser Glu Arg Ala Asp Gly Thr Ile Ser Ser Glu Ile Lys Ser Ala Arg
                165                 170                 175

Gly Ser His His Leu Ser Ile Tyr Ala Glu Asn Ser Leu Lys Ser Asp
                180                 185                 190

Gly Tyr His Lys Arg Thr Asp Arg Lys Ser Arg Ile Ile Ala Lys Asn
                195                 200                 205

Val Ser Thr Ser Lys Pro Glu Phe Glu Phe Thr Thr Leu Asp Phe Pro
210                 215                 220

Glu Leu Gln Gly Ala Glu Asn Asn Met Ser Glu Ile Gly Lys Gln Pro
225                 230                 235                 240

Lys Trp Gly Pro Val His Ser Val Ser Thr Asp Ile Ser Leu Leu Arg
                245                 250                 255

Glu Val Val Lys Pro Ala Ala Val Leu Ser Lys Gly Glu Ile Val Val
                260                 265                 270

Lys Asn Asn Pro Asn Glu Ser Val Thr Ala Asn Ala Ala Thr Asn Ser
                275                 280                 285

Pro Ser Cys Thr Arg Glu Leu Ser Trp Thr Pro Met Gly Tyr Val Val
                290                 295                 300

Arg Gln Thr Leu Ser Thr Glu Leu Ser Ala Ala Pro Lys Asn Val Thr
305                 310                 315                 320

Ser Met Ile Asn Leu Lys Thr Ile Ala Ser Ala Asp Pro Lys Asn
                325                 330                 335

Val Ser Ile Pro Ser Ser Glu Ala Leu Ser Ser Asp Pro Ser Tyr Asn
                340                 345                 350

Lys Glu Lys His Ile Ile His Pro Thr Gln Lys Ser Lys Ala Ser Gln
                355                 360                 365

Gly Ser Asp Leu Glu Gln Asn Glu Ala Ser Arg Lys Asn Lys Lys Lys
                370                 375                 380

Lys Glu Lys Ser Thr Ser Lys Tyr Glu Val Leu Thr Val Gln Glu Pro
385                 390                 395                 400

Pro Arg Ile Glu Asp Ala Glu Glu Phe Pro Asn Leu Ala Val Ala Ser
                405                 410                 415
```

-continued

```
Glu Arg Arg Asp Arg Ile Glu Thr Pro Lys Phe Gln Ser Lys Gln Gln
            420                 425                 430

Pro Gln Asp Asn Phe Lys Asn Val Lys Lys Ser Gln Leu Pro Val
            435                 440                 445

Gln Leu Asp Leu Gly Gly Met Leu Thr Ala Leu Glu Lys Lys Gln His
        450                 455                 460

Ser Gln His Ala Lys Gln Ser Ser Lys Pro Val Val Ser Val Gly
465                 470                 475                 480

Ala Val Pro Val Leu Ser Lys Glu Cys Ala Ser Gly Glu Arg Gly Arg
                485                 490                 495

Arg Met Ser Gln Met Lys Thr Pro His Asn Pro Leu Asp Ser Ser Ala
            500                 505                 510

Pro Leu Met Lys Lys Gly Lys Gln Arg Glu Ile Pro Lys Ala Lys Lys
            515                 520                 525

Pro Thr Ser Leu Lys Lys Ile Ile Leu Lys Glu Arg Gln Glu Arg Lys
        530                 535                 540

Gln Arg Leu Gln Glu Asn Ala Val Ser Pro Ala Phe Thr Ser Asp Asp
545                 550                 555                 560

Thr Gln Asp Gly Glu Ser Gly Gly Asp Asp Gln Phe Pro Glu Gln Ala
                565                 570                 575

Glu Leu Ser Gly Pro Glu Gly Met Asp Glu Leu Ile Ser Thr Pro Ser
            580                 585                 590

Val Glu Asp Lys Ser Glu Glu Pro Pro Gly Thr Glu Leu Gln Arg Asp
            595                 600                 605

Thr Glu Ala Ser His Leu Ala Pro Asn His Thr Thr Phe Pro Lys Ile
        610                 615                 620

His Ser Arg Arg Phe Arg Asp Tyr Cys Ser Gln Met Leu Ser Lys Glu
625                 630                 635                 640

Val Asp Ala Cys Val Thr Asp Leu Leu Lys Glu Leu Val Arg Phe Gln
                645                 650                 655

Asp Arg Met Tyr Gln Lys Asp Pro Val Lys Ala Lys Thr Lys Arg Arg
            660                 665                 670

Leu Val Leu Gly Leu Arg Glu Val Leu Lys His Leu Lys Leu Lys Lys
        675                 680                 685

Leu Lys Cys Val Ile Ile Ser Pro Asn Cys Glu Lys Ile Gln Ser Lys
690                 695                 700

Gly Gly Leu Asp Asp Thr Leu His Thr Ile Ile Asp Tyr Ala Cys Glu
705                 710                 715                 720

Gln Asn Ile Pro Phe Val Phe Ala Leu Asn Arg Lys Ala Leu Gly Arg
                725                 730                 735

Ser Leu Asn Lys Ala Val Pro Val Ser Val Val Gly Ile Phe Ser Tyr
            740                 745                 750

Asp Gly Ala Gln Asp Gln Phe His Lys Met Val Glu Leu Thr Val Ala
        755                 760                 765

Ala Arg Gln Ala Tyr Lys Thr Met Leu Glu Asn Val Gln Gln Glu Leu
        770                 775                 780

Val Gly Glu Pro Arg Pro Gln Ala Pro Ser Leu Pro Thr Gln Gly
785                 790                 795                 800

Pro Ser Cys Pro Ala Glu Asp Gly Pro Pro Ala Leu Lys Glu Lys Glu
                805                 810                 815

Glu Pro His Tyr Ile Glu Ile Trp Lys Lys His Leu Glu Ala Tyr Ser
            820                 825                 830

Gly Cys Thr Leu Glu Leu Glu Glu Ser Leu Glu Ala Ser Thr Ser Gln
        835                 840                 845
```

Met Met Asn Leu Asn Leu
    850

<210> SEQ ID NO 25
<211> LENGTH: 2907
<212> TYPE: DNA
<213> ORGANISM: Monodelphis domestica

<400> SEQUENCE: 25

| | | | | | |
|---|---|---|---|---|---|
| atgccccctc | aaagggagcc | cctcacctcg | tggtctgctc | tagagagcca | agtcattttt | 60 |
| gagtcctacc | ttgttcacac | ttggacacaa | ctttccggtg | gtctgagcgc | ccgttctgag | 120 |
| tgcgagtact | tggatttctg | gatttcgcca | agtagcccac | gtgcgccccg | ccctggcgaa | 180 |
| gggcgcaagc | gtgccgagaa | cgctcctgcg | tcgcggcgtc | tgtcgcactt | ctgtgacgca | 240 |
| cttcctcgc | gtcggtggga | aaagaggaag | cagaggagga | gaaggagga | gggtaggttc | 300 |
| ctttgctcct | ctgagggaag | ccccgaggag | tggcctccta | cccacccccc | ctcctccacc | 360 |
| atgacctcgg | aggggaaaag | ggagcccgat | aacgagggca | gcatcaagtt | atcagcagat | 420 |
| gtcaaaccgt | ttgtcccaaa | atatgctgcg | cttaatgtgg | catggtcaga | gtcctcagac | 480 |
| gcttgtgtct | tccctaacta | cgcaactaca | tgctatccat | ttgttcagga | actacctgtg | 540 |
| actgaacaga | agccttatgc | cgaagatgtc | tctcttggat | cttcttcacc | tttttcatct | 600 |
| caatattcat | ctcctgattt | tgctgttgat | catcactgca | cttcttctca | ctcatctgtg | 660 |
| tctgcacaaa | ctatttgttc | agtacctggc | tcacagtatg | attatagtca | ccctaaaatat | 720 |
| tatagtaatg | tgccagtagt | taagtccaga | aatgaacaaa | tttgttctct | cccacaagaa | 780 |
| actaaaagcc | tatataagaa | agaacatgt | gatgagcaaa | aattaaataa | taaaggacct | 840 |
| gaagggaatt | catcctctaa | tataaaacca | gctaaaggtt | cccatcagaa | ttctacccac | 900 |
| cctgaaggtg | gttcaaaatc | agaggcttct | cataaacgtg | cagacaggaa | acctaaaggc | 960 |
| agccggaaaa | atgagccttc | ttccaaaccc | gaatttgaac | tgaagctgtt | ggatttccct | 1020 |
| aaactgcaag | gttctgagaa | cagtgatgtg | ccagaattgc | aaaagcagcc | caaatgggga | 1080 |
| cctttgagct | ccgctgttaa | tgagatatcc | cttatgagag | aagtagcgaa | gcctacgcta | 1140 |
| acattatcca | aggaagcctt | agttgtgaaa | gccgaaacct | ctgagcccga | aatgacact | 1200 |
| aatccccct | cttctacaag | agagctatct | tggacaccaa | tgggctatgt | tgttcggcca | 1260 |
| acaaccactg | aagcagcagc | ccttaaaaat | gtcgcttcac | tgtcaaacac | aaagaaaaat | 1320 |
| tcatcagtaa | ctcctaagaa | aattactaca | tcattctcct | cacctgaggt | tctagcaacc | 1380 |
| aatgcttaca | caaggacaa | acaaatagct | cagaatccga | aaaagacaaa | aaccagcaac | 1440 |
| atgtgcgaaa | gtgaccagga | agaaatgaaa | agaacaaga | aaaagaaaag | gaagcctaaa | 1500 |
| acaaattttg | aaactcttat | ggtccaggag | ccacccaaga | ttgaagatat | tgaagagttt | 1560 |
| cctaatctgg | aagttgcttc | tgaaagaaaa | aacagactgg | accettcaaa | atatttatct | 1620 |
| aaatatcaac | cagagactac | ttccaaaaag | tttgggaaga | gagtcaaat | tccagtgaag | 1680 |
| ttggatttgg | gaggaatgct | tgctgcattg | gaaaaaaagc | agcattcaca | gaattcaaaa | 1740 |
| cagtcttcca | acctgttgt | tgtttctgtt | ggtgcagtac | cagtactttc | caagaattg | 1800 |
| gcaacatcag | tgaaaaatca | ccggttaaat | caagtgatgt | ctcctcataa | tcctttggat | 1860 |
| tctagttctc | cattaataaa | gaaggcaag | caagggaag | tcccaaaggc | caagaagcca | 1920 |
| acatctctga | agaagattat | tttgaaagaa | cgagaagaaa | gaaagcagaa | acatctctta | 1980 |
| gaacagcttt | cagtgccagc | atttctaaa | agcatggagc | aagatttggc | gaataatgtt | 2040 |

-continued

```
gataatcagt cacctgccca gattgcccag ccagaggaaa cagaagaatc agtccctgcc    2100
tcttctactg ttgacgtgga aaacacgcca gaaaacccc tagacagcct tgtaccccaa     2160
aaggatggag aagtgtgtcc cattgttaca cagccaacgg cacctttcc caagatccat     2220 agtaggagat ttagagatta ctgtagccaa atgcttagta aagaagttga tgactgtgtg    2280
atggatcttc taaaagaact ggttcgcttt caagatcgta tgtatcagaa ggatccagta    2340
aaggccaaaa ccaaacgccg gcttgtgatg ggactcagag aagtgcttaa acatctgaag    2400
ctaaaaaaac taaatgtgt cattatttct ccaaactgtg agaagagcaa atcgaaaggt     2460
gggctggacg agacgctgca caccatcatc gactatgcct gcgagcagaa cgtcccctt    2520 gtgtttgccc tcaaccggaa ggctctgggg cgaagcgtca acaaagtcgt cccagtcagt    2580
gtggtgggga tcttcagcta tgacggcgct caggaccaat ttcacaagat gatagccctg    2640
acaatggaag ccagacaggc atataagatt atgttatcaa ctttaaagga ggagcctgaa    2700
gcactggaga cggagaatcc tccatccccc tcgctccctc gtccaagcga gagctgccct    2760
tcagaacttg gtcaaacgag cgaccccaca caggaagagg aaccgaacta cattaaaata    2820
tggaagaaaa atcttgaaga gtataatccg tatgcactgg aactagagca ggcctccacc    2880
actgaaatgc tgaacttgaa tttgtga                                        2907
```

<210> SEQ ID NO 26
<211> LENGTH: 968
<212> TYPE: PRT
<213> ORGANISM: Monodelphis domestica

<400> SEQUENCE: 26

```
Met Pro Pro Gln Arg Glu Pro Leu Thr Ser Trp Ser Ala Leu Glu Ser
1               5                   10                  15

Gln Val Ile Phe Glu Ser Tyr Leu Val His Thr Trp Thr Gln Leu Ser
            20                  25                  30

Gly Gly Leu Ser Ala Arg Ser Glu Cys Glu Tyr Leu Asp Phe Trp Ile
        35                  40                  45

Ser Pro Ser Ser Pro Arg Ala Pro Arg Pro Gly Glu Gly Arg Lys Arg
    50                  55                  60

Ala Glu Asn Ala Pro Ala Ser Arg Arg Leu Ser His Phe Cys Asp Ala
65                  70                  75                  80

Leu Ser Ser Arg Arg Trp Glu Lys Arg Lys Gln Arg Arg Lys Glu
            85                  90                  95

Glu Gly Arg Phe Leu Cys Ser Ser Glu Gly Ser Pro Glu Glu Trp Pro
        100                 105                 110

Pro Thr His Pro Pro Ser Ser Thr Met Thr Ser Glu Gly Lys Arg Glu
    115                 120                 125

Pro Asp Asn Glu Gly Ser Ile Lys Leu Ser Ala Asp Val Lys Pro Phe
130                 135                 140

Val Pro Lys Tyr Ala Ala Leu Asn Val Ala Trp Ser Glu Ser Ser Asp
145                 150                 155                 160

Ala Cys Val Phe Pro Asn Tyr Ala Thr Thr Cys Tyr Pro Phe Val Gln
            165                 170                 175

Glu Leu Pro Val Thr Glu Gln Lys Pro Tyr Ala Glu Asp Val Ser Leu
        180                 185                 190

Gly Ser Ser Ser Pro Phe Ser Ser Gln Tyr Ser Ser Pro Asp Phe Ala
    195                 200                 205

Val Asp His His Cys Thr Ser Ser His Ser Ser Val Ser Ala Gln Thr
210                 215                 220
```

```
Ile Cys Ser Val Pro Gly Ser Gln Tyr Asp Tyr Ser His Pro Lys Tyr
225                 230                 235                 240

Tyr Ser Asn Val Pro Val Val Lys Ser Arg Asn Glu Gln Ile Cys Ser
            245                 250                 255

Leu Pro Gln Glu Thr Lys Ser Leu Tyr Lys Lys Arg Thr Cys Asp Glu
                260                 265                 270

Gln Lys Leu Asn Asn Lys Gly Pro Glu Gly Asn Ser Ser Asn Ile
        275                 280                 285

Lys Pro Ala Lys Gly Ser His Gln Asn Ser Thr His Pro Glu Gly Gly
290                 295                 300

Ser Lys Ser Glu Ala Ser His Lys Arg Ala Asp Arg Lys Pro Lys Gly
305                 310                 315                 320

Ser Arg Lys Asn Glu Pro Ser Ser Lys Pro Glu Phe Glu Leu Lys Leu
                325                 330                 335

Leu Asp Phe Pro Lys Leu Gln Gly Ser Glu Asn Ser Asp Val Pro Glu
                340                 345                 350

Leu Gln Lys Gln Pro Lys Trp Gly Pro Leu Ser Ser Ala Val Asn Glu
        355                 360                 365

Ile Ser Leu Met Arg Glu Val Ala Lys Pro Thr Leu Thr Leu Ser Lys
370                 375                 380

Glu Ala Leu Val Val Lys Ala Glu Thr Ser Glu Pro Glu Asn Asp Thr
385                 390                 395                 400

Asn Pro Pro Ser Ser Thr Arg Glu Leu Ser Trp Thr Pro Met Gly Tyr
                405                 410                 415

Val Val Arg Pro Thr Thr Thr Glu Ala Ala Leu Lys Asn Val Ala
                420                 425                 430

Ser Leu Ser Asn Thr Lys Lys Asn Ser Ser Val Thr Pro Lys Lys Ile
        435                 440                 445

Thr Thr Ser Phe Ser Ser Pro Glu Val Leu Ala Thr Asn Ala Tyr Asn
    450                 455                 460

Lys Asp Lys Gln Ile Ala Gln Asn Pro Lys Lys Thr Lys Thr Ser Asn
465                 470                 475                 480

Met Cys Glu Ser Asp Gln Glu Met Lys Lys Asn Lys Lys Lys
                485                 490                 495

Arg Lys Pro Lys Thr Asn Phe Glu Thr Leu Met Val Gln Glu Pro Pro
                500                 505                 510

Lys Ile Glu Asp Ile Glu Glu Phe Pro Asn Leu Glu Val Ala Ser Glu
        515                 520                 525

Arg Lys Asn Arg Leu Asp Pro Ser Lys Tyr Leu Ser Lys Tyr Gln Pro
        530                 535                 540

Glu Thr Thr Ser Lys Lys Phe Gly Lys Lys Ser Gln Ile Pro Val Lys
545                 550                 555                 560

Leu Asp Leu Gly Gly Met Leu Ala Ala Leu Glu Lys Lys Gln His Ser
                565                 570                 575

Gln Asn Ser Lys Gln Ser Ser Lys Pro Val Val Val Ser Val Gly Ala
        580                 585                 590

Val Pro Val Leu Ser Lys Glu Leu Ala Thr Ser Val Lys Asn His Arg
    595                 600                 605

Leu Asn Gln Val Met Ser Pro His Asn Pro Leu Asp Ser Ser Ser Pro
610                 615                 620

Leu Ile Lys Lys Gly Lys Gln Arg Glu Val Pro Lys Ala Lys Lys Pro
625                 630                 635                 640

Thr Ser Leu Lys Lys Ile Ile Leu Lys Glu Arg Glu Glu Arg Lys Gln
                645                 650                 655
```

```
Lys His Leu Leu Glu Gln Leu Ser Val Pro Ala Phe Ser Lys Ser Met
            660                 665                 670
Glu Gln Asp Leu Ala Asn Asn Val Asp Asn Gln Ser Pro Ala Gln Ile
        675                 680                 685
Ala Gln Pro Glu Glu Thr Glu Ser Val Pro Ala Ser Ser Thr Val
    690                 695                 700
Asp Val Glu Asn Thr Pro Glu Lys Pro Leu Asp Ser Leu Val Pro Gln
705                 710                 715                 720
Lys Asp Gly Glu Val Cys Pro Ile Val Thr Gln Pro Thr Ala Pro Phe
                725                 730                 735
Pro Lys Ile His Ser Arg Arg Phe Arg Asp Tyr Cys Ser Gln Met Leu
            740                 745                 750
Ser Lys Glu Val Asp Asp Cys Val Met Asp Leu Leu Lys Glu Leu Val
        755                 760                 765
Arg Phe Gln Asp Arg Met Tyr Gln Lys Asp Pro Val Lys Ala Lys Thr
    770                 775                 780
Lys Arg Arg Leu Val Met Gly Leu Arg Glu Val Leu Lys His Leu Lys
785                 790                 795                 800
Leu Lys Lys Leu Lys Cys Val Ile Ile Ser Pro Asn Cys Glu Lys Ser
                805                 810                 815
Lys Ser Lys Gly Gly Leu Asp Glu Thr Leu His Thr Ile Ile Asp Tyr
            820                 825                 830
Ala Cys Glu Gln Asn Val Pro Phe Val Phe Ala Leu Asn Arg Lys Ala
        835                 840                 845
Leu Gly Arg Ser Val Asn Lys Val Val Pro Val Ser Val Val Gly Ile
    850                 855                 860
Phe Ser Tyr Asp Gly Ala Gln Asp Gln Phe His Lys Met Ile Ala Leu
865                 870                 875                 880
Thr Met Glu Ala Arg Gln Ala Tyr Lys Ile Met Leu Ser Thr Leu Lys
                885                 890                 895
Glu Glu Pro Glu Ala Leu Glu Thr Asn Pro Ser Pro Ser Leu
            900                 905                 910
Pro Arg Pro Ser Glu Ser Cys Pro Ser Glu Leu Gly Gln Thr Ser Asp
        915                 920                 925
Pro Thr Gln Glu Glu Pro Asn Tyr Ile Lys Ile Trp Lys Lys Asn
    930                 935                 940
Leu Glu Glu Tyr Asn Pro Tyr Ala Leu Glu Leu Glu Gln Ala Ser Thr
945                 950                 955                 960
Thr Glu Met Leu Asn Leu Asn Leu
                965

<210> SEQ ID NO 27
<211> LENGTH: 2553
<212> TYPE: DNA
<213> ORGANISM: Canis lupus

<400> SEQUENCE: 27
atggcgtcgg agggccgcg ggggccggtc ggcgagggca tcaagttgtc agcagatgtc     60
aagccgtttg tccccaaatt tgcagggctc agtgtggcct gggcagagtc ttcggaagca    120
cgtgtgttcc ccggctgtgc agccacctac tacccgtgtg ttcaggagct gccggtgcct    180
gagcagaagc tctacactga agatatggcc tttggggctt caacgtttcc acctcagtat    240
ttatcttctg agctcgctct tcatccatgc agttactctc cttactctat ggagtgtgca    300
cagagtgtct gcccagtgcc tgggtcccag tatgcttaca gccaccccag cggttaccga    360
```

```
ggttttcaga ccatgaagcc acgaaacgag cagatgtgcc ctctcccaca agacacaaaa    420
gctctgttta agaaaaaaac atacgagcaa aagtttgaca gcaagaaggc cgacggatct    480
ctgtcatcgg atctaaaatc agttagaggt tcacatccta tgtccattcc cgctgacagt    540
aatttgaaat cagatggtta tcataaacga acagacagga aatccagaat tgttgaaaaa    600
agtggatctg cctccaaacc tgagtttgaa tttaccaggt tggattttcc tgagctgcca    660
ggcccagaga acagcaagct ctcagagaca cagaagccac ccaagtgggg gcctctacgc    720
tccgcctcag ctgacctttc tcttctcagg gaggtggtga acccactgt ggtgacagca     780
gagggtgaag gggtggtgag aagcacagat gcagtggagt ctatgactgg cagctctgtg    840
gccgatccct cctcatgtac cagagagtta tcttggacac caatgggtta tgttgttcgg    900
cagacattat ctacagaacg gtcagcagcc cctaaaaacg ttacctccat gataaaccta    960
aagatggttg cttcatcagc agaccctaaa agtgttagta tatcacctcc tgaagtttta   1020
tcttcggatc tttcctacaa agagagacat gtccacccag ctaaaaagtc caagcgtca    1080
cagggtggcg atcccgaaca gaatgaagcc tcaagaaagc ataagaaaaa gaaagaaaag   1140
tctaaatcaa aatatgaagt cttgacagtt caggagccac caaggattga agatgccgag   1200
gagttcccca atctggcagt tgcgtctgaa agaagagaca gagtagcatc tccgaaattt   1260
caatccaaac agcagccaca gaataatttt aaaaatagtg gaaagaagag ccaacttccg   1320
gtacagttgg atttagggggg aatgctagca gccctggaaa agaagcagca ctcccagagc   1380
tcgaagccgt cctccaaacc tgtggtgttc tcagttgggg cggtgccggt tctctccagg   1440
gacactgcgt cggggaagaa gggccaccac ttcagccagg tgaagacccc acacaacccc   1500
ttggactcca gcgcccccgct gatgaagaag gggaagcaga gggaggtccc caaggccaag   1560
aagccaacct ccttgaagaa gatcattttg aaagaacggc aggagagaaa gcagcagcgt   1620
ctccaagaaa atgctgtgag cccagctcct gccagtgacg ctgtgccgga cggggagagc   1680
ggcggtgacg atgaggcctt cgagcaggtt gaccccctcag ttgcagaggg gccggaggag   1740
gtgctgtcct ctgctcccgc agtggagagc gggtcagaag agccgccgag agctgagctc   1800
cagaaggagg cggagggctg ccacctggtg cccaatggcg ccagctgccc caagatccac   1860
agccggagat tcagggacta ctgcagccag atgctgagca aggaggtgga tgcctgtgtc   1920
acggatctgc tgaaggagct ggtgcgattc caagaccgca tgtaccagaa ggatccagtc   1980
aaggctaaga ccaaacgccg actcgtgctg gggctgcggg aggtcctcaa gcatctgaaa   2040
ctcaggaagc tcaaatgcat catcatctct cccaactgtg agaagatcca gtcgaaaggt   2100
gggctggatg acacgctgca caccatcatt gattacgcct gtgagcagaa cattcccttt   2160
gtgtttgcac tcaaccgcaa ggctctgggg cgcagtttga acaaggctgt ccctgtcagt   2220
gtggtgggca tcttcagcta cgatgggggcc caggaccagt tccacaggat ggtcgagctg   2280
acgatggctg cgcggcaggc ctacaagacc atgttggaga atgtgcgcca ggagttggct   2340
ggggagcctg ggaccccagc tctggccaac ccgcccatgc agggtcttgg ctgctccacg   2400
caggacagcc cccctgctcc tacagccgag aaagaagagc cccattacat tgaaatctgg   2460
aggagacacc tggaagcgta cagtcgctgt gccctggagc tggaagactc actggaggct   2520
tcaacctctc agatgatgaa cctgaactta tag                                2553
```

<210> SEQ ID NO 28
<211> LENGTH: 850
<212> TYPE: PRT
<213> ORGANISM: Canis lupus

<400> SEQUENCE: 28

```
Met Ala Ser Glu Gly Pro Arg Gly Pro Val Gly Glu Gly Ile Lys Leu
1               5                   10                  15

Ser Ala Asp Val Lys Pro Phe Val Pro Lys Phe Ala Gly Leu Ser Val
            20                  25                  30

Ala Trp Ala Glu Ser Ser Glu Ala Arg Val Phe Pro Gly Cys Ala Ala
        35                  40                  45

Thr Tyr Tyr Pro Cys Val Gln Glu Leu Pro Val Pro Glu Gln Lys Leu
    50                  55                  60

Tyr Thr Glu Asp Met Ala Phe Gly Ala Ser Thr Phe Pro Pro Gln Tyr
65                  70                  75                  80

Leu Ser Ser Glu Leu Ala Leu His Pro Cys Ser Tyr Ser Pro Tyr Ser
                85                  90                  95

Met Glu Cys Ala Gln Ser Val Cys Pro Val Pro Gly Ser Gln Tyr Ala
                100                 105                 110

Tyr Ser His Pro Ser Gly Tyr Arg Gly Phe Gln Thr Met Lys Pro Arg
            115                 120                 125

Asn Glu Gln Met Cys Pro Leu Pro Gln Asp Thr Lys Ala Leu Phe Lys
130                 135                 140

Lys Lys Thr Tyr Glu Gln Lys Phe Asp Ser Lys Lys Ala Asp Gly Ser
145                 150                 155                 160

Leu Ser Ser Asp Leu Lys Ser Val Arg Gly Ser His Pro Met Ser Ile
                165                 170                 175

Pro Ala Asp Ser Asn Leu Lys Ser Asp Gly Tyr His Lys Arg Thr Asp
            180                 185                 190

Arg Lys Ser Arg Ile Val Glu Lys Ser Gly Ser Ala Ser Lys Pro Glu
        195                 200                 205

Phe Glu Phe Thr Arg Leu Asp Phe Pro Glu Leu Pro Gly Pro Glu Asn
    210                 215                 220

Ser Lys Leu Ser Glu Thr Gln Lys Pro Pro Lys Trp Gly Pro Leu Arg
225                 230                 235                 240

Ser Ala Ser Ala Asp Leu Ser Leu Leu Arg Glu Val Val Lys Pro Thr
                245                 250                 255

Val Val Thr Ala Glu Gly Glu Gly Val Val Arg Ser Thr Asp Ala Val
                260                 265                 270

Glu Ser Met Thr Gly Ser Ser Val Ala Asp Pro Ser Ser Cys Thr Arg
            275                 280                 285

Glu Leu Ser Trp Thr Pro Met Gly Tyr Val Val Arg Gln Thr Leu Ser
    290                 295                 300

Thr Glu Arg Ser Ala Ala Pro Lys Asn Val Thr Ser Met Ile Asn Leu
305                 310                 315                 320

Lys Met Val Ala Ser Ala Asp Pro Lys Ser Val Ser Ile Ser Pro
                325                 330                 335

Pro Glu Val Leu Ser Ser Asp Leu Ser Tyr Lys Glu Arg His Val His
            340                 345                 350

Pro Ala Lys Lys Ser Lys Ala Ser Gln Gly Gly Asp Pro Glu Gln Asn
            355                 360                 365

Glu Ala Ser Arg Lys His Lys Lys Lys Glu Lys Ser Lys Ser Lys
370                 375                 380

Tyr Glu Val Leu Thr Val Gln Glu Pro Pro Arg Ile Glu Asp Ala Glu
385                 390                 395                 400

Glu Phe Pro Asn Leu Ala Val Ala Ser Glu Arg Arg Asp Arg Val Ala
                405                 410                 415
```

```
Ser Pro Lys Phe Gln Ser Lys Gln Pro Gln Asn Asn Phe Lys Asn
            420                 425                 430

Ser Gly Lys Lys Ser Gln Leu Pro Val Gln Leu Asp Leu Gly Gly Met
        435                 440                 445

Leu Ala Leu Glu Lys Lys Gln His Ser Gln Ser Ser Lys Pro Ser
    450                 455                 460

Ser Lys Pro Val Val Phe Ser Val Gly Ala Val Pro Val Leu Ser Arg
465                 470                 475                 480

Asp Thr Ala Ser Gly Lys Lys Gly His His Phe Ser Gln Val Lys Thr
                485                 490                 495

Pro His Asn Pro Leu Asp Ser Ser Ala Pro Leu Met Lys Lys Gly Lys
            500                 505                 510

Gln Arg Glu Val Pro Lys Ala Lys Lys Pro Thr Ser Leu Lys Lys Ile
        515                 520                 525

Ile Leu Lys Glu Arg Gln Glu Arg Lys Gln Arg Leu Gln Glu Asn
    530                 535                 540

Ala Val Ser Pro Ala Pro Ala Ser Asp Ala Val Pro Asp Gly Glu Ser
545                 550                 555                 560

Gly Gly Asp Asp Glu Ala Phe Glu Gln Val Asp Pro Ser Val Ala Glu
                565                 570                 575

Gly Pro Glu Glu Val Leu Ser Ser Ala Pro Ala Val Glu Ser Gly Ser
            580                 585                 590

Glu Glu Pro Pro Arg Ala Glu Leu Gln Lys Glu Ala Glu Gly Cys His
        595                 600                 605

Leu Val Pro Asn Gly Ala Ser Cys Pro Lys Ile His Ser Arg Arg Phe
    610                 615                 620

Arg Asp Tyr Cys Ser Gln Met Leu Ser Lys Glu Val Asp Ala Cys Val
625                 630                 635                 640

Thr Asp Leu Leu Lys Glu Leu Val Arg Phe Gln Asp Arg Met Tyr Gln
                645                 650                 655

Lys Asp Pro Val Lys Ala Lys Thr Lys Arg Arg Leu Val Leu Gly Leu
            660                 665                 670

Arg Glu Val Leu Lys His Leu Lys Leu Arg Lys Leu Lys Cys Ile Ile
        675                 680                 685

Ile Ser Pro Asn Cys Glu Lys Ile Gln Ser Lys Gly Gly Leu Asp Asp
    690                 695                 700

Thr Leu His Thr Ile Ile Asp Tyr Ala Cys Glu Gln Asn Ile Pro Phe
705                 710                 715                 720

Val Phe Ala Leu Asn Arg Lys Ala Leu Gly Arg Ser Leu Asn Lys Ala
                725                 730                 735

Val Pro Val Ser Val Val Gly Ile Phe Ser Tyr Asp Gly Ala Gln Asp
            740                 745                 750

Gln Phe His Arg Met Val Glu Leu Thr Met Ala Ala Arg Gln Ala Tyr
        755                 760                 765

Lys Thr Met Leu Glu Asn Val Arg Gln Glu Leu Ala Gly Glu Pro Gly
    770                 775                 780

Thr Pro Ala Leu Ala Asn Pro Pro Met Gln Gly Leu Gly Cys Ser Thr
785                 790                 795                 800

Gln Asp Ser Pro Pro Ala Pro Thr Ala Glu Lys Glu Glu Pro His Tyr
                805                 810                 815

Ile Glu Ile Trp Arg Arg His Leu Glu Ala Tyr Ser Arg Cys Ala Leu
            820                 825                 830

Glu Leu Glu Asp Ser Leu Glu Ala Ser Thr Ser Gln Met Met Asn Leu
```

-continued

```
            835                 840                 845

Asn Leu
    850

<210> SEQ ID NO 29
<211> LENGTH: 134
<212> TYPE: PRT
<213> ORGANISM: Toxoplasma gondii
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: MISC_FEATURE
<222> LOCATION: (133)..(133)
<223> OTHER INFORMATION: Xaa is Selenocysteine residue

<400> SEQUENCE: 29

Met Glu Asn Glu Pro Ser Ala Ala Pro Asn Pro Trp Ala Ser Pro
1               5                   10                  15

Gly Pro Val Asn Ser Ser Arg Gly Arg Ala Arg Val Ile Asn Gly
            20                  25                  30

Gln Ile Val Tyr Gly Asp Glu Ala Gly Arg Pro Gly Ser Gln Ser Asp
        35                  40                  45

Ala Arg Ser Ser Arg Gln Ala Val Arg Pro Gly Leu Phe Val Arg Leu
    50                  55                  60

Cys Ala Phe Leu Phe Ala Leu Val Asp Phe Ile Arg Leu Phe Phe Gln
65                  70                  75                  80

Thr Ile Phe Ser Pro Asn Tyr Pro Asn Gln Gly Arg Arg Asn Arg Gln
                85                  90                  95

Met Gly Gly Val Ala Ser Leu Thr Pro Gly Gly Arg Pro Asp Gly
            100                 105                 110

Gly Gly Gly Ser Gly Ser Arg Pro Arg Tyr Gln Gln Xaa Phe Val Cys
        115                 120                 125

Gly Gly Gly Gly Xaa Gly
    130

<210> SEQ ID NO 30
<211> LENGTH: 94
<212> TYPE: PRT
<213> ORGANISM: Homo sapiens
<220> FEATURE:
<221> NAME/KEY: MISC_FEATURE
<222> LOCATION: (92)..(92)
<223> OTHER INFORMATION: Xaa is Selenocysteine residue

<400> SEQUENCE: 30

Met Val Tyr Ile Ser Asn Gly Gln Val Leu Asp Ser Arg Ser Gln Ser
1               5                   10                  15

Pro Trp Arg Leu Ser Leu Ile Thr Asp Phe Phe Trp Gly Ile Ala Glu
            20                  25                  30

Phe Val Val Leu Phe Phe Lys Thr Leu Leu Gln Gln Asp Val Lys Lys
        35                  40                  45

Arg Arg Ser Tyr Gly Asn Ser Ser Asp Ser Arg Tyr Asp Asp Gly Arg
    50                  55                  60

Gly Pro Pro Gly Asn Pro Pro Arg Arg Met Gly Arg Ile Asn His Leu
65                  70                  75                  80

Arg Gly Pro Ser Pro Pro Pro Met Ala Gly Gly Xaa Gly Arg
                85                  90

<210> SEQ ID NO 31
```

```
<211> LENGTH: 94
<212> TYPE: PRT
<213> ORGANISM: Mus musculus
<220> FEATURE:
<221> NAME/KEY: MISC_FEATURE
<222> LOCATION: (92)..(92)
<223> OTHER INFORMATION: Xaa is Selenocysteine residue

<400> SEQUENCE: 31

Met Val Tyr Ile Ser Asn Gly Gln Val Leu Asp Ser Arg Asn Gln Ser
1               5                   10                  15

Pro Trp Arg Val Ser Phe Leu Thr Asp Phe Phe Trp Gly Ile Ala Glu
            20                  25                  30

Phe Val Phe Phe Phe Lys Thr Leu Leu Gln Gln Asp Val Lys Lys
        35                  40                  45

Arg Arg Gly Tyr Gly Ser Ser Asp Ser Arg Tyr Asp Asp Gly Arg
    50                  55                  60

Gly Pro Pro Gly Asn Pro Arg Arg Met Gly Arg Ile Ser His Leu
65                  70                  75                  80

Arg Gly Pro Ser Pro Pro Met Ala Gly Gly Xaa Gly Arg
                85                  90

<210> SEQ ID NO 32
<211> LENGTH: 95
<212> TYPE: PRT
<213> ORGANISM: Gallus gallus
<220> FEATURE:
<221> NAME/KEY: MISC_FEATURE
<222> LOCATION: (93)..(93)
<223> OTHER INFORMATION: Xaa is Selenocystein residue

<400> SEQUENCE: 32

Met Val Tyr Ile Ser Asn Gly Gln Val Leu Asp Asn Arg Ser Arg Ala
1               5                   10                  15

Pro Trp Ser Leu Ser Ala Ile Thr Asp Phe Phe Trp Ser Ile Ala Asp
            20                  25                  30

Phe Val Val Met Phe Phe Gln Ser Ile Ile Gln Pro Asp Leu Arg Arg
        35                  40                  45

Arg Gly Tyr Thr Ser Ser Ser Tyr Leu Gly Gln Ser Asp Gly Arg Gly
    50                  55                  60

Pro Pro Gly Asn Pro Arg Arg Arg Met Gly Arg Ile Asn His Trp Gly
65                  70                  75                  80

Gly Gly Pro Ser Pro Pro Pro Met Ala Gly Gly Gly Xaa Gly Arg
                85                  90                  95

<210> SEQ ID NO 33
<211> LENGTH: 92
<212> TYPE: PRT
<213> ORGANISM: Chlamydomonas reinhardtii
<220> FEATURE:
<221> NAME/KEY: MISC_FEATURE
<222> LOCATION: (91)..(91)
<223> OTHER INFORMATION: Xaa is Selenocysteine residue

<400> SEQUENCE: 33

Met Pro Tyr Ile Ser Arg Thr Gly Thr Val Gln Glu Arg Arg Ser Pro
1               5                   10                  15

Trp Arg Leu Ser Ile Val Val Glu Phe Phe Met Gly Val Trp Gly Ala
            20                  25                  30

Ile Ser Thr Phe Phe Met Thr Met Val Ser Pro Gln Ala His Glu Ala
        35                  40                  45

Tyr Leu Lys Gln Gln Val Lys Lys Lys Asp Pro Pro Arg Thr Thr Gly
```

```
                    50                  55                  60
Gly Pro Arg Ile Ala Gly Leu Asp Asn Ile Gly Gly Gly Gly Ser
 65                  70                  75                  80

His Leu Thr Pro Gly Cys Ala Gly Gly Gly Xaa Gly
                 85                  90

<210> SEQ ID NO 34
<211> LENGTH: 115
<212> TYPE: PRT
<213> ORGANISM: Dictyostelium discoideum
<220> FEATURE:
<221> NAME/KEY: MISC_FEATURE
<222> LOCATION: (112)..(112)
<223> OTHER INFORMATION: Xaa is Selenocysteine residue

<400> SEQUENCE: 34

Met Pro Pro Lys Pro Thr Tyr Val Ser Gly Gly Ser Val Thr Gln Thr
 1               5                  10                  15

Gly Arg Ser Lys Trp Arg Leu Ser Tyr Ile Pro Glu Phe Ile Trp Gly
                 20                  25                  30

Ile Leu Asn Gln Ile Thr Phe Phe Ser Thr Leu Ile Gly Gly Thr
             35                  40                  45

Val Glu Pro Arg Arg Pro Asn Asn Gln Gly Gly Arg Arg Leu
 50                  55                  60

Ala Gly Phe Asp Gly Asn Gly Asn Val Thr Gly Ser Gly Val Gly
 65                  70                  75                  80

Gly Ser Gly Pro Ser Lys Gly Pro Asp Asn Gly Ser Asn Asn Arg Arg
                 85                  90                  95

Gly Asp Met Lys Asn Ile Leu Ala Cys Asn Ser Ala Ser Gly Ser Xaa
                100                 105                 110

Gly Pro Lys
        115

<210> SEQ ID NO 35
<211> LENGTH: 110
<212> TYPE: PRT
<213> ORGANISM: Drosophila melanogaster
<220> FEATURE:
<221> NAME/KEY: MISC_FEATURE
<222> LOCATION: (109)..(109)
<223> OTHER INFORMATION: Xaa is Selenocysteine residue

<400> SEQUENCE: 35

Met Val Tyr Ile Asp His Asn Gly Arg Val Trp Glu Lys Arg Pro Trp
 1               5                  10                  15

Asp Trp Arg Arg Ile Val Glu Leu Phe Val Gly Ile Trp Phe Ala Ile
                 20                  25                  30

Lys Gln Leu Phe Leu Thr Phe Leu Ala Pro Phe Thr Gly Asn Asn Asn
             35                  40                  45

Gln Ala Asn Pro Arg Arg Gly Asn Gly Trp Gly Gly Gly Gly Trp
 50                  55                  60

Gly Gly Gly Gly Gly Gly Gly Gly Gly Gly Gly Arg Pro Gly
 65                  70                  75                  80

Ser Gly Ser Gly Gly Leu Arg Pro Asn Arg Arg Ile Gly Arg Ile Gln
                 85                  90                  95

Pro Thr Met Ser Cys Asn Met Pro Ala Gly Gly Gly Xaa Gly
                100                 105                 110

<210> SEQ ID NO 36
<211> LENGTH: 87
```

```
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Xaa is Selenocysteine residue

<400> SEQUENCE: 36

Met Ala Leu Ala Val Arg Val Val Tyr Cys Gly Ala Xaa Gly Tyr Lys
1               5                   10                  15

Ser Lys Tyr Leu Gln Leu Lys Lys Lys Leu Glu Asp Glu Phe Pro Gly
                20                  25                  30

Arg Leu Asp Ile Cys Gly Glu Gly Thr Pro Gln Ala Thr Gly Phe Phe
            35                  40                  45

Glu Val Met Val Ala Gly Lys Leu Ile His Ser Lys Lys Lys Gly Asp
    50                  55                  60

Gly Tyr Val Asp Thr Glu Ser Lys Phe Leu Lys Leu Val Ala Ala Ile
65                  70                  75                  80

Lys Ala Ala Leu Ala Gln Gly
                85

<210> SEQ ID NO 37
<211> LENGTH: 88
<212> TYPE: PRT
<213> ORGANISM: Mus musculus
<220> FEATURE:
<221> NAME/KEY: MISC_FEATURE
<222> LOCATION: (13)..(13)
<223> OTHER INFORMATION: Xaa is Selenocysteine residue

<400> SEQUENCE: 37

Met Ala Leu Ala Val Arg Val Val Tyr Cys Gly Ala Xaa Gly Tyr Lys
1               5                   10                  15

Pro Lys Tyr Leu Gln Leu Lys Glu Lys Leu Glu His Glu Phe Pro Gly
                20                  25                  30

Cys Leu Asp Ile Cys Gly Glu Gly Thr Pro Gln Val Thr Gly Phe Phe
            35                  40                  45

Glu Val Thr Val Ala Gly Lys Leu Val His Ser Lys Lys Arg Gly Asp
    50                  55                  60

Gly Tyr Val Asp Thr Glu Ser Lys Phe Arg Lys Leu Val Thr Ala Ile
65                  70                  75                  80

Lys Ala Ala Leu Ala Gln Cys Gln
                85

<210> SEQ ID NO 38
<211> LENGTH: 86
<212> TYPE: PRT
<213> ORGANISM: Danio rerio
<220> FEATURE:
<221> NAME/KEY: MISC_FEATURE
<222> LOCATION: (13)..(13)
<223> OTHER INFORMATION: Xaa is Selenocysteine residue

<400> SEQUENCE: 38

Met Thr Val Lys Val His Val Tyr Cys Gly Gly Xaa Gly Tyr Arg
1               5                   10                  15

Pro Lys Phe Ile Lys Leu Lys Thr Leu Leu Glu Asp Glu Phe Pro Asn
                20                  25                  30

Glu Leu Glu Ile Thr Gly Glu Gly Thr Pro Ser Thr Thr Gly Trp Leu
            35                  40                  45

Glu Val Glu Val Asn Gly Lys Leu Val His Ser Lys Lys Asn Gly Asp
    50                  55                  60
```

Gly Phe Val Asp Ser Asp Ser Lys Met Gln Lys Ile Val Thr Ala Ile
65                  70                  75                  80

Glu Gln Ala Met Gly Lys
                85

<210> SEQ ID NO 39
<211> LENGTH: 88
<212> TYPE: PRT
<213> ORGANISM: Chlamydomonas reinhardtii
<220> FEATURE:
<221> NAME/KEY: MISC_FEATURE
<222> LOCATION: (14)..(14)
<223> OTHER INFORMATION: Xaa is Selenocysteine residue

<400> SEQUENCE: 39

Met Ala Pro Val Gln Val His Val Leu Tyr Cys Gly Gly Xaa Gly Tyr
1               5                   10                  15

Gly Ser Arg Tyr Arg Ser Leu Glu Asn Ala Ile Arg Met Lys Phe Pro
            20                  25                  30

Asn Ala Asp Ile Lys Phe Ser Phe Glu Ala Thr Pro Gln Ala Thr Gly
        35                  40                  45

Phe Phe Glu Val Glu Val Asn Gly Glu Leu Val His Ser Lys Lys Asn
    50                  55                  60

Gly Gly His Val Asp Asn Gln Glu Lys Val Glu Arg Ile Phe Ala
65                  70                  75                  80

Lys Ile Gly Glu Ala Leu Ala Lys
                85

<210> SEQ ID NO 40
<211> LENGTH: 80
<212> TYPE: PRT
<213> ORGANISM: Chlamydomonas reinhardtii
<220> FEATURE:
<221> NAME/KEY: MISC_FEATURE
<222> LOCATION: (16)..(16)
<223> OTHER INFORMATION: Xaa is Selenocysteine residue

<400> SEQUENCE: 40

Met Ala Lys Thr Ser Ile Ala Ala Gln Val Val Met Cys Gly Gly Xaa
1               5                   10                  15

Gly Tyr Arg Gly Arg Tyr Arg Ser Leu Val Glu Ala Tyr Arg Arg Arg
            20                  25                  30

Phe Pro Leu Trp Val Pro Thr Ser Pro Thr Thr Gln Arg Cys Ser Leu
        35                  40                  45

Glu Ala Phe Glu Ile Ser Val Asn Gly Gly Leu Val His Ser Lys Glu
    50                  55                  60

Lys Gly Met Gln Phe Pro Tyr Ala Pro Glu Ser Trp Ser Gly Cys Thr
65                  70                  75                  80

<210> SEQ ID NO 41
<211> LENGTH: 94
<212> TYPE: PRT
<213> ORGANISM: Toxoplasma gondii
<220> FEATURE:
<221> NAME/KEY: MISC_FEATURE
<222> LOCATION: (15)..(15)
<223> OTHER INFORMATION: Xaa is Selenocysteine residue

<400> SEQUENCE: 41

Met Glu Gln Thr Val Glu Ile Thr Ile Gln Phe Cys Gly Gly Xaa Gly
1               5                   10                  15

Tyr Arg Pro Tyr Phe Asp Arg Ala Glu Ala Leu Ile Arg Ser Trp Leu

```
            20                  25                  30

Ser Asp Ala Glu Leu Arg Arg Val Ser Ile Glu Gly His Glu Asp Pro
            35                  40                  45

Gly Thr Thr Gly Asn Phe Glu Ile Arg Ile Asn Gly Lys Leu Val His
        50                  55                  60

Ser Lys Lys Thr Lys Lys Gln Gly Phe Leu His Ala Asn Lys Glu Gln
65                  70                  75                  80

Gln Glu Val Val Arg Gln Lys Leu Lys Glu Ala Leu Gly Asn
                85                  90

<210> SEQ ID NO 42
<211> LENGTH: 94
<212> TYPE: PRT
<213> ORGANISM: Neospora caninum
<220> FEATURE:
<221> NAME/KEY: MISC_FEATURE
<222> LOCATION: (15)..(15)
<223> OTHER INFORMATION: Xaa is Selenocysteine residue

<400> SEQUENCE: 42

Met Ala Arg Thr Val Glu Ile Thr Ile Gln Phe Cys Gly Gly Xaa Gly
1               5                   10                  15

Tyr Arg Pro Tyr Phe Asp Arg Ala Glu Ala Leu Ile Arg Ser Trp Phe
            20                  25                  30

Thr Asp Val Tyr Phe Arg His Val Ser Ile Glu Gly His Glu Asp Pro
            35                  40                  45

Gly Thr Thr Gly Asn Phe Glu Ile Arg Ile Asp Gly Val Leu Val His
        50                  55                  60

Ser Lys Lys Thr Arg Arg Gln Gly Phe Leu His Ala Asn Lys Glu Gln
65                  70                  75                  80

Gln Glu Val Val Arg Gln Lys Ile Arg Glu Ala Leu Asp Asn
                85                  90

<210> SEQ ID NO 43
<211> LENGTH: 292
<212> TYPE: PRT
<213> ORGANISM: Toxoplasma gondii
<220> FEATURE:
<221> NAME/KEY: MISC_FEATURE
<222> LOCATION: (291)..(291)
<223> OTHER INFORMATION: Xaa is Selenocysteine residue

<400> SEQUENCE: 43

Met Glu Glu Ala Leu Arg Glu Met Ala His Ser Arg Leu Pro Lys Ala
1               5                   10                  15

Asp Gln Ile Gln Ala Leu Asn Leu Leu Ile Lys Ile Val Asn Asn Val
            20                  25                  30

Leu Ser Pro Pro Gly Ser Ala Asn Pro Glu Glu Leu Glu Arg Phe Arg
            35                  40                  45

Cys Ile Asn Ser Gly Ser Thr Ala Leu Gln Gln Arg Leu Leu Arg His
        50                  55                  60

Gly Pro Val Tyr Glu Asn Leu Leu Leu Ala Leu Gly Phe Tyr Arg Thr
65                  70                  75                  80

Thr Glu Pro Pro Val Ser Arg Pro Leu Pro Gln Pro Asn Gln Glu Tyr
                85                  90                  95

Phe Phe Leu Pro Glu His Ala Asp Arg Ala Gln Leu Leu Ala Asp Leu
            100                 105                 110

Glu Leu Leu Arg Ala Thr Val Ala Ser Leu Glu Thr Glu Gly Asp Asp
            115                 120                 125
```

```
Arg Met Pro Ala Ala Glu Arg Leu Thr Ser Gly Gly Ser Thr Gly Ala
        130                 135                 140

Pro Arg Lys Val Thr Thr Ser Arg Ala Ile Arg Asp Ser Ser Gly
145                 150                 155                 160

Ala Ala His Ala Arg Asn Gln Glu Glu Leu Arg Gln Leu Arg Glu Glu
                165                 170                 175

Gln Arg Ala Arg Phe Glu Gln Arg Ser Glu Thr Gln Ala Thr Gly Gly
            180                 185                 190

Ile Thr Gly Trp Leu Ser Ala Ser Leu Ala Pro Ser Ala Ser Val Ser
        195                 200                 205

Ala Ala Gln Pro Ala Gln Pro Arg His Pro Glu Pro Ala Asp Val Pro
    210                 215                 220

Thr Pro Gly Gly Ser Arg Arg Glu Gly Ser Gly Gly Asn Ala Ala Ser
225                 230                 235                 240

Arg Phe Phe Lys Ser Leu Phe Gly Gly Arg Ser Gly Ser Arg Ser Glu
                245                 250                 255

Glu Gly His Glu Arg Gly Ala Ala Asn Arg Arg Asp Arg Asp Ser Arg
            260                 265                 270

Gly Pro Arg Met Lys Thr Ile Lys Asp Leu Pro Pro Ala Pro Gln Arg
        275                 280                 285

Arg Gly Xaa Gly
        290

<210> SEQ ID NO 44
<211> LENGTH: 266
<212> TYPE: PRT
<213> ORGANISM: Neospora caninum
<220> FEATURE:
<221> NAME/KEY: MISC_FEATURE
<222> LOCATION: (265)..(265)
<223> OTHER INFORMATION: Xaa is Selenocysteine residue

<400> SEQUENCE: 44

Met Glu Glu Ala Leu Gln Glu Val Ala Gln Ser Arg Leu Pro Lys Ala
1               5                   10                  15

Asp Gln Ile Gln Ala Leu Asn Leu Leu Ile Lys Ile Val Thr Asn Ile
            20                  25                  30

Leu Ser Pro Pro Ala Ala Thr Pro Glu Glu Val Glu Arg Phe Arg
        35                  40                  45

Cys Ile Asn Ser Gly Ser Thr Ala Leu Gln Gln Arg Leu Leu Arg His
    50                  55                  60

Gly Pro Val Tyr Glu Asn Leu Leu Leu Ala Leu Gly Phe Tyr Arg Thr
65                  70                  75                  80

Ala Asp Pro Pro Leu Ser Cys Pro Leu Thr Gln Ala Asn Gln Glu Tyr
                85                  90                  95

Phe Phe Leu Pro Asp His Ala Asp Gly Gly Arg Leu Leu Ala Asp Leu
            100                 105                 110

Glu Leu Leu Arg Ala Thr Val Ala Ser Leu Glu Ala Glu Gly Gly Asn
        115                 120                 125

Ala Ile Glu Ser Ser Pro Thr Ala Glu Arg Leu Asn Ser Ala Gly Ser
    130                 135                 140

Gln Gly Ala Gln Arg Lys Val Thr Thr Thr Ser Arg Ala Ile Arg Asp
145                 150                 155                 160

Ser Ser Ala Ser Met His Ala Arg Asn Gln Glu Glu Leu Arg Arg Leu
                165                 170                 175

Arg Glu Glu Gln Arg Leu Arg Phe Glu Gln Arg Ser Glu Ser Glu Pro
            180                 185                 190
```

```
Ala Gly Gly Ile Ala Gly Trp Phe Ser Ser Ser Leu Ala Pro Thr Ala
            195                 200                 205

Ser Leu Pro Ser Ala Gln Pro Ala Gly Pro Ser Leu Phe Gly Ser Arg
210                 215                 220

Ser Gly Ser Arg Ser Glu Glu Gly Arg Glu Arg Asp Gly Thr Ser Gln
225                 230                 235                 240

Arg Gly Gly Asp Ser Arg Gly Pro Arg Met Lys Thr Ile Lys Asp Leu
            245                 250                 255

Pro Pro Ala Pro Arg Arg Gly Xaa Gly
            260                 265
```

<210> SEQ ID NO 45
<211> LENGTH: 195
<212> TYPE: PRT
<213> ORGANISM: Homo sapiens
<220> FEATURE:
<221> NAME/KEY: MISC_FEATURE
<222> LOCATION: (49)..(49)
<223> OTHER INFORMATION: Xaa is Selenocysteine residue

<400> SEQUENCE: 45

```
Met Arg Leu Leu Leu Leu Leu Val Ala Ala Ser Ala Met Val Arg
1               5                   10                  15

Ser Glu Ala Ser Ala Asn Leu Gly Gly Val Pro Ser Lys Arg Leu Lys
                20                  25                  30

Met Gln Tyr Ala Thr Gly Pro Leu Leu Lys Phe Gln Ile Cys Val Ser
            35                  40                  45

Xaa Gly Tyr Arg Arg Val Phe Glu Glu Tyr Met Arg Val Ile Ser Gln
50                  55                  60

Arg Tyr Pro Asp Ile Arg Ile Glu Gly Glu Asn Tyr Leu Pro Gln Pro
65                  70                  75                  80

Ile Tyr Arg His Ile Ala Ser Phe Leu Ser Val Phe Lys Leu Val Leu
                85                  90                  95

Ile Gly Leu Ile Ile Val Gly Lys Asp Pro Phe Ala Phe Gly Met
            100                 105                 110

Gln Ala Pro Ser Ile Trp Gln Trp Gly Gln Glu Asn Lys Val Tyr Ala
            115                 120                 125

Cys Met Met Val Phe Phe Leu Ser Asn Met Ile Glu Asn Gln Cys Met
130                 135                 140

Ser Thr Gly Ala Phe Glu Ile Thr Leu Asn Asp Val Pro Val Trp Ser
145                 150                 155                 160

Lys Leu Glu Ser Gly His Leu Pro Ser Met Gln Gln Leu Val Gln Ile
                165                 170                 175

Leu Asp Asn Glu Met Lys Leu Asn Val His Met Asp Ser Ile Pro His
            180                 185                 190

His Arg Ser
        195
```

<210> SEQ ID NO 46
<211> LENGTH: 163
<212> TYPE: PRT
<213> ORGANISM: Gallus gallus
<220> FEATURE:
<221> NAME/KEY: MISC_FEATURE
<222> LOCATION: (17)..(17)
<223> OTHER INFORMATION: Xaa is Selenocysteine residue

<400> SEQUENCE: 46

Met Ala Tyr Ala Thr Gly Pro Leu Leu Lys Phe Gln Ile Cys Val Ser

```
                1               5                   10                  15
Xaa Gly Tyr Arg Arg Val Phe Glu Glu Tyr Met Arg Val Ile Ser Gln
                    20                  25                  30

Arg Tyr Pro Asp Ile Arg Ile Glu Gly Glu Asn Tyr Leu Pro Gln Pro
                    35                  40                  45

Ile Tyr Arg His Ile Ala Ser Phe Leu Ser Val Phe Lys Leu Val Leu
 50                      55                  60

Ile Gly Leu Ile Ile Val Gly Lys Asp Pro Phe Ala Phe Phe Gly Met
 65                  70                  75                  80

Gln Ala Pro Ser Ile Trp Gln Trp Gly Gln Glu Asn Lys Val Tyr Ala
                    85                  90                  95

Cys Met Met Val Phe Phe Leu Ser Asn Met Ile Glu Asn Gln Cys Met
                    100                 105                 110

Ser Thr Gly Ala Phe Glu Ile Thr Leu Asn Asp Val Pro Val Trp Ser
                    115                 120                 125

Lys Leu Glu Ser Gly His Leu Pro Ser Met Gln Leu Val Gln Ile
        130                 135                 140

Leu Asp Asn Glu Met Lys Leu Asn Val His Met Glu Ser Met Pro His
145                 150                 155                 160

His Arg Ser

<210> SEQ ID NO 47
<211> LENGTH: 255
<212> TYPE: PRT
<213> ORGANISM: Caenorhabditis elegans

<400> SEQUENCE: 47

Met Arg Ile His Asp Glu Leu Gln Lys Gln Asp Met Ser Arg Phe Gly
 1               5                   10                  15

Val Phe Ile Ile Gly Val Leu Phe Phe Met Ser Val Cys Asp Val Leu
                    20                  25                  30

Arg Thr Glu Glu His Ser His Asp Glu Asn His Val His Glu Lys Asp
                    35                  40                  45

Asp Phe Glu Ala Glu Phe Gly Asp Glu Thr Asp Ser Gln Ser Phe Ser
 50                      55                  60

Gln Gly Thr Glu Glu Asp His Ile Glu Val Arg Glu Gln Ser Ser Phe
65                  70                  75                  80

Val Lys Pro Thr Ala Val His His Ala Lys Asp Leu Pro Thr Leu Arg
                    85                  90                  95

Ile Phe Tyr Cys Val Ser Cys Gly Tyr Lys Gln Ala Phe Asp Gln Phe
                    100                 105                 110

Thr Thr Phe Ala Lys Glu Lys Tyr Pro Asn Met Pro Ile Glu Gly Ala
                    115                 120                 125

Asn Phe Ala Pro Val Leu Trp Lys Ala Tyr Val Ala Gln Ala Leu Ser
        130                 135                 140

Phe Val Lys Met Ala Val Leu Val Leu Val Leu Gly Gly Ile Asn Pro
145                 150                 155                 160

Phe Glu Arg Phe Gly Leu Gly Tyr Pro Gln Ile Leu Gln His Ala His
                    165                 170                 175

Gly Asn Lys Met Ser Ser Cys Met Leu Val Phe Met Leu Gly Asn Leu
                    180                 185                 190

Val Glu Gln Ser Leu Ile Ser Thr Gly Ala Phe Glu Val Tyr Leu Gly
                    195                 200                 205

Asn Glu Gln Ile Trp Ser Lys Ile Glu Ser Gly Arg Val Pro Ser Pro
        210                 215                 220
```

```
Gln Glu Phe Met Gln Leu Ile Asp Ala Gln Leu Ala Val Leu Gly Lys
225                 230                 235                 240

Ala Pro Val Asn Thr Glu Ser Phe Gly Glu Phe Gln Gln Thr Val
                245                 250                 255

<210> SEQ ID NO 48
<211> LENGTH: 232
<212> TYPE: PRT
<213> ORGANISM: Oryza sativa

<400> SEQUENCE: 48

Met Asp Arg Val Gln Leu Val Leu Leu Gly Leu Pro Ile Leu Leu Phe
1               5                   10                  15

Cys Ser Asp Leu Val Thr Leu Phe Gly Pro Glu Gln Leu Pro Thr Pro
                20                  25                  30

Gln Pro Asp Leu Pro Pro His Pro Ser Pro Asp Ala Ala Ser Asp Ala
            35                  40                  45

Val Gln Pro Asp Asp Ile Ala Ala Asp Ala Ala Ala Ser Ala Gln Ile
        50                  55                  60

Ala Glu Pro Gln Val Asp Gly Pro Ala Ser Gly Thr Thr Val Glu Leu
65                  70                  75                  80

Lys Phe Cys Ala Ser Cys Ser Tyr Arg Gly Asn Ala Val Thr Val Lys
                85                  90                  95

Lys Met Leu Glu Thr Ser Phe Pro Gly Ile His Val Leu Glu Asn
            100                 105                 110

Tyr Pro Pro Pro Phe Pro Lys Arg Ala Leu Ser Lys Ala Val Pro Phe
                115                 120                 125

Leu Gln Val Gly Ala Met Ala Thr Leu Met Ala Gly Asp Gln Ile Phe
        130                 135                 140

Pro Arg Phe Gly Met Val Pro Pro Trp Tyr Tyr Ser Leu Arg Ala
145                 150                 155                 160

Asn Arg Phe Gly Thr Met Ala Thr Ile Trp Leu Phe Gly Asn Phe Ala
                165                 170                 175

Gln Ser Phe Leu Gln Ser Ser Gly Ala Phe Glu Val Tyr Cys Asn Gly
            180                 185                 190

Gln Leu Val Phe Ser Lys Leu Ser Glu Gln Arg Phe Pro Ser Glu Phe
        195                 200                 205

Glu Leu Arg Glu Leu Ile Gly Asn Arg Leu Pro Asp Ser Gln Phe Gly
210                 215                 220

Lys Asn Leu Glu Lys Val Trp Ser
225                 230

<210> SEQ ID NO 49
<211> LENGTH: 209
<212> TYPE: PRT
<213> ORGANISM: Arabidopsis thaliana

<400> SEQUENCE: 49

Met Asp Lys Thr Gln Leu Ile Leu Leu Gly Leu Pro Ile Phe Leu Leu
1               5                   10                  15

Cys Ser Asp Leu Phe Asn Leu Phe Thr Pro Pro Pro Lys Ser Gln
                20                  25                  30

His Gln Ser Pro Pro Ser Ile Ser Glu Thr Leu Asp Phe Pro Ala Gln
            35                  40                  45

Lys Ser Thr Gly Val Gly Tyr Gly Asn Thr Val Glu Ile Asn Phe Cys
        50                  55                  60
```

```
Ile Ser Cys Ser Tyr Lys Gly Thr Ala Val Ser Met Lys Lys Met Leu
 65                  70                  75                  80

Glu Ser Val Phe Pro Gly Leu Asp Val Val Leu Ala Asn Tyr Pro Ala
                 85                  90                  95

Pro Ala Pro Lys Arg Ile Leu Ala Lys Val Val Pro Val Ala Gln Val
            100                 105                 110

Gly Val Ile Gly Leu Ile Met Gly Gly Glu Gln Ile Phe Pro Met Ile
        115                 120                 125

Gly Ile Ala Gln Pro Pro Ala Trp Tyr His Ser Leu Arg Ala Asn Arg
    130                 135                 140

Phe Gly Ser Met Ala Ser Thr Trp Leu Leu Gly Asn Phe Leu Gln Ser
145                 150                 155                 160

Phe Leu Gln Ser Ser Gly Ala Phe Glu Val Ser Cys Asn Gly Glu Leu
                165                 170                 175

Val Phe Ser Lys Leu Lys Glu Gly Arg Phe Pro Gly Glu Ile Glu Leu
                180                 185                 190

Arg Asp Leu Ser Ser Gly Thr Met Thr Lys Pro Phe Val Thr Gly Ser
                195                 200                 205

Tyr

<210> SEQ ID NO 50
<211> LENGTH: 235
<212> TYPE: PRT
<213> ORGANISM: Chlamydomonas reinhardtii
<220> FEATURE:
<221> NAME/KEY: MISC_FEATURE
<222> LOCATION: (61)..(61)
<223> OTHER INFORMATION: Xaa is Selenocysteine residue

<400> SEQUENCE: 50

Met Gln Gly Leu His Lys Gly Ala Ile Leu Leu Gly Ile Val Ala Leu
  1               5                  10                  15

Phe Ile Gly Ala Asp Cys Phe Gly Val Met Gly Gly Ser Lys Ala Pro
                 20                  25                  30

Ser Gln Ala Arg Val Gln Ser Ala Met Asp Pro Asp Gly Gly Leu Ser
             35                  40                  45

Leu Gly Gly Lys Leu His Val Ser Phe Cys Asn Ser Xaa Gly Met Arg
 50                  55                  60

Gly Ala Phe Val Gln Val Met Glu Leu Ala Arg Arg Tyr Pro Gly
 65                  70                  75                  80

Leu Glu Val Val Gly Thr Pro Tyr Pro Leu Pro Ala Trp Lys Val Pro
                 85                  90                  95

Val Val Lys Ala Leu Gln Val Val Gln Phe Gly Leu Leu Gly Met Cys
            100                 105                 110

Leu Ala Gly Asp Lys Val Phe Ala Ala Leu Gly Val Pro Val Pro Ala
        115                 120                 125

Trp Tyr Thr Gln Asn Val Ala Ser Asn Arg Phe Gly Ala Ala Met Gly
    130                 135                 140

Val Trp Phe Val Gly Asn Met Val Val Thr Asn Met Gln Asn Thr Gly
145                 150                 155                 160

Ala Phe Glu Val Phe Phe Asn Gly Asp Leu Ile Phe Ser Lys Leu Ala
                165                 170                 175

Glu Gly Arg Met Pro Ser Val Pro Glu Leu Ile Ser Pro Met Gln Ala
                180                 185                 190

Phe Phe Glu Gly Pro Ala Gly Leu His Val Gly Gly Ala Gly Ala Ser
                195                 200                 205
```

```
Arg Pro Gly Leu Thr Gly Ala Gly Met Gly His Gly Pro Glu Leu Ser
    210                 215                 220

Gly Val Gly Ala Ala Ala Val Gly Leu Thr Gly
225                 230                 235

<210> SEQ ID NO 51
<211> LENGTH: 252
<212> TYPE: PRT
<213> ORGANISM: Toxoplasma gondii
<220> FEATURE:
<221> NAME/KEY: MISC_FEATURE
<222> LOCATION: (97)..(97)
<223> OTHER INFORMATION: Xaa is Selenocysteine residue

<400> SEQUENCE: 51

Met Val Pro Ser Glu Gly Ala Ala Pro Ser Gly Gly Gly Gly Ala Ser
1               5                   10                  15

Thr Val Ser Pro Gly Thr Ser Ser Pro Leu Pro Ser Ser Ser Ser Thr
            20                  25                  30

Trp Val Val Ala Ala Val Val Leu Leu Leu Ser Leu Pro Leu Gly Thr
        35                  40                  45

Val Leu Asp Gly Leu Phe Leu Ser Gly Asn His Ala Pro Met Gln Ser
    50                  55                  60

Ala Pro Ser Thr Leu Val Asp Arg Phe Phe Thr Pro His Asn Pro Leu
65                  70                  75                  80

Pro Thr Gly Ile Ser Pro His Gln Val Thr Val Gln Leu Cys Thr Ser
                85                  90                  95

Xaa Ser Ser Ala Gly Ala Leu Arg Gln Leu Ala Glu Phe Leu Ser Phe
            100                 105                 110

Gln Leu Ser His Leu Pro Gly Phe Arg Phe Val Ala Val Glu Tyr Lys
        115                 120                 125

Pro Ser Leu Phe His Gln Ala Leu Gly Arg Leu Leu Asp Ala Leu Ser
    130                 135                 140

Trp Ala Ala Leu Ala Leu Val Val Phe Val Arg Pro Ile Cys Ser Thr
145                 150                 155                 160

Leu Gly Leu Thr Gln Gln Arg Gly Glu Glu Arg Gly Ala Gln Thr Glu
                165                 170                 175

Gln Leu Pro Pro Trp Ala Glu Ala Leu Glu Asn Asn Arg Val Ala Ala
            180                 185                 190

Ile Val Thr Ala Phe Phe Gly Val Gln Val Val Arg Ser Val Leu Ile
        195                 200                 205

Pro Asn Asn Ala Phe Glu Ile Phe Ile Gly Glu Asn Leu Leu Trp Ser
    210                 215                 220

Thr Leu Asp Ser Gly Arg Met Pro Asn Gly Arg Asp Leu Met Gln Arg
225                 230                 235                 240

Leu Glu Thr Ile Gly Val Ser Val Arg Glu Pro Met
                245                 250

<210> SEQ ID NO 52
<211> LENGTH: 267
<212> TYPE: PRT
<213> ORGANISM: Neospora caninum
<220> FEATURE:
<221> NAME/KEY: MISC_FEATURE
<222> LOCATION: (113)..(113)
<223> OTHER INFORMATION: Xaa is Selenocysteine residue

<400> SEQUENCE: 52

Met Ala Val Pro Gln Gly Val Val Pro Pro Gly Gly Gly Asp Ser Gly
1               5                   10                  15
```

Gly Ser Arg Gly His Ser Val Thr Ala Asp Ala Thr Thr Pro Pro Ala
            20                  25                  30

Thr Gln Thr Ser Ser Pro Ala Ala Pro Pro Thr Ser Leu Ser Ser Thr
        35                  40                  45

Trp Ile Val Ala Leu Val Leu Leu Leu Ser Leu Pro Leu Gly Thr
 50                  55                  60

Val Ile Asp Gly Leu Phe Ser Pro Ser Gly Asn Arg Gly Ser Ser Ser
 65                  70                  75                  80

Ala Ser Pro Val Leu Phe Glu Gln Leu Phe Thr Pro His Asn Pro Leu
                85                  90                  95

Pro Ala Asp Val Gly Pro His Gln Val Thr Val Gln Leu Cys Thr Ser
            100                 105                 110

Xaa Ser Thr Ala Gly Ala Leu Arg Gln Leu Ala Asp Phe Leu Ser Phe
            115                 120                 125

Gln Leu Asn His Leu Pro Gly Phe Arg Leu Val Ala Val Asp Tyr Arg
        130                 135                 140

Pro Ser Leu Phe His Gln Ala Leu Gly Arg Leu Leu Asp Val Leu Ser
145                 150                 155                 160

Trp Ala Ala Leu Ala Leu Val Val Phe Val Arg Pro Ile Cys Ala Ala
                165                 170                 175

Leu Gly Leu Thr Gln Arg Gly Gly Glu Gly Ser Ala Gln Ala Glu Gln
            180                 185                 190

Leu Pro Pro Trp Ala Glu Ala Leu Glu Asn Asn Arg Val Thr Ala Ile
        195                 200                 205

Ile Ser Ala Phe Phe Gly Ala Gln Val Val Arg Ser Val Leu Ile Pro
    210                 215                 220

Ser Phe Ser Phe Glu Ile Tyr Phe Gly Pro Asn Leu Leu Trp Ser Thr
225                 230                 235                 240

Val His Asn Gly Arg Met Pro Asn Gly Arg Asp Leu Leu Arg Glu Leu
                245                 250                 255

Glu Ala Leu Gly Val Arg Val Arg Asp Pro Met
            260                 265

<210> SEQ ID NO 53
<211> LENGTH: 608
<212> TYPE: DNA
<213> ORGANISM: Toxoplasma gondii

<400> SEQUENCE: 53
gtacgtttgg caggatgcgt tatgtggaga agctggaagg cgaaatggag gatttcaaga     60
aaacagagga gttcaaagag ctagagaagg aagctgcaga tcgagaaaga ggcatccaac    120
cagaacatag gcgaacctgg cagttcaggg gaaccctccc gcagaatccg catgtggcac    180
ctagattccg gcccaacgta tatgatcgct atcaaatccg gcgaggcaga ggggctgat    240 gctaaaagaa gaacatgtgc aaacggttgc acatgttttg acgagtggca acactctgcg    300
aagcaccata acttttcgac ccttgttcat aaataccgtc ggtgtgccaa cgacgctgcc    360
ctaccccaat tctggctcac cttttggagt gtgggaagcg gcgacaatga ccgttctcga    420
cagcgaagta tttcaagtaa acaacgatga gttgggaaga attagttccc tccacgtctg    480
acggtgttgt caatgagagc gcaggaaacg tggtcatgaa tgacgaggca cagagaaacc    540
gttttcggat cggtgcctct gaaaggtggt cgaccccctgc ctcttacacc tcagttttta    600
cgctgctg                                                             608

<210> SEQ ID NO 54
<211> LENGTH: 76
<212> TYPE: PRT
<213> ORGANISM: Toxoplasma gondii
<220> FEATURE:
<221> NAME/KEY: MISC_FEATURE
<222> LOCATION: (75)..(75)
<223> OTHER INFORMATION: Xaa is Selenocysteine residue

<400> SEQUENCE: 54

```
Met Arg Tyr Val Glu Lys Leu Glu Gly Glu Met Glu Asp Phe Lys Lys
1               5                   10                  15

Thr Glu Glu Phe Lys Glu Leu Glu Lys Glu Ala Ala Asp Arg Glu Arg
            20                  25                  30

Gly Ile Gln Pro Glu His Arg Arg Thr Trp Gln Phe Arg Gly Thr Leu
        35                  40                  45

Pro Gln Asn Pro His Val Ala Pro Arg Phe Arg Pro Asn Val Tyr Asp
    50                  55                  60

Arg Tyr Gln Ile Arg Arg Gly Arg Gly Gly Xaa Cys
65                  70                  75
```

<210> SEQ ID NO 55
<211> LENGTH: 66
<212> TYPE: DNA
<213> ORGANISM: Homo sapiens

<400> SEQUENCE: 55

```
ggagacagaa tgaagcgctc agcatcccgg gaatacttct cttgctgaga gccgatgccc    60
gtcccc                                                              66
```

<210> SEQ ID NO 56
<211> LENGTH: 66
<212> TYPE: DNA
<213> ORGANISM: Mus musculus

<400> SEQUENCE: 56

```
ggagacagaa tgaagcgctc agtatcccgg gagcatctcc cttgctgagg gccgacgcca    60
gtctcc                                                              66
```

<210> SEQ ID NO 57
<211> LENGTH: 69
<212> TYPE: DNA
<213> ORGANISM: Rattus norvegicus

<400> SEQUENCE: 57

```
ggagacagaa tgaagcgctc agcatcccgg gagcataaac tctcttgctg agggccgacg    60
ccggtctcc                                                           69
```

<210> SEQ ID NO 58
<211> LENGTH: 71
<212> TYPE: DNA
<213> ORGANISM: Danio rerio

<400> SEQUENCE: 58

```
gcgggacgtt aatgatgtcc acagctgtaa aagcctgaga gcggctgcgg actgatgatc    60
cgcgtcctcg c                                                        71
```

<210> SEQ ID NO 59
<211> LENGTH: 866
<212> TYPE: DNA
<213> ORGANISM: Mus musculus -continued

```
<400> SEQUENCE: 59
gagtacggat tccacgtttg agtcccaaca tctccagtat gtgtgctgct cggctctccg      60
cggcggcaca gtccaccgtg tatgccttct ccgcgcgccc gctgacgggc ggggagcctg     120
tgagcctggg ctccctgcgg ggcaaggtgc tgctcattga aatgtcgcg tctctctgag     180
gcaccacgat ccgggactac accgagatga acgatctgca aaagcgtctg ggacctcgtg     240
gactggtggt gctcggtttc ccgtgcaatc agttcggaca ccaggagaat ggcaagaatg     300
aagagattct gaattccctc aagtacgtcc gacctggtgg cgggttcgag cccaatttta    360
cattgtttga aagtgcgaaa gtgaatggtg agaaggctca cccgctcttt accttcctgc    420
ggaatgcctt gccaacaccc agtgacgacc ccactgcgct catgaccgac cccaagtaca    480
tcatttggtc tccggtgtgc cgcaacgaca ttgcctggaa ctttgagaag ttcctggtgg    540
gccccgacgg tgttcccgtg cgcaggtaca gccgccgctt cgtaccatc gacatcgaac    600
ctgacataga aaccctgctg tcccagcagt ctggcaactc catgatgatg atgatgatgt    660
aaggcggccc tggcattggc ttggtgatta ctggctgcac tctgggggc ggttcttcca     720
tgatggtgtt tcctctaaat ttgcacggag aaacacctga tttccaggaa aatcccctca    780
gatgggcgct ggtcccatcc attcccgatg cctttccacc taatgaaagg tggtttcact    840
actaagaata aagtgctgaa tatcag                                          866

<210> SEQ ID NO 60
<211> LENGTH: 201
<212> TYPE: PRT
<213> ORGANISM: Mus musculus
<220> FEATURE:
<221> NAME/KEY: MISC_FEATURE
<222> LOCATION: (47)..(47)
<223> OTHER INFORMATION: Xaa is Selenocysteine residue

<400> SEQUENCE: 60

Met Cys Ala Ala Arg Leu Ser Ala Ala Gln Ser Thr Val Tyr Ala
 1               5                  10                  15

Phe Ser Ala Arg Pro Leu Thr Gly Gly Glu Pro Val Ser Leu Gly Ser
                20                  25                  30

Leu Arg Gly Lys Val Leu Leu Ile Glu Asn Val Ala Ser Leu Xaa Gly
            35                  40                  45

Thr Thr Ile Arg Asp Tyr Thr Glu Met Asn Asp Leu Gln Lys Arg Leu
        50                  55                  60

Gly Pro Arg Gly Leu Val Val Leu Gly Phe Pro Cys Asn Gln Phe Gly
65                  70                  75                  80

His Gln Glu Asn Gly Lys Asn Glu Glu Ile Leu Asn Ser Leu Lys Tyr
                85                  90                  95

Val Arg Pro Gly Gly Gly Phe Glu Pro Asn Phe Thr Leu Phe Glu Lys
            100                 105                 110

Cys Glu Val Asn Gly Glu Lys Ala His Pro Leu Phe Thr Phe Leu Arg
        115                 120                 125

Asn Ala Leu Pro Thr Pro Ser Asp Asp Pro Thr Ala Leu Met Thr Asp
    130                 135                 140

Pro Lys Tyr Ile Ile Trp Ser Pro Val Cys Arg Asn Asp Ile Ala Trp
145                 150                 155                 160

Asn Phe Glu Lys Phe Leu Val Gly Pro Asp Gly Val Pro Val Arg Arg
                165                 170                 175

Tyr Ser Arg Arg Phe Arg Thr Ile Asp Ile Glu Pro Asp Ile Glu Thr
            180                 185                 190
```

Leu Leu Ser Gln Gln Ser Gly Asn Ser
        195                 200

<210> SEQ ID NO 61
<211> LENGTH: 5214
<212> TYPE: DNA
<213> ORGANISM: Artificial Sequence
<220> FEATURE:
<223> OTHER INFORMATION: pEGFP-C3 vector

<400> SEQUENCE: 61

| | | | |
|---|---|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta acaactccgc cccattgacg caaatgggcg gtaggcgtgt | 540 |
| acggtgggag gtctatataa gcagagctgg tttagtgaac cgtcagatcc gctagcgcta | 600 |
| ccggtcgcca ccatggtgag caagggcgag gagctgttca ccggggtggt gcccatcctg | 660 |
| gtcgagctgg acggcgacgt aaacggccac aagttcagcg tgtccggcga gggcgagggc | 720 |
| gatgccacct acggcaagct gaccctgaag ttcatctgca ccaccggcaa gctgcccgtg | 780 |
| ccctggccca ccctcgtgac caccctgacc tacggcgtgc agtgcttcag ccgctacccc | 840 |
| gaccacatga agcagcacga cttcttcaag tccgccatgc ccgaaggcta cgtccaggag | 900 |
| cgcaccatct tcttcaagga cgacggcaac tacaagaccc gcgccgaggt gaagttcgag | 960 |
| ggcgacaccc tggtgaaccg catcgagctg aagggcatcg acttcaagga ggacggcaac | 1020 |
| atcctggggc acaagctgga gtacaactac aacagccaca acgtctatat catggccgac | 1080 |
| aagcagaaga acggcatcaa ggtgaacttc aagatccgcc acaacatcga ggacggcagc | 1140 |
| gtgcagctcg ccgaccacta ccagcagaac acccccatcg gcgacggccc cgtgctgctg | 1200 |
| cccgacaacc actacctgag cacccagtcc gccctgagca agaccccaa cgagaagcgc | 1260 |
| gatcacatgg tcctgctgga gttcgtgacc gccgccggga tcactctcgg catggacgag | 1320 |
| ctgtacaagt actcagatct cgagctcaag cttcgaattc aaatggcccc ccacggaaga | 1380 |
| aagcgtaagg cggggccgc gcctatgag acggtggaca agcgcgagaa actggcggag | 1440 |
| ggcgcgaccg tggtcattga gcattgtacg agctgacgcg tgtacggccg ccatgctgct | 1500 |
| gccttgagcc aggctctgca actggaggcc ccagagctac ctgtgcaagt gaacccgtcc | 1560 |
| aaaccgcgga ggggcagctt cgaggtgacg ctgctgcgct cggacaacag ccgtgttgaa | 1620 |
| ctctggactg gtattaagaa gggccctcca cgaaagctca aatttcctga gcctcaagag | 1680 |
| gtggttgaag aattgaagaa gtacctttca taaagaggtt gggaaagagt cctcatgttg | 1740 |
| agctttcagt ccctggagat gttgaagcat ttgggatggt gcatggccaa acttaagcta | 1800 |
| tgcacctgaa gccatagttt cttcctcacc agaagtgatg gttcagttgt gaggcagccc | 1860 |
| tccagcaaga caggatccac cggatctaga taactgatca taatcagcca taccacattt | 1920 |
| gtagaggttt tacttgcttt aaaaaacctc ccacacctcc cctgaacct gaaacataaa | 1980 |
| atgaatgcaa ttgttgttgt taacttgttt attgcagctt ataatggtta caaataaagc | 2040 |

```
aatagcatca caaatttcac aaataaagca ttttttcac tgcattctag ttgtggtttg    2100
tccaaactca tcaatgtatc ttaacgcgta aattgtaagc gttaatattt tgttaaaatt    2160
cgcgttaaat ttttgttaaa tcagctcatt ttttaaccaa taggccgaaa tcggcaaaat    2220
cccttataaa tcaaaagaat agaccgagat agggttgagt gttgttccag tttggaacaa    2280
gagtccacta ttaaagaacg tggactccaa cgtcaagggg cgaaaaaccg tctatcaggg    2340
cgatggccca ctacgtgaac catcaccta atcaagtttt tggggtcga ggtgccgtaa     2400 agcactaaat cggaacccta aagggagccc ccgatttaga gcttgacggg gaaagccggc    2460
gaacgtggcg agaaaggaag ggaagaaagc gaaaggagcg ggcgctaggg cgctggcaag    2520
tgtagcggtc acgctgcgcg taaccaccac acccgccgcg cttaatgcgc cgctacaggg    2580
cgcgtcaggt ggcacttttc ggggaaatgt gcgcggaacc cctatttgtt tatttttcta    2640
aatacattca aatatgtatc cgctcatgag acaataaccc tgataaatgc ttcaataata    2700
ttgaaaaagg aagagtcctg aggcggaaag aaccagctgt ggaatgtgtg tcagttaggg    2760
tgtggaaagt ccccaggctc cccagcaggc agaagtatgc aaagcatgca tctcaattag    2820
tcagcaacca ggtgtggaaa gtccccaggc tccccagcag gcagaagtat gcaaagcatg    2880
catctcaatt agtcagcaac catagtcccg cccctaactc cgcccatccc gcccctaact    2940
ccgcccagtt ccgcccattc tccgcccat ggctgactaa tttttttat ttatgcagag      3000 gccgaggccg cctcggcctc tgagctattc cagaagtagt gaggaggctt ttttggaggc    3060
ctaggctttt gcaaagatcg atcaagagac aggatgagga tcgtttcgca tgattgaaca    3120
agatggattg cacgcaggtt ctccggccgc ttgggtggag aggctattcg gctatgactg    3180
ggcacaacag acaatcggct gctctgatgc cgccgtgttc cggctgtcag cgcaggggcg    3240
cccggttctt tttgtcaaga ccgacctgtc cggtgccctg aatgaactgc aagacgaggc    3300
agcgcggcta tcgtggctgg ccacgacggg cgttccttgc gcagctgtgc tcgacgttgt    3360
cactgaagcg ggaagggact ggctgctatt gggcgaagtg ccggggcagg atctcctgtc    3420
atctcacctt gctcctgccg agaaagtatc catcatggct gatgcaatgc ggcggctgca    3480
tacgcttgat ccggctacct gcccattcga ccaccaagcg aaacatcgca tcgagcgagc    3540
acgtactcgg atggaagccg gtcttgtcga tcaggatgat ctggacgaag agcatcaggg    3600
gctcgcgcca gccgaactgt tcgccaggct caaggcgagc atgcccgacg gcgaggatct    3660
cgtcgtgacc catggcgatg cctgcttgcc gaatatcatg gtggaaaatg gccgcttttc    3720
tggattcatc gactgtggcc ggctgggtgt ggcggaccgc tatcaggaca tagcgttggc    3780
tacccgtgat attgctgaag agcttggcgg cgaatgggct gaccgcttcc tcgtgcttta    3840
cggtatcgcc gctcccgatt cgcagcgcat cgccttctat cgccttcttg acgagttctt    3900
ctgagcggga ctctgggtt cgaaatgacc gaccaagcga cgcccaacct gccatcacga    3960
gatttcgatt ccaccgccgc cttctatgaa aggttgggct tcggaatcgt tttccgggac    4020
gccggctgga tgatcctcca gcgcggggat ctcatgctgg agttcttcgc ccaccctagg    4080
gggaggctaa ctgaaacacg gaaggagaca ataccggaag gaacccgcgc tatgacggca    4140 ataaaagac agaataaaac gcacggtgtt gggtcgtttg ttcataaacg cggggttcgg     4200
tcccagggct ggcactctgt cgataccca ccgagaccc attggggcca atacgcccgc      4260
gtttcttcct tttccccacc ccaccccca agttcgggtg aaggcccagg gctcgcagcc     4320
aacgtcgggg cggcaggccc tgccatagcc tcaggttact catatatact ttagattgat    4380
ttaaaacttc atttttaatt taaaaggatc taggtgaaga tccttttttga taatctcatg    4440
```

```
accaaaatcc cttaacgtga gttttcgttc cactgagcgt cagacccgt agaaaagatc    4500 aaaggatctt cttgagatcc ttttttctg cgcgtaatct gctgcttgca aacaaaaaaa    4560
ccaccgctac cagcggtggt ttgtttgccg gatcaagagc taccaactct ttttccgaag    4620
gtaactggct tcagcagagc gcagatacca aatactgtcc ttctagtgta gccgtagtta    4680
ggccaccact tcaagaactc tgtagcaccg cctacatacc tcgctctgct aatcctgtta    4740
ccagtggctg ctgccagtgg cgataagtcg tgtcttaccg ggttggactc aagacgatag    4800
ttaccggata aggcgcagcg gtcgggctga cgggggtt cgtgcacaca gcccagcttg     4860
gagcgaacga cctacaccga actgagatac ctacagcgtg agctatgaga aagcgccacg    4920
cttcccgaag ggagaaaggc ggacaggtat ccggtaagcg gcaggtcgg aacaggagag    4980 cgcacgaggg agcttccagg gggaaacgcc tggtatcttt atagtcctgt cgggtttcgc    5040
cacctctgac ttgagcgtcg attttttgtga tgctcgtcag ggggcggag cctatggaaa    5100 aacgccagca acgcggcctt tttacggttc ctggcctttt gctggccttt tgctcacatg    5160
ttctttcctg cgttatcccc tgattctgtg gataaccgta ttaccgccat gcat          5214
```

```
<210> SEQ ID NO 62
<211> LENGTH: 1101
<212> TYPE: DNA
<213> ORGANISM: Mus musculus

<400> SEQUENCE: 62
```

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtac    720
tcagatctcg agctcaagct tcgaattcaa atggcccccc acggaagaaa gcgtaaggcg    780
ggggccgcgc ctatggagac ggtggacaag cgcgagaaac tggcggaggg cgcgaccgtg    840
gtcattgagc attgtacgag ctgacgcgtg tacggccgcc atgctgctgc cttgagccag    900
gctctgcaac tggaggcccc agagctacct gtgcaagtga acccgtccaa accgcggagg    960
ggcagcttcg aggtgacgct gctgcgctcg gacaacagcc gtgttgaact ctggactggt   1020
attaagaagg gccctccacg aaagctcaaa tttcctgagc ctcaagaggt ggttgaagaa   1080
ttgaagaagt acctttcata a                                              1101
```

```
<210> SEQ ID NO 63
<211> LENGTH: 366
<212> TYPE: PRT
<213> ORGANISM: Mus musculus
<220> FEATURE:
<221> NAME/KEY: MISC_FEATURE
```

<222> LOCATION: (288)..(288)
<223> OTHER INFORMATION: Xaa is Selenocysteine residue

<400> SEQUENCE: 63

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Tyr
225                 230                 235                 240

Ser Asp Leu Glu Leu Lys Leu Arg Ile Gln Met Ala Pro His Gly Arg
                245                 250                 255

Lys Arg Lys Ala Gly Ala Ala Pro Met Glu Thr Val Asp Lys Arg Glu
            260                 265                 270

Lys Leu Ala Glu Gly Ala Thr Val Val Ile Glu His Cys Thr Ser Xaa
        275                 280                 285

Arg Val Tyr Gly Arg His Ala Ala Leu Ser Gln Ala Leu Gln Leu
290                 295                 300

Glu Ala Pro Glu Leu Pro Val Gln Val Asn Pro Ser Lys Pro Arg Arg
305                 310                 315                 320

Gly Ser Phe Glu Val Thr Leu Leu Arg Ser Asp Asn Ser Arg Val Glu
                325                 330                 335

Leu Trp Thr Gly Ile Lys Lys Gly Pro Pro Arg Lys Leu Lys Phe Pro
            340                 345                 350

Glu Pro Gln Glu Val Val Glu Glu Leu Lys Lys Tyr Leu Ser
        355                 360                 365

<210> SEQ ID NO 64
<211> LENGTH: 1305
<212> TYPE: DNA
<213> ORGANISM: Mus musculus

<400> SEQUENCE: 64

```
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccctgaccta cggcgtgcag tgcttcagcc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtac      720
tcagatctcg agatggatcg cgatgaggaa cctctgtccg cgaggccggc gctggagacc      780
gagagcctgc gattcctgca cgtgacagtg ggctccctgc tggccagcta tggctggtac      840
atcctcttca gctgcatcct actctacatt gtcatccaga ggctctccct tcgactgagg      900
gctttgaggc agagacagct ggaccaagcc gagactgttc tggaacctga tgttgttgtt      960
aagcggcaag aggctttagc agctgctcgt tgagaatgc aggaagatct aaatgcccaa     1020
gttgaaaaac ataaggaaaa actaagacag cttgaagaag agaaagaag acagaagatt     1080
gaaatgtggg acagcatgca agaaggcaga agttacaaaa gaaattcagg aaggcctcag     1140
gaagaagatg gtcctggacc ttctacttca tctgtcatct ccaaaggaaa atctgacaaa     1200
aagcctttgc gaggaggtgg ttataaccct ctgacgggtg aagggggtgg aacctgctcc     1260
tggagacctg gacgcagggg cccatcatct ggcggctgaa actaa                      1305
```

<210> SEQ ID NO 65
<211> LENGTH: 434
<212> TYPE: PRT
<213> ORGANISM: Mus musculus
<220> FEATURE:
<221> NAME/KEY: MISC_FEATURE
<222> LOCATION: (433)..(433)
<223> OTHER INFORMATION: Xaa is Selenocysteine residue

<400> SEQUENCE: 65

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
```

```
                  115                 120                 125
Ile Asp Phe Lys Glu Asp Gly Asn Ile Leu Gly His Lys Leu Glu Tyr
130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
210                 215                 220
Val Thr Ala Ala Gly Ile Thr Leu Gly Met Asp Glu Leu Tyr Lys Tyr
225                 230                 235                 240
Ser Asp Leu Glu Met Asp Arg Asp Glu Glu Pro Leu Ser Ala Arg Pro
                245                 250                 255
Ala Leu Glu Thr Glu Ser Leu Arg Phe Leu His Val Thr Val Gly Ser
            260                 265                 270
Leu Leu Ala Ser Tyr Gly Trp Tyr Ile Leu Phe Ser Cys Ile Leu Leu
        275                 280                 285
Tyr Ile Val Ile Gln Arg Leu Ser Leu Arg Leu Arg Ala Leu Arg Gln
290                 295                 300
Arg Gln Leu Asp Gln Ala Glu Thr Val Leu Glu Pro Asp Val Val Val
305                 310                 315                 320
Lys Arg Gln Glu Ala Leu Ala Ala Ala Arg Leu Arg Met Gln Glu Asp
                325                 330                 335
Leu Asn Ala Gln Val Glu Lys His Lys Glu Lys Leu Arg Gln Leu Glu
            340                 345                 350
Glu Glu Lys Arg Arg Gln Lys Ile Glu Met Trp Asp Ser Met Gln Glu
        355                 360                 365
Gly Arg Ser Tyr Lys Arg Asn Ser Gly Arg Pro Gln Glu Glu Asp Gly
370                 375                 380
Pro Gly Pro Ser Thr Ser Ser Val Ile Ser Lys Gly Lys Ser Asp Lys
385                 390                 395                 400
Lys Pro Leu Arg Gly Gly Tyr Asn Pro Leu Thr Gly Glu Gly Gly Gly
                405                 410                 415
Gly Thr Cys Ser Trp Arg Pro Gly Arg Arg Gly Pro Ser Ser Gly Gly
            420                 425                 430
Xaa Asn

<210> SEQ ID NO 66
<211> LENGTH: 1170
<212> TYPE: DNA
<213> ORGANISM: Mus musculus

<400> SEQUENCE: 66
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
```

```
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtac      720
tcagatctcg acatgagcat cctactgtcg ccgccgtcgc tgctgctgct tcttgcagcc      780
cttgtggctc cagccaccct caccaccaac taccgaccgg attggaaccg tcttcgaggc      840
ctggccaggg ggcgggtgga gacctgtgga ggatgacagt tgaatcgcct aaaggaggtg      900
aaggcctttg tcaccgagga cattcaactg taccacaacc tggtgatgaa gcacctccct      960
ggggcagacc ccgaactcgt gctgttaagc cgaaattacc aggaactaga gcgaatccca     1020
ctcagccaaa tgacccggga cgagatcaat gcgctggtac aggagctcgg cttctaccgc     1080
aagtcggcgc cggaagctca ggtgccccccc gagtacctgt gggcgcccgc taagcccccc     1140
gaggaagctt cagaacacga cgacctgtag                                      1170
```

<210> SEQ ID NO 67
<211> LENGTH: 389
<212> TYPE: PRT
<213> ORGANISM: Mus musculus
<220> FEATURE:
<221> NAME/KEY: MISC_FEATURE
<222> LOCATION: (292)..(292)
<223> OTHER INFORMATION: Xaa is Selenocysteine residue

<400> SEQUENCE: 67

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205
```

-continued

```
Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Tyr
225                 230                 235                 240

Ser Asp Leu Asp Met Ser Ile Leu Leu Ser Pro Pro Ser Leu Leu Leu
                245                 250                 255

Leu Leu Ala Ala Leu Val Ala Pro Ala Thr Ser Thr Thr Asn Tyr Arg
                260                 265                 270

Pro Asp Trp Asn Arg Leu Arg Gly Leu Ala Arg Gly Arg Val Glu Thr
            275                 280                 285

Cys Gly Gly Xaa Gln Leu Asn Arg Leu Lys Glu Val Lys Ala Phe Val
            290                 295                 300

Thr Glu Asp Ile Gln Leu Tyr His Asn Leu Val Met Lys His Leu Pro
305                 310                 315                 320

Gly Ala Asp Pro Glu Leu Val Leu Leu Ser Arg Asn Tyr Gln Glu Leu
                325                 330                 335

Glu Arg Ile Pro Leu Ser Gln Met Thr Arg Asp Glu Ile Asn Ala Leu
                340                 345                 350

Val Gln Glu Leu Gly Phe Tyr Arg Lys Ser Ala Pro Glu Ala Gln Val
            355                 360                 365

Pro Pro Glu Tyr Leu Trp Ala Pro Ala Lys Pro Pro Glu Glu Ala Ser
            370                 375                 380

Glu His Asp Asp Leu
385
```